(12) United States Patent
Wells et al.

(10) Patent No.: US 8,792,978 B2
(45) Date of Patent: Jul. 29, 2014

(54) LASER-BASED NERVE STIMULATORS FOR, E.G., HEARING RESTORATION IN COCHLEAR PROSTHESES AND METHOD

(75) Inventors: Jonathon D. Wells, Seattle, WA (US); Andrew Xing, Bothell, WA (US); Mark P. Bendett, Kirkland, WA (US); Matthew D. Keller, Seattle, WA (US); Bryan J. Norton, Seattle, WA (US); James M. Owen, Redmond, WA (US); Shuming Yuan, Bothell, WA (US); Robert W. Royse, Kirkland, WA (US); Charles A. Lemaire, Apple Valley, MN (US)

(73) Assignee: Lockheed Martin Corporation, Bethesda, MD (US)

( * ) Notice: Subject to any disclaimer, the term of this patent is extended or adjusted under 35 U.S.C. 154(b) by 592 days.

(21) Appl. No.: 12/890,602

(22) Filed: Sep. 24, 2010

(65) Prior Publication Data

US 2011/0295331 A1 Dec. 1, 2011

Related U.S. Application Data

(60) Provisional application No. 61/349,810, filed on May 28, 2010, provisional application No. 61/349,813, filed on May 28, 2010, provisional application No. 61/381,933, filed on Sep. 10, 2010, provisional application No. 61/386,461, filed on Sep. 24, 2010.

(51) Int. Cl.
| | |
|---|---|
| *A61N 1/08* | (2006.01) |
| *A61N 1/36* | (2006.01) |
| *A61N 5/06* | (2006.01) |
| *A61N 1/05* | (2006.01) |
| *A61N 5/067* | (2006.01) |

(52) U.S. Cl.
CPC .......... *A61N 1/36032* (2013.01); *A61N 5/0622* (2013.01); *A61N 5/0601* (2013.01); *A61N 1/0541* (2013.01); *A61N 2005/0605* (2013.01); *A61N 2005/067* (2013.01); *A61N 2005/0631* (2013.01); *A61N 2005/0652* (2013.01); *A61N 2005/0665* (2013.01); *A61N 2005/0666* (2013.01); *A61N 2005/063* (2013.01); *A61N 1/361* (2013.01)

USPC .............. 607/3; 607/57; 607/88; 607/89

(58) Field of Classification Search
USPC ................................... 607/3, 88, 89
See application file for complete search history.

(56) References Cited

U.S. PATENT DOCUMENTS

| 4,064,872 A | 12/1977 | Caplan |
| 4,215,694 A | 8/1980 | Isakov et al. |

(Continued)

FOREIGN PATENT DOCUMENTS

| WO | WO 0025112 | 5/2000 |
| WO | WO 2007013891 A2 * | 2/2007 |

OTHER PUBLICATIONS

"The National Center for Voice and Speech" www.ncv s.org/ncv s/tutorials/voiceprod/tutorial/spectral.html.*

(Continued)

*Primary Examiner* — Gary Jackson
*Assistant Examiner* — Boniface N Nganga
(74) *Attorney, Agent, or Firm* — Charles A. Lemaire; Jonathan M. Rixen; Lemaire Patent Law Firm, P.L.L.C.

(57) ABSTRACT

Apparatus and method for optical- or optical-and-electrical stimulation of e.g., auditory nerve pathways, for example spiral ganglion in the cochlea or neurons in the cochlear nerve. Several configurations for guiding and directing the optical stimulation are disclosed. Several configurations for guiding and directing the electrical field (used in some embodiments, for sensitization) in and through the destination tissue to which the optical stimulation is directed are disclosed. In some embodiments, and array of IR VCSELs emit stimulation light, in particular to tissue in the cochlea for restoring hearing. In some embodiments, an electrical signal is also applied in a manner that reduces the amount of light in a pulse that is otherwise needed to elicit a NAP. In some embodiments, a heat dissipater is used to spread the heat generated by operation of the lasers and their circuits, to avoid heat damage to the tissue.

22 Claims, 34 Drawing Sheets

(56) References Cited

U.S. PATENT DOCUMENTS

| | | |
|---|---|---|
| 4,232,678 A | 11/1980 | Skovajsa |
| 4,296,995 A | 10/1981 | Bickel |
| 4,558,703 A | 12/1985 | Mark |
| 4,596,992 A | 6/1986 | Hornbeck |
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,530 B1 | 4/2003 | Shieh et al. |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,956,650 B2 | 10/2005 | Boas et al. |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,085,300 B2 | 8/2006 | Werner et al. |
| 7,095,770 B2 | 8/2006 | Johnson |
| 7,116,886 B2 | 10/2006 | Colgan et al. |
| 7,139,603 B2 | 11/2006 | Chance |
| 7,156,866 B1 | 1/2007 | Riggs et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,391,561 B2 | 6/2008 | Di Teodoro et al. |
| 7,402,167 B2 | 7/2008 | Nemenov |
| 7,647,112 B2 | 1/2010 | Tracey et al. |
| 7,736,382 B2 | 6/2010 | Webb et al. |
| 7,787,170 B2 | 8/2010 | Patel et al. |
| 7,797,029 B2 | 9/2010 | Gibson et al. |
| 7,873,085 B2 | 1/2011 | Babushkin et al. |
| 7,883,536 B1 | 2/2011 | Bendett et al. |
| 8,012,189 B1 | 9/2011 | Webb et al. |
| 2001/0021287 A1 | 9/2001 | Jewell et al. |
| 2002/0002391 A1 | 1/2002 | Gerdes |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0165171 A1 | 9/2003 | Jewell |
| 2003/0236458 A1 | 12/2003 | Hochman |
| 2004/0073101 A1 | 4/2004 | Chance |

(56) References Cited

U.S. PATENT DOCUMENTS

| | | |
|---|---|---|
| 2004/0116985 A1 | 6/2004 | Black |
| 2004/0225339 A1 | 11/2004 | Yaroslavsky et al. |
| 2004/0243111 A1 | 12/2004 | Bendett et al. |
| 2004/0243112 A1 | 12/2004 | Bendett et al. |
| 2005/0065531 A1 | 3/2005 | Cohen |
| 2005/0096720 A1 | 5/2005 | Sharma et al. |
| 2005/0099824 A1 | 5/2005 | Dowling et al. |
| 2005/0142344 A1 | 6/2005 | Toepel |
| 2005/0143789 A1 | 6/2005 | Whitehurst et al. |
| 2005/0169597 A1 | 8/2005 | Colgan et al. |
| 2005/0216072 A1 | 9/2005 | Mahadevan-Jansen et al. |
| 2005/0228256 A1 | 10/2005 | Labadie et al. |
| 2006/0095105 A1 | 5/2006 | Jog et al. |
| 2006/0129210 A1 | 6/2006 | Cantin et al. |
| 2006/0161218 A1 | 7/2006 | Danilov |
| 2006/0161227 A1 | 7/2006 | Walsh et al. |
| 2006/0167564 A1 | 7/2006 | Flaherty et al. |
| 2006/0276861 A1 | 12/2006 | Lin |
| 2007/0036493 A1 | 2/2007 | Brenner et al. |
| 2007/0053996 A1 | 3/2007 | Boyden et al. |
| 2007/0054319 A1 | 3/2007 | Boyden et al. |
| 2007/0060983 A1 | 3/2007 | Merfeld |
| 2007/0060984 A1 | 3/2007 | Webb et al. |
| 2007/0179557 A1 | 8/2007 | Maschino et al. |
| 2007/0191906 A1 | 8/2007 | Iyer et al. |
| 2007/0260297 A1 | 11/2007 | Chariff |
| 2007/0261127 A1 | 11/2007 | Boyden et al. |
| 2008/0009748 A1 | 1/2008 | Gratton et al. |
| 2008/0077198 A1 | 3/2008 | Webb et al. |
| 2008/0077200 A1 | 3/2008 | Bendett et al. |
| 2008/0086206 A1 | 4/2008 | Nasiatka et al. |
| 2008/0140149 A1 | 6/2008 | John et al. |
| 2008/0161697 A1 | 7/2008 | Chance |
| 2008/0183247 A1 | 7/2008 | Harding |
| 2009/0030327 A1 | 1/2009 | Chance |
| 2009/0054954 A1 | 2/2009 | Foley |
| 2009/0076115 A1 | 3/2009 | Wharton et al. |
| 2009/0163982 A1 | 6/2009 | DeCharms |
| 2009/0177255 A1 | 7/2009 | Merfeld |
| 2010/0049180 A1 | 2/2010 | Wells et al. |
| 2010/0114190 A1 | 5/2010 | Bendett et al. |
| 2010/0145418 A1 | 6/2010 | Zhang et al. |
| 2010/0162109 A1 | 6/2010 | Chatterjee et al. |
| 2010/0174329 A1* | 7/2010 | Dadd et al. .................... 607/3 |
| 2010/0184818 A1 | 7/2010 | Wharton et al. |
| 2010/0292758 A1 | 11/2010 | Lee et al. |
| 2011/0172725 A1 | 7/2011 | Wells et al. |

OTHER PUBLICATIONS

Princeton Lightwave (Company), "High Power Water Cooled Laser Stack", "http://www.princetonlightwave.com/images/pli_content/pli_high_power_multimode_laser_stacks.pdf", 2005.*

Allegre, et al., "Stimulation in the rat of a nerve fiber bundle by a short UV pulse from an excimer laser", "NeuroScience Letters ", 1994, pp. 261-264, vol. 180.

Arridge, et al., "The theoretical basis for the determination of optical pathlengths in tissue: temporal and frequency analysis", "Phys. Med. Biol. ", 1992, pp. 1531-1560, vol. 37.

Augustine, George J., "Combining patch-clamp and optical methods in brain slices", "Journal of Neuroscience Methods", 1994, pp. 163-169, vol. 54.

Banghart, Matthew, et al., "Light-activated ion channels for remote control of neuronal firing", "Nature Neuroscience", Nov. 21, 2004, pp. 1381-1386, vol. 7, No. 12.

Boyden, Edward S., et al., "Millisecond-timescale, genetically targeted optical control of neural activity", "Nature Neuroscience ", Sep. 2005, pp. 1263-1268, vol. 8, No. 9.

Bureau, Ingrid, et al., "Precise Development of Functional and Anatomical Columns in the Neocortex", "Neuron", Jun. 10, 2004, pp. 789-801, vol. 42.

Chambers, James J., et al., "Light-Induced Depolarization of Neurons Using a Modified Shaker K+ Channel and a Molecular Photoswitch", "Journal of Neurophysiology", Jul. 26, 2006, pp. 2792-2796, vol. 96.

Chance, et al., "Comparison of time-resolved and -unresolved measurements of deoxyhemoglobin in brain", "Proc. Nati. Acad. Sci. USA", Jul. 1988, pp. 4971-4975, vol. 85.

Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.

Desmurget, et al., "Movement Intention after Parietal Cortex Stimulation in Humans", "Science", May 8, 2009, pp. 811-813, vol. 324.

Dodt, H.-U., et al., "Circuitry of rat barrel cortex investigated by infrared-guided laser stimulation", "NeuroReport", Mar. 24, 2003, pp. 623-627, vol. 14, No. 4.

Dodt, H.-U., et al., "Precisely Localized LTD in the Neocortex Revealed by Infrared-Guided Laser Stimulation.", "Science ", Oct. 1, 1999, pp. 110-113, vol. 286.

Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.

Fork, Richard L., "Laser Stimulation of Nerve Cells in Aplysia", "Science, New Series", Mar. 5, 1971, pp. 907-908, vol. 171, No. 3974.

Haggard, "The Sources of Human Volition", "SCIENCE", May 8, 2009, pp. 731-733, vol. 324.

Izzo, et al., "Laser Stimulation of the Auditory Nerve", "Lasers in Surgery and Medicine", 2006, Publisher: Wiley-Liss, Inc.

Izzo, et al., "Selectivity of neural stimulation in the auditory system: a comparison of optic and electric stimuli", "Journal of Biomedical Optics", Mar./Apr. 2007, p. 021008, vol. 12, No. 2.

Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, pp. 1108-1114, vol. 54 No. 6(1).

Maiorov, M., et al., "218 W quasi-CW operation of 1.83 um two-dimensional laser diode array", "Electronics Letters", Apr. 15, 1999, pp. 636-638, vol. 35, No. 8.

Nakagawa, Atsuhiro, et al., "Pulsed holmium:yttrium—aluminum-garnet laser-induced liquid jet as a novel dissection device in neuroendoscopic surgery"; "J. Neurosurg.", Jul. 2004, pp. 145-150, vol. 101.

Naples, et al., "A spiral nerve cuff electrode for peripheral nerve stimulation", "IEEE Trans Biomed Eng", Nov. 1988, pp. 905-916, vol. 35, No. 11.

Passos, D., et al., "Tissue phantom for optical diagnostics based on a suspension of microspheres with a fractal size distribution", "Journal of Biomedical Optics.", Nov.-Dec. 2005, p. 064036, vol. 10, No. 6.

Princeton Lightwave (Company), "High Power Multimode Laser Arrays", "www.princetonlightwave.com/content/pli_high_power_multimode_laser_arrays.pdf", 2005.

Princeton Lightwave (Company), "High Power Water Cooled Laser Stack", "www.princetonlightwave.com", 2005.

Princeton Lightwave (Company), "High Power Single Element Laser", "www.princetonlightwave.com/content/HP%20Single%20Element%20Laser%20version%202.pdf", 2005.

Rolfe, "In Vivo Near-Infrared Spectroscopy", "Annu. Rev. Biomed. Eng.", 2000, pp. 715-754, vol. 2.

Schiefer, et al., "A Model of Selective Activation of the Femoral Nerve with a Flat Interface Nerve Electrode for a Lower Extremity Neuropr", "IEEE Trans Neural Syst Rehabil Eng", Apr. 2008, pp. 195-204, vol. 16, No. 2.

Schwartz, et al., "Auditory Brainstem Implants", "Neurotherapeutics: The Journal of the American Society for Experimental NeuroTherapeutics", Jan. 2008, pp. 128-136, vol. 5.

Tarler, et al., "Comparison of joint torque evoked with monopolar and tripolar-cuff electrodes", "IEEE Trans Neural Syst Rehabil Eng ", 2003, pp. 227-235, vol. 11, No. 3.

Teudt, et al., "Optical Stimulation of the Facial Nerve: A New Monitoring Technique'?", "The Laryngoscope ", 2007, pp. 1641-1647, vol. 117, No. 9.

(56) References Cited

OTHER PUBLICATIONS

Vogel, Alfred, et al., "Mechanisms of pulsed laser ablation of biological tissues.", "Chemical Reviews", 2003, pp. 577-644, vol. 103, No. 2.
Wells, Jonathon, et al., "Application of Infrared Light for in vivo Neural Stimulation.", "Journal of Biomedical Optics ", Nov. 2005, pp. 064003-1 to 064003-12, vol. 10, No. 6.
Wells, Jonathon, et al., "Optical stimulation of neural tissue in vivo", "Optics Letters ", Mar. 1, 2005, pp. 504-506, vol. 30, No. 5.
Wells, Jonathon D., et al., "Optically Mediated Nerve Stimulation: Identification of Injury Thresholds.", "Lasers in Surgery and Medicine ", 2007, pp. 513-526, vol. 39.
Wells, Jonathon, et al., "Pulsed laser versus electrical energy for peripheral nerve stimulation", "Journal of Neuroscience Methods ", 2007, pp. 326-337, vol. 163.
Yoo, et al., "Selective recording of the canine hypoglossal nerve using a multicontact flat interface nerve electrode", "IEEE Trans Biomed Eng", Aug. 2005, pp. 1461-1469, vol. 52, No. 8.
Zemelman, Boris V., et al. , "Photochemical gating of heterologous ion channels: Remote control over genetically designated populations of neurons", "Proceedings of the National Academy of Sciences", Feb. 4, 2003, pp. 1352-1357, vol. 100, No. 3.
Zhang, Feng, et al. , "Channelrhodopsin-2 and optical control of excitable cells", "Nature Methods", Sep. 21, 2006, pp. 785-792, vol. 3, No. 10.
Bernstein, Jacob G., et al., "Prosthetic systems for therapeutic optical activation and silencing of genetically-targeted neurons", "Proc Soc Photo Opt Instrum Eng.", May 5, 2008, vol. 6854: 68540H.
Han, Xue, et al., "Multiple-Color Optical Activation, Silencing, and Desynchronization of Neural Activity, with Single-Spike Temporal Resol", "PLoS ONE 2(3): e299. doi:10.1371/journal.pone. 0000299", Mar. 2007, p. e299, No. 3, Publisher: www.plosone.org.
Huang, Ying-Ying, et al., "Biphasic Dose Response in Low Level Light Therapy", "Dose-Response", 2009, p. (s) 358-383, vol. 7.

\* cited by examiner

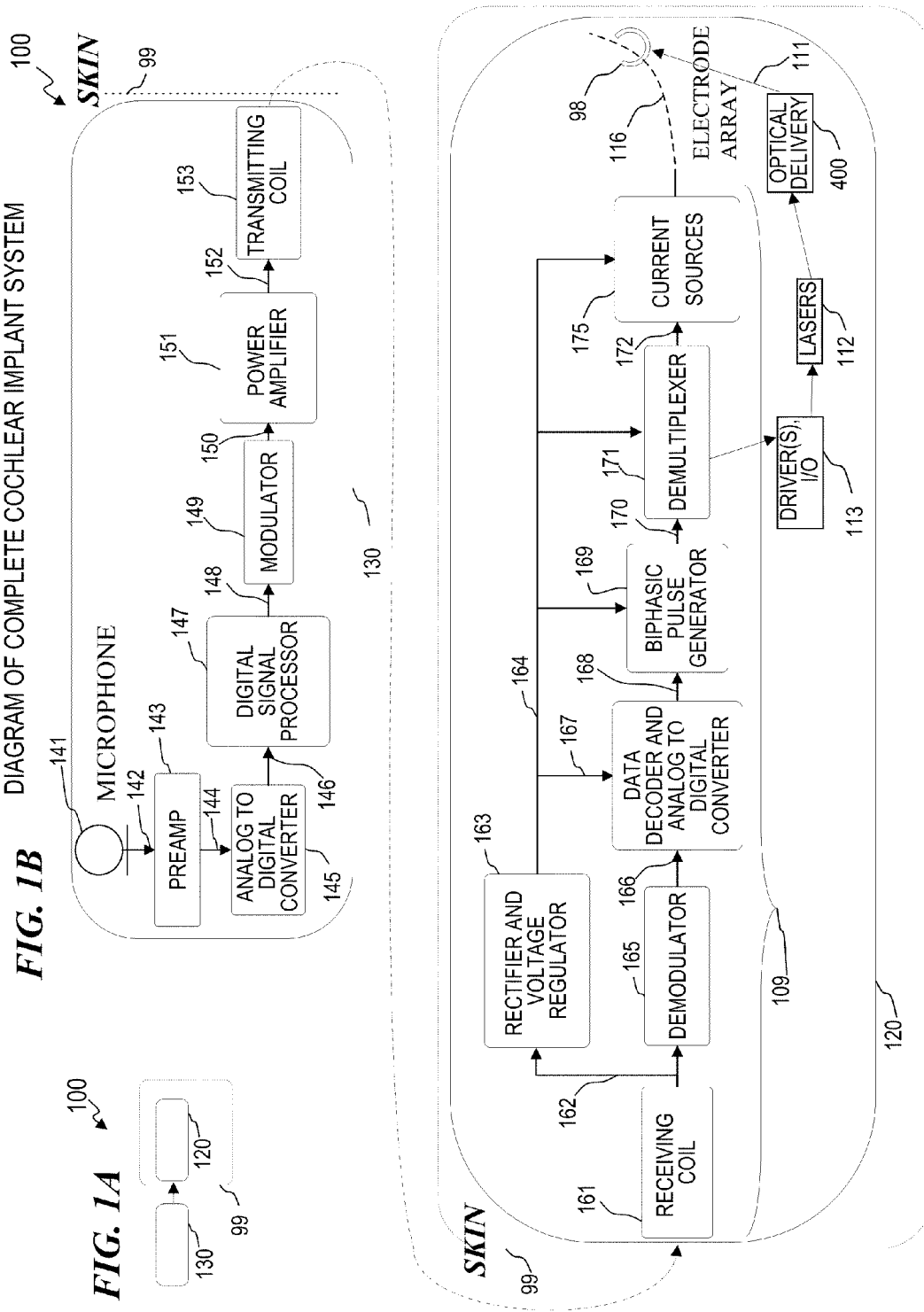

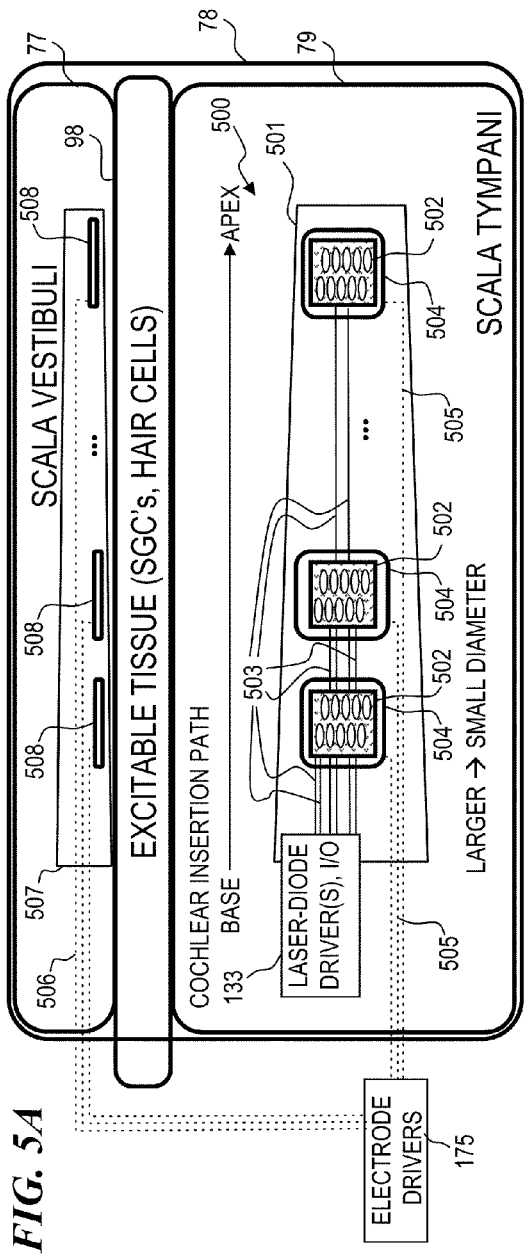

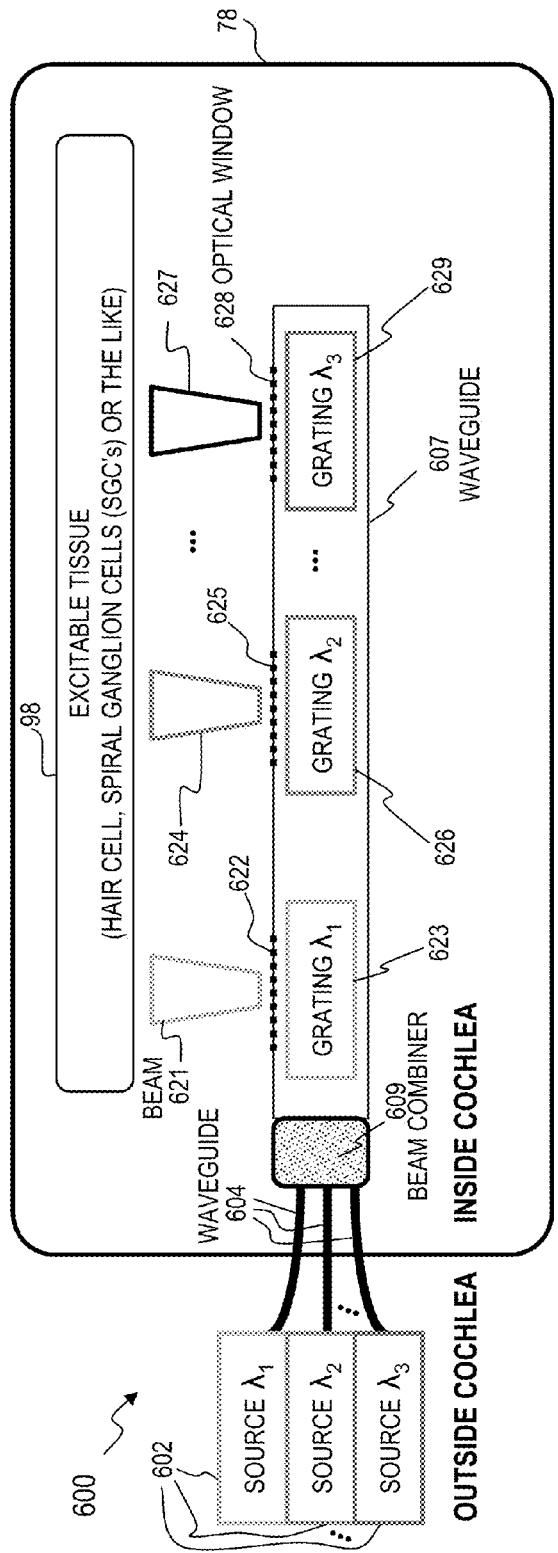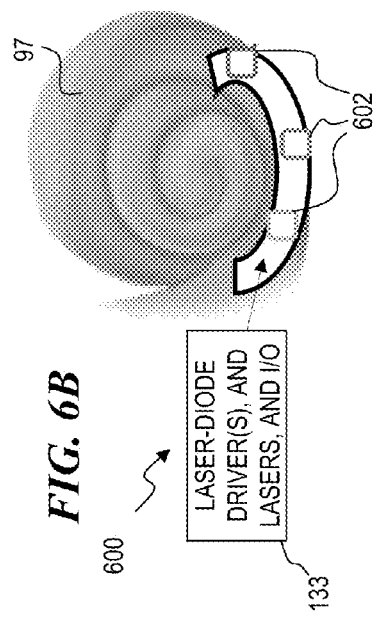

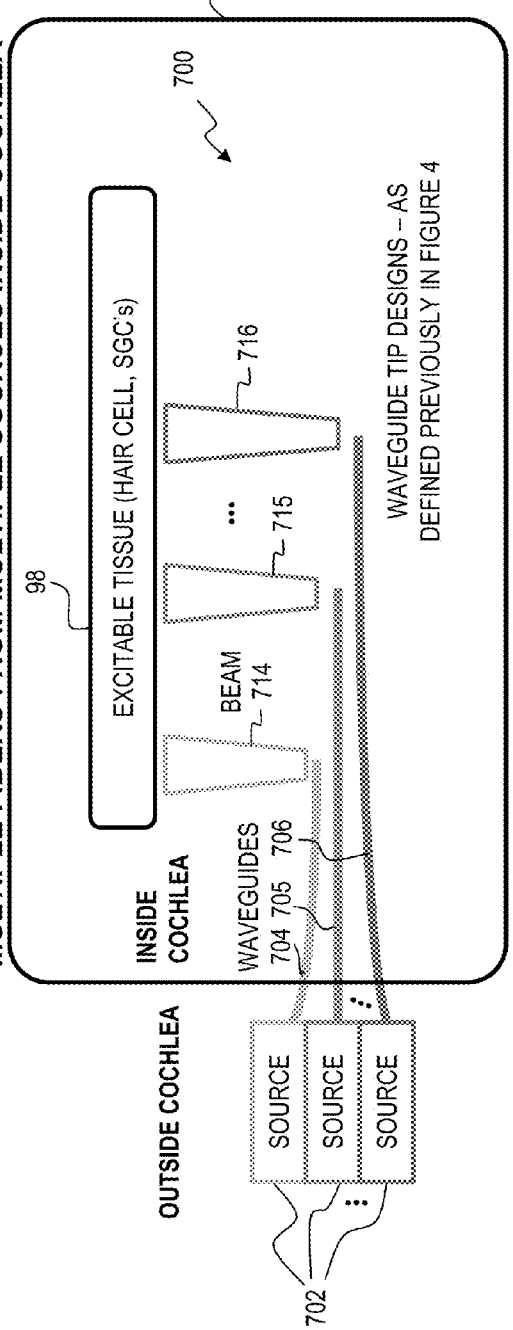
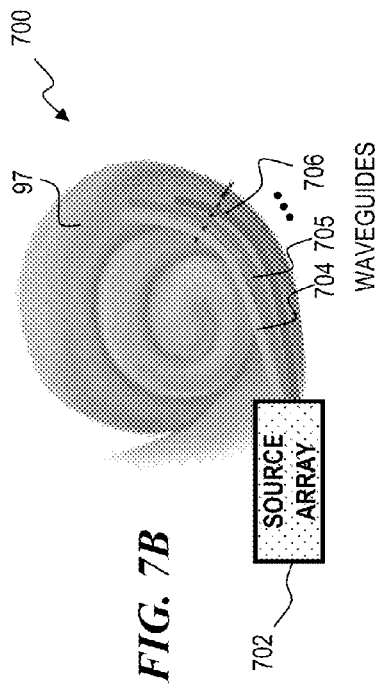
FIG. 7A
FIG. 7B

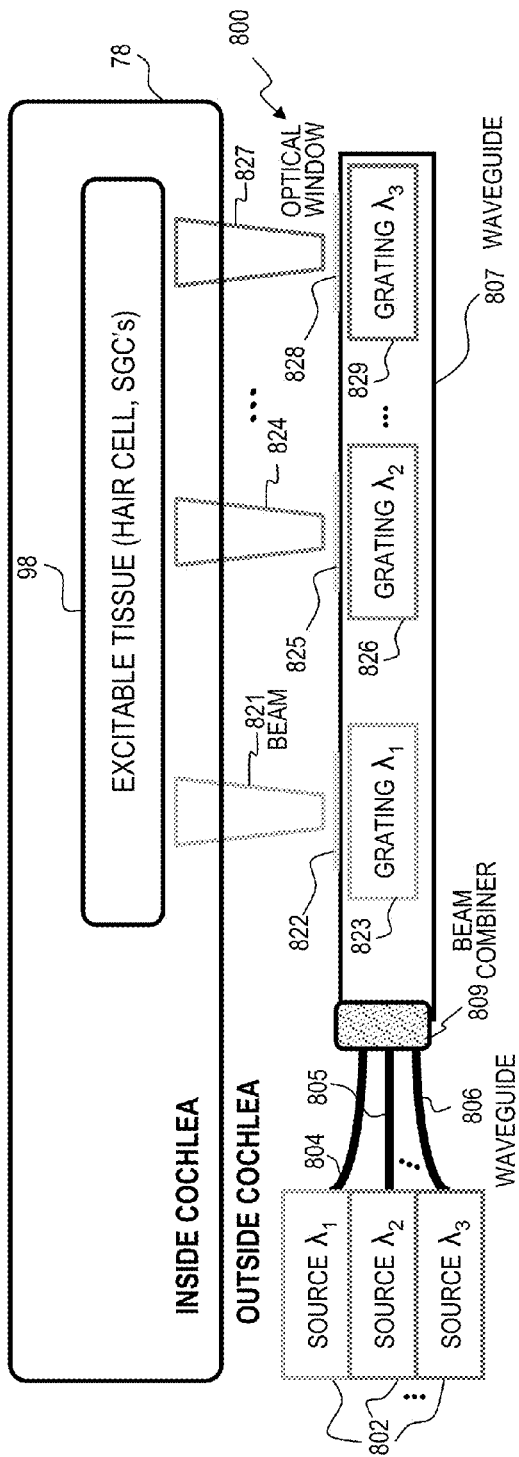
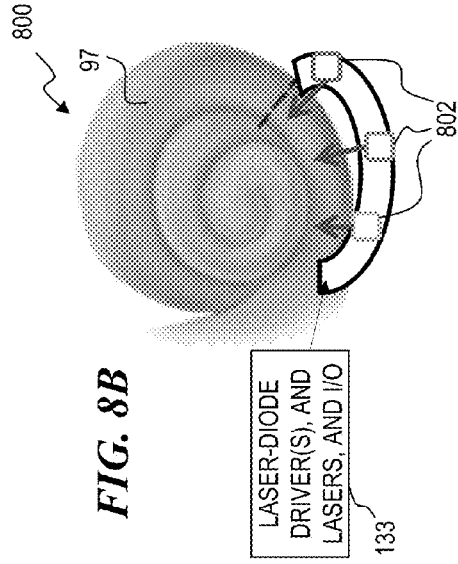
FIG. 8A
FIG. 8B

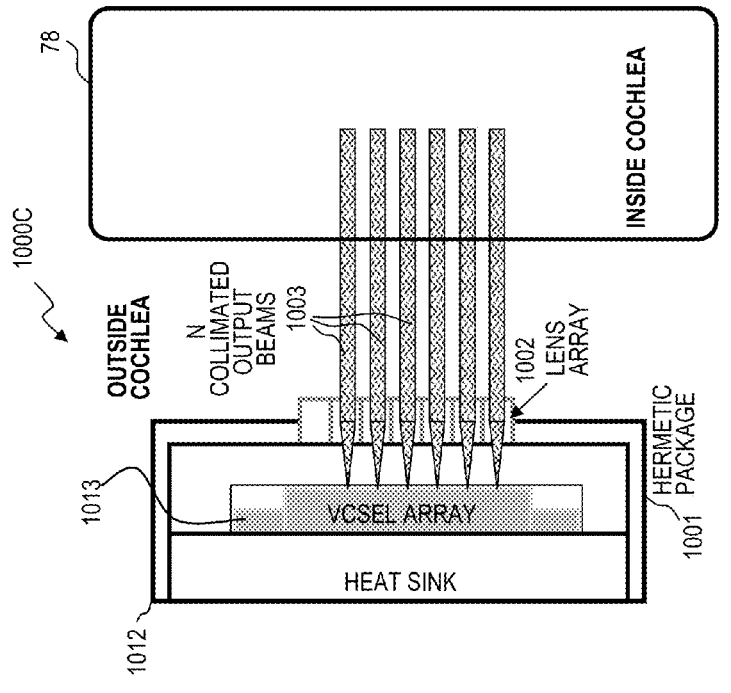
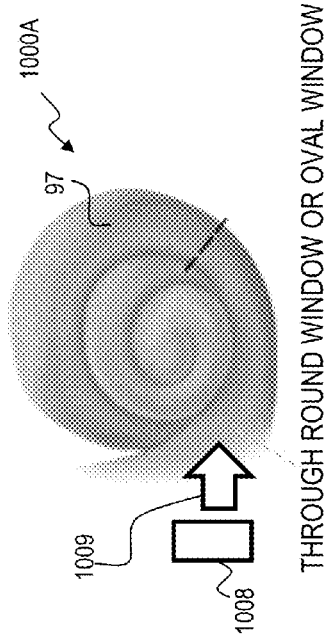
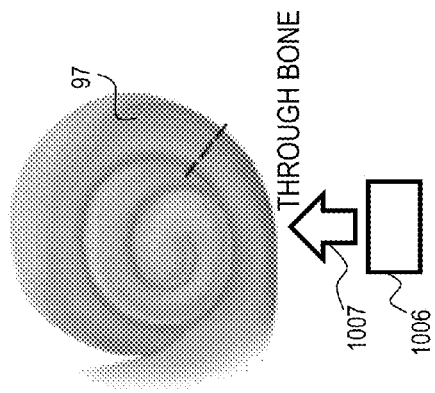
FIG. 10A, FIG. 10B, FIG. 10C — VCSEL 3-D ARRAY OUTSIDE COCHLEA

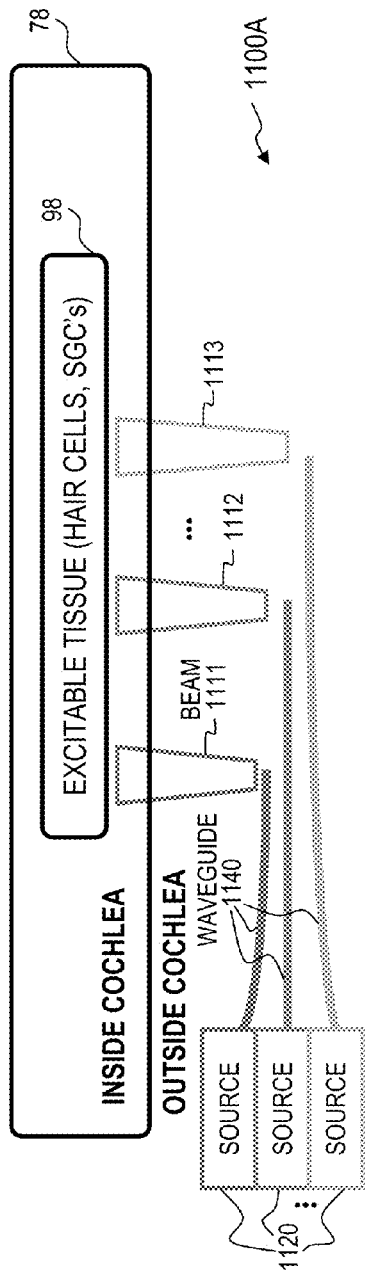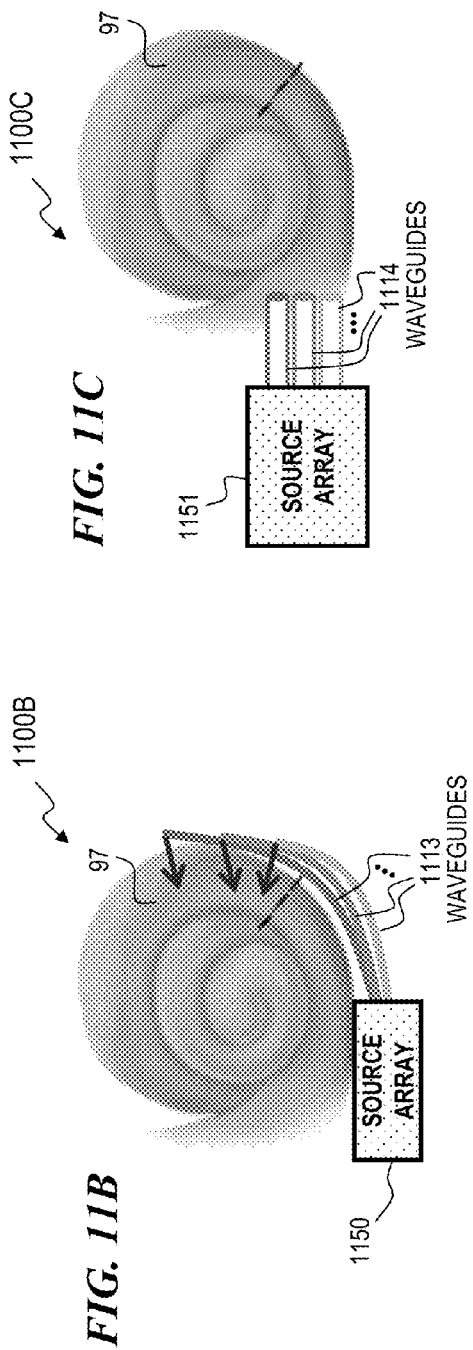

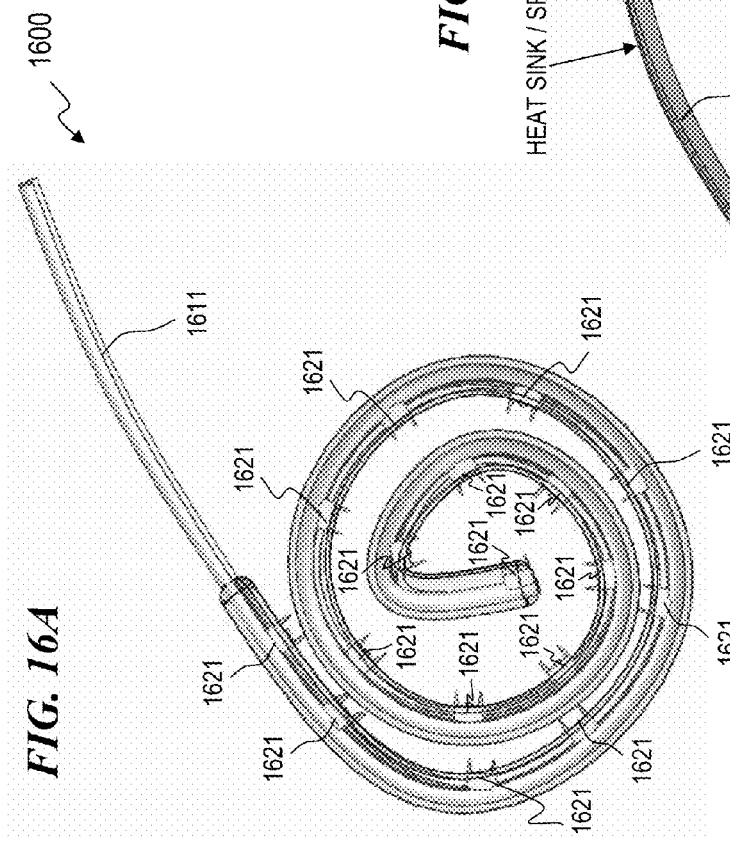
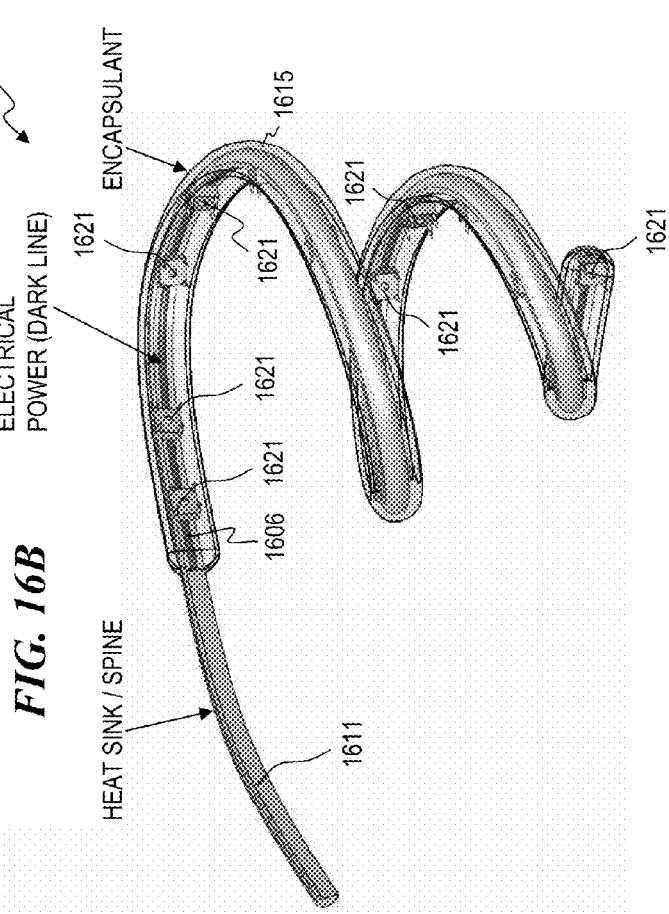
FIG. 16A
FIG. 16B

ELECTRICLY TUNABLE DICHROIC MIRROR IN WAVEGUIDE

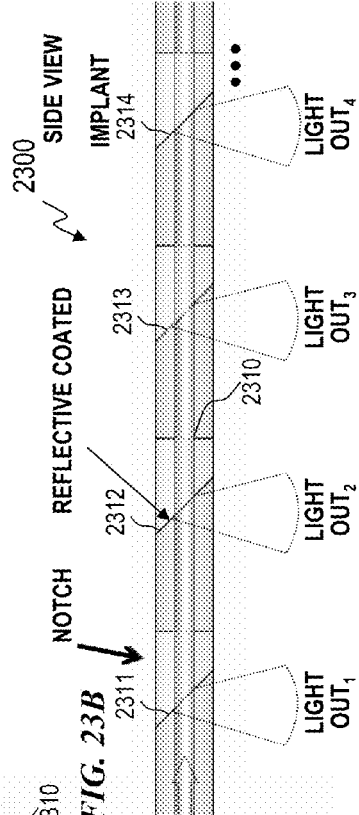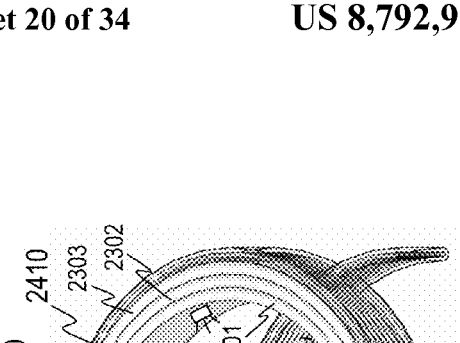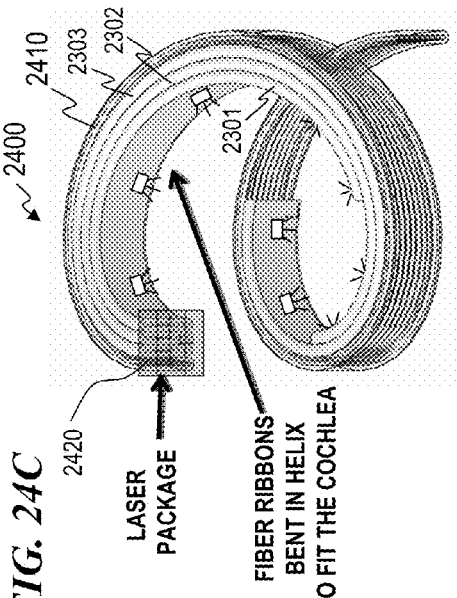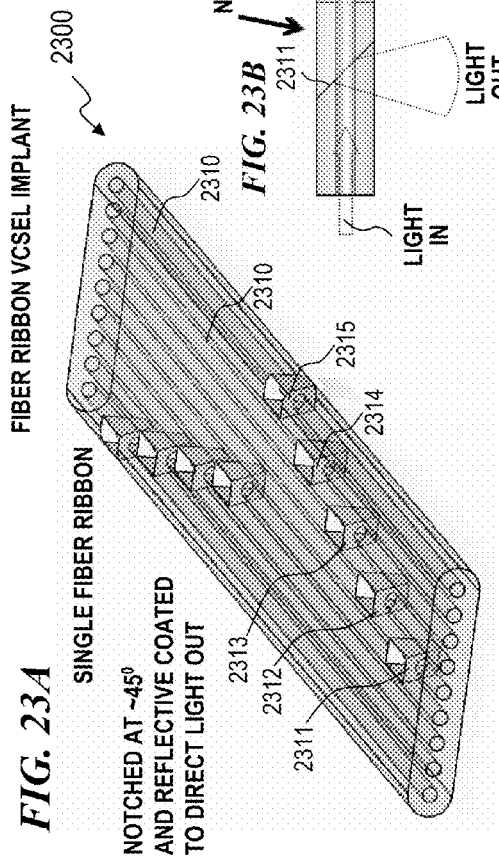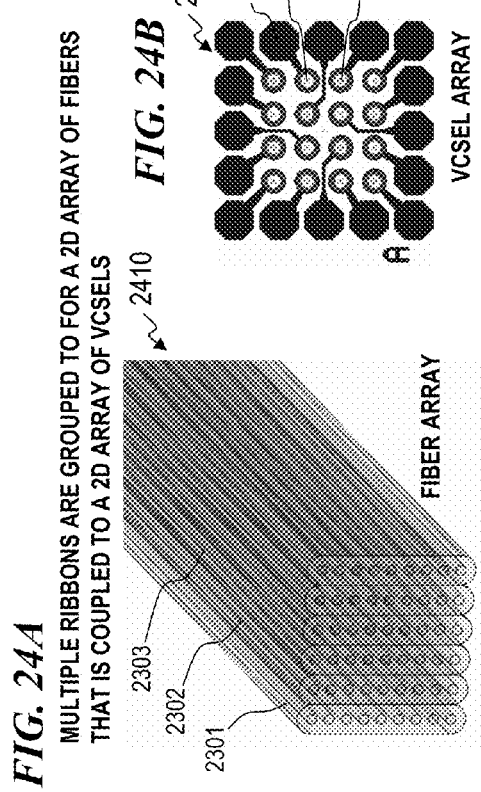
FIG. 23A
FIG. 23B
FIG. 24A
FIG. 24B
FIG. 24C

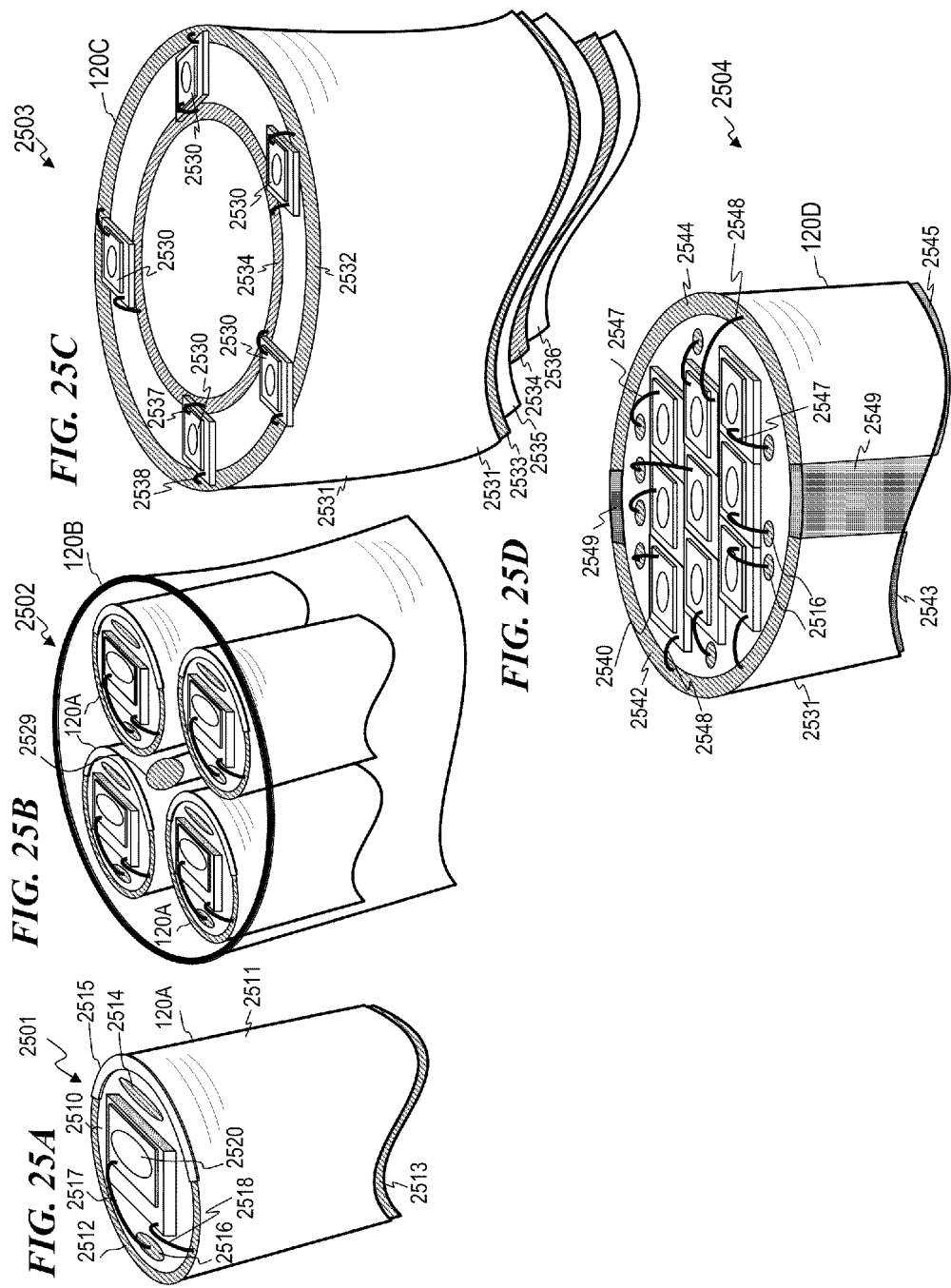

FIG. 33

SUBSTRATE-LEVEL PACKAGING EMBODIMENTS

SUBSTRATE DESIGN TO ENSURE SHORT DISTANCE BETWEEN LASER SOURCE AND COCHLEAR NERVE BUNDLE FOR ALL LASERS CONSISTENTLY, WHICH WILL RESULT IN LOWER LASER ENERGY REQUIREMENT FOR ADEQUATE STIMULATION. FOR SAFETY AND THERMAL MANAGEMENT CONSIDERATION, CLOSE PROXIMITY MINIMIZES LASER ENERGY NEEDED TO STIMULATE. (FIG.1)

- SUBSTRATE TOPOLOGY DESIGN ("CONE" SHAPED) TO MAINTAIN CLOSE PROXIMITY

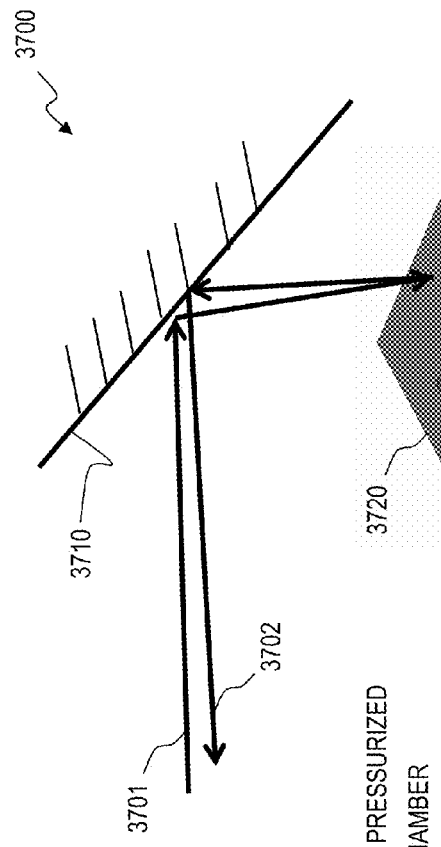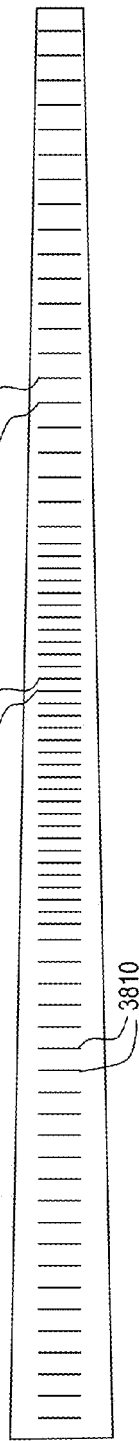
*FIG. 37*
UNIQUE HERMETICAL PACKAGING DESIGN TO ALLOW FAST HERMETICITY EXAMINATION BY OPTICAL LEAK TESTING
TESTED IN PRESSURIZED HELIUM CHAMBER
*FIG. 38*
- NON-UNIFORM SPACING TO CONCENTRATE EMITTERS IN MIDDLE, OR LOW-MIDDLE
- 300-3000 HZ FOR SOME EMBODIMENTS
- FOCUS ON CENTER OF COCHLEA

FIG. 39

METHODS TO PHYSICALLY SECURE IMPLANT TO THE COCHLEA CONT. — 3900

MOUNTING SCHEMES

USE A SEMS (SELF EXPANDABLE METAL STENT) TO FIX FIBER OR VCSEL SUBSTRATE TO COCHLEAR WALL. WILL NEED TO ORIENT FIBER/SUBSTRATE FOR LIGHT DELIVERY TO NERVE

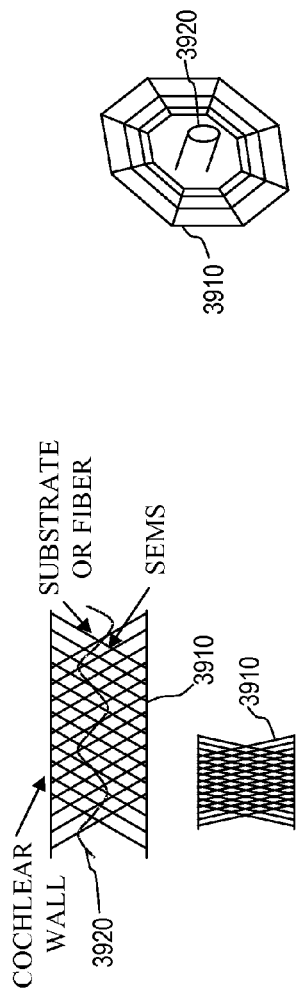

COCHLEAR WALL — 3920
SUBSTRATE OR FIBER
SEMS
3910

3920
3910

HELICAL STENT THAT IS HOLLOW AND CARRIES ELEC. SIGNAL AND/OR ADDITIONAL COOLING

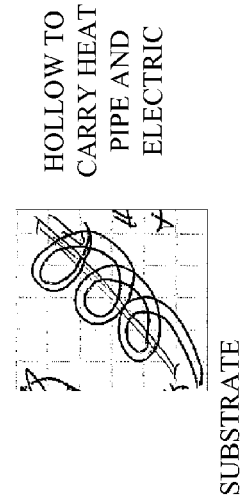

HOLLOW TO CARRY HEAT PIPE AND ELECTRIC

SUBSTRATE

NOTE THAT THE STENT MATERIAL COULD ALSO BE A NON-METALLIC MATERIAL SUCH AS POLYETHYLENE.

LASER-BASED NERVE STIMULATORS FOR, E.G., HEARING RESTORATION IN COCHLEAR PROSTHESES AND METHOD

CROSS-REFERENCE TO RELATED APPLICATIONS

This invention claims benefit under 35 U.S.C. §119(e) of U.S. Provisional Patent Application No. 61/349,810 filed May 28, 2010, by Jonathon D. Wells et al., titled "Implantable Infrared Nerve Stimulation Devices for Peripheral and Cranial Nerve Interfaces";

U.S. Provisional Patent Application No. 61/386,461 filed Sep. 24, 2010, by Jonathon D. Wells et al., titled "Implantable Infrared Nerve Stimulation Devices for Peripheral and Cranial Nerve Interfaces";

U.S. Provisional Patent Application No. 61/349,813 filed May 28, 2010, by Jonathon D. Wells et al., titled "Laser-Based Nerve Stimulators for, e.g., Hearing Restoration in Cochlear Prostheses"; and U.S. Provisional Patent Application No. 61/381,933 filed Sep. 10, 2010, by Jonathon D. Wells et al., titled "Laser-Based Nerve Stimulators for, e.g., Hearing Restoration in Cochlear Prostheses";

each of which is incorporated herein by reference in its entirety.

RELATED APPLICATIONS

The present invention is related to the following prior applications and patents:

U.S. Provisional Patent Application No. 60/715,884 filed Sep. 9, 2005, titled "Apparatus and Method for Optical Stimulation of Nerves";

U.S. Provisional Patent Application No. 60/826,538 filed Sep. 21, 2006, titled "Miniature Apparatus and Method for Optical Stimulation of Nerves and Other Animal Tissue";

U.S. Provisional Patent Application No. 60/872,930 filed Dec. 4, 2006, titled "Apparatus and Method for Characterizing Optical Sources used with Human and Animal Tissues";

U.S. Provisional Patent Application No. 60/884,619 filed Jan. 11, 2007, titled "Vestibular Implant using Infrared Nerve Stimulation";

U.S. Provisional Patent Application No. 60/885,879 filed Jan. 19, 2007, titled "Hybrid Optical-Electrical Probes";

U.S. Provisional Patent Application No. 60/964,634 filed Aug. 13, 2007, titled "VCSEL Array Stimulator Apparatus and Method for Light Stimulation of Bodily Tissues";

U.S. Provisional Patent Application No. 61/015,665 filed Dec. 20, 2007, titled "Laser Stimulation of the Auditory System at 1.94 µm and Microsecond Pulse Durations";

U.S. Provisional Patent Application No. 61/081,732 filed Jul. 17, 2008, titled "Method and Apparatus for Neural Signal Capture to Drive Neuroprostheses or Bodily Function";

U.S. Provisional Patent Application No. 61/102,811 filed Oct. 3, 2008, titled "Nerve Stimulator and Method using Simultaneous Electrical and Optical Signals";

U.S. Provisional Patent Application No. 61/147,073 filed Jan. 23, 2009, titled "Optical Stimulation Using Infrared Lasers (or In Combination with Electrical Stimulation) of the Auditory Brainstem and/or Midbrain";

U.S. patent application Ser. No. 11/257,793 (now U.S. Pat. No. 7,736,382 issued Jun. 15, 2010 filed Oct. 24, 2005, titled "Apparatus and Method for Optical Stimulation of Nerves and Other Animal Tissue";

U.S. patent application Ser. No. 11/536,639 (now U.S. Pat. No. 7,988,688, issued Aug. 2, 2011 filed Sep. 28, 2006, titled "Miniature Apparatus and Method for Optical Stimulation of Nerves and Other Animal Tissue";

U.S. patent application Ser. No. 11/948,912 filed Nov. 30, 2007, titled "Apparatus and Method for Characterizing Optical Sources used with Human and Animal Tissues";

U.S. patent application Ser. No. 11/536,642 filed Sep. 28, 2006, titled "Apparatus and Method for Stimulation of Nerves and Automated Control of Surgical Instruments";

U.S. patent application Ser. No. 11/971,874 (now U.S. Pat. No. 8,012,189, issued Sep. 6, 2011 filed Jan. 9, 2008, titled "Method and Vestibular Implant using Optical Stimulation of Nerves";

U.S. patent application Ser. No. 12/018,185 (now U.S. Pat. No. 7,883,536, issued Feb. 8, 2011 filed Jan. 22, 2008, titled "Hybrid Optical-Electrical Probes";

U.S. patent application Ser. No. 12/191,301 (now U.S. Pat. No. 8,475,506, issued Jul. 2, 2013) filed Aug. 13, 2008, titled "VCSEL Array Stimulator Apparatus and Method for Light Stimulation of Bodily Tissues";

U.S. patent application Ser. No. 12/505,462 (now abandoned) filed Jul. 17, 2009, titled "Apparatus and Method for Neural-Signal Capture to Drive Neuroprostheses or Control Bodily Function";

U.S. patent application Ser. No. 12/573,848 (now U.S. Pat. No. 8,160,696, issued Apr. 17, 2012 filed Oct. 5, 2009, titled "Nerve Stimulator and Method using Simultaneous Electrical and Optical Signals"; and U.S. patent application Ser. No. 12/693,427 (now U.S. Pat. No. 8,744,570, issued Jun. 3, 2014) filed Jan. 25, 2010, titled "Optical Stimulation of the Brainstem and/or Midbrain, including Auditory Areas"; each of which is incorporated herein by reference in its entirety.

FIELD OF THE INVENTION

The present invention is related to optical waveguides and tissue electro-optics (interactions of electricity and light with human or non-human animal tissue), and in particular, to systems that include optical waveguides (such as one or more optical fibers in a bundle) or focussing/guiding interfaces at the light-exit port of vertical-cavity surface-emitting lasers (VCSELs) that are especially suited to propagating light pulses (e.g., ones suitable for eliciting a nerve action potential (NAP) response when directed to nerve tissue) from an optical source (e.g., a source having at least one infrared (IR) semiconductor laser such as an array of VCSELs) to a destination tissue in a living animal, in particular to tissue in the cochlea of the inner ear of the animal for restoring hearing; in some embodiments, an electrical signal is also applied in a manner that reduces the amount of light in a pulse that is otherwise needed to elicit a NAP; in some embodiments, a heat dissipater is used to spread the heat generated by operation of the lasers and the circuits used to drive the lasers, in order to avoid heat damage to surrounding tissue.

BACKGROUND

A person's two inner-ear organs (one associated with the right-hand ear and the other associated with the left-hand ear) each include the labyrinth, a delicate membranous system of fluid passages that includes both the cochlea (which is part of the auditory system), and the vestibular system (which provides part of the sense of balance).

Each inner-ear includes a tympanic membrane (eardrum) that receives sounds from the environment and conducts the resulting vibrations to the cochlea via the three auditory ossicles (the tympanic membrane connects to the malleus (hammer), which articulates with the incus (anvil), which is attached to stapes (stirrup), which is attached to the membrane of the fenestra ovalis, the oval membrane between the middle ear and the vestibule of the inner ear). Inside the coiled cochlea is the Organ of Corti, which converts sound vibrations into nerve action potentials (NAPs) that convey auditory information to the person's brain. Different positions along the length of the Organ of Corti between the two spiral fluid paths of the cochlea are responsive to different sound frequencies. Thus, in order to provide good hearing to a person who has lost her or his sense of hearing, it would be desirable to increase the number of separate stimulation signals to different spiral ganglion cells in the cochlea, or other auditory neurons and nerves. When electrical stimulation is used to trigger auditory NAPs, the number of separate signals is limited because the electrical field is diffuse and each electrode will stimulate neighboring nerves to the nerve to which the stimulation is directed. Several of the related patent applications identified above describe the advantages of using optical stimulation to provide reliable triggering of the desired NAPs for a particular auditory nerve while reducing inadvertent stimulation of neighboring auditory nerves.

Each inner-ear also includes three semicircular canals and a vestibule, the region where the semicircular canals converge, and which is close to the cochlea (the hearing organ). The vestibular system also works with the visual system to keep objects in focus when the head is moving. In addition to sense-of-balance signals from the vestibular system, the person's eyes also provide signals used for balance, as do joint and muscle receptors and the cerebellum. A bundle of nerves carries NAP signals from the inner ear organs to the brain. The brain, specifically the vestibular nuclear complex, receives and analyzes the information from these systems, and generates signals that control a person's balance.

U.S. Pat. No. 7,225,028 issued to Della Santina et al. on May 29, 2007, and titled "Dual Cochlear/Vestibular Stimulator with Control Signals Derived from Motion and Speech Signals", is incorporated herein by reference. Della Santina et al. describe a system for treating patients affected both by hearing loss and by balance disorders related to vestibular hypofunction and/or malfunction, which includes sensors of sound and head movement, processing circuitry, a power source, and an implantable electrical stimulator capable of stimulating areas of the cochlea and areas of the vestibular system.

As a convention used herein, a nerve will be defined as a collection of individual nerve fibers (i.e., axons) of individual nerve cells (neurons) that together form a set of nerve pathways (an integrated set of pathways for signal propagation within the nervous system). Subsets of the individual nerve fibers are each bundled into one of a plurality of fascicles that together form the nerve. Action potentials can occur in the axon portion of individual nerve cells. A series of individual nerve fibers that together form an integrated signal pathway starting at a sensory-receptor nerve ending and extending to the brain will be referred to as a sensory-nerve pathway, a series of individual nerve fibers that together form an integrated signal pathway starting at the brain and extending to a muscle cell will be referred to as a motor-nerve pathway. A sensory-nerve pathway that carries auditory signals will be referred to as an auditory-nerve pathway, and a sensory-nerve pathway that carries signals from the sense-of-balance organs (e.g., the vestibular organs of the inner ear, or perhaps the eyes) will be referred to as a sense-of-balance nerve pathway. The auditory nerve pathways extend from spiral ganglion nerves (ganglion of Corti) in the organ of Corti of the cochlea, through the auditory nerve (also called the cochlear nerve, which, when joined with the vestibular nerve (for the sense of balance) becomes part of the vestibulocochlear nerve (also called cranial nerve VIII)) that extends to the cochlear nucleus of the brainstem, midbrain and then to the auditory cortex.

Within each fascicle of a nerve, there will typically be a plurality of sensory-nerve pathways and a plurality of motor-nerve pathways, wherein the number of sensory-nerve pathways will typically be about fifteen times as many as the number of motor-nerve pathways. As well, a series of individual nerve fibers may together form an integrated pathway starting at one of various internal organs and ending in the brain, with then other series of individual nerve fibers together forming an integrated pathway starting at the brain and extending to some internal end organ (such as the digestive tract, the heart, or blood vessels) as part of the autonomic nervous system; and a series of individual nerve fibers may together form an integrated pathway within the brain referred to as a tract. As used herein, a nerve bundle or fascicle refers to a collection of nerve fibers that subserve a like function (e.g., a fascicle may support a plurality of different motor-nerve pathways and thus motor-control signals needed for the muscles for a hand grasp, for example; similarly the same and/or a nearby fascicle may support a plurality of corresponding sensory-nerve pathways and thus sensory signals that provide the brain with feedback for the hand grasp).

Applying an electrical signal across or into a neuron (nerve cell), or a nerve bundle or nerve, is one way to stimulate a nerve action potential (NAP), either in a single neuron (nerve cell), or in a plurality of neurons within a nerve bundle, or within a nerve (the combined signals of NAPs in a nerve bundle or nerve are referred to as a compound nerve action potential (CNAP)). Applying an optical signal (e.g., a short relatively high-power pulse of infrared (IR) laser light, for example at a signal wavelength about 1.9 microns) is another way to stimulate a NAP.

U.S. patent application Ser. No. 12/018,185 filed Jan. 22, 2008 by Mark P. Bendett and James S. Webb, titled "Hybrid Optical-Electrical Probes," which is incorporated herein by reference in its entirety, describes an optical-signal vestibular-nerve stimulation device and method that provides different nerve stimulation signals to a plurality of different vestibular nerves, including at least some of the three semicircular canal nerves and the two otolith organ nerves. In some embodiments described in that patent application, balance conditions of the person are sensed by the implanted device, and based on the sensed balance conditions, varying infrared (IR) nerve-stimulation signals are sent to a plurality of the different vestibular nerves. Also described is a method that includes obtaining light from an optical source; transmitting the light through an optical fiber between a tissue of an animal and an optical transducer, and detecting electrical signals using conductors attached to the optical fiber. The application also describes an apparatus that includes an optical source, an optical transmission medium operatively coupled to the optical source and configured to transmit light from the optical source to respective nerves of each of one or more organs of an animal, an electrical amplifier, and an electrical transmission medium integral with the optical transmission medium and operatively coupled to the electrical amplifier, wherein the electrical transmission medium is configured to transmit an electrical signal from the respective nerves to the electrical amplifier.

One way to treat deafness or hearing loss in a person is to implant a cochlear-stimulation device (frequently called a cochlear implant) that senses sound in the environment (e.g., using a microphone) and then generates a combination of different electrical signals in different locations in the person's cochlear inner-ear structure. Because it is difficult to confine the electric field of each one of a large number of separate electrical signals, each intended for a particular one of a large number of separate nerve pathways, e.g., among those nerve pathways that extend in the bundle from the cochlea into the brain (using conventional stimulation devices it is possible to generate CNAP responses in perhaps only sixteen different nerve pathways (channels)), this conventional approach can provide only a crude representation of normal hearing.

U.S. Pat. No. 6,921,413 issued Jul. 26, 2005 to Mahadevan-Jansen et al., titled "Methods and devices for optical stimulation of neural tissues," and U.S. Pat. No. 7,736,382, which issued Jun. 15, 2010 to Webb et al. titled "Apparatus for Optical Stimulation of Nerves and Other Animal Tissue," are each incorporated herein by reference in their entirety. Both of these describe optical stimulation of nerves in general.

U.S. Patent Application Publication No. US 2006/0161227, of Walsh et al., titled "Apparatus and Methods for Optical Stimulation of the Auditory Nerve," is incorporated herein by reference in its entirety. This application describes a cochlear implant placed in a cochlea of a living subject for stimulating the auditory system of the living subject, where the auditory system comprises auditory neurons. In one embodiment, the cochlear implant includes a plurality of light sources $\{L_i\}$, placeable distal to the cochlea, each light source being operable independently and adapted for generating an optical energy, $E_i$, wherein i=1, . . . , N, and N is the number of the light sources, and delivering means placeable in the cochlea and optically coupled to the plurality of light sources, $\{L_i\}$, such that in operation, the optical energies $\{E_i\}$ generated by the plurality of light sources $\{L_i\}$ are delivered to target sites, $\{G_i\}$, of auditory neurons, respectively, wherein the target sites $G_1$ and $G_N$ of auditory neurons are substantially proximate to the apical end and the basal end of the cochlea, respectively.

U.S. Pat. No. 4,596,992 to Hornbeck issued Jun. 24, 1986 "Linear spatial light modulator and printer", is incorporated herein by reference in its entirety. Hornbeck describes linear spatial light modulator with two offset rows of pixels for slight overlap of images, and a printer system using such a spatial light modulator with dark field projection optics is disclosed. The pixels include electrostatically deflectable elements which all bend in the same direction to permit use of dark field projection. The addressing electrodes for the elements are beneath the reflecting surface and arranged perpendicular to the rows of pixels with half on each side of the rows. The printer uses a xerographic engine for conversion of modulated light into print, and an entire row is printed without any scanning.

U.S. Pat. No. 7,787,170 to Patel et al., which issued Aug. 31, 2010 titled "Micromirror array assembly with in-array pillars", is incorporated herein by reference in its entirety. Patel et al. describe a microstructure device comprising multiple substrates with the components of the device formed on the substrates. In order to maintain uniformity of the gap between the substrates, a plurality of pillars is provided and distributed in the gap so as to prevent decrease of the gap size. The increase of the gap size can be prevented by bonding the pillars to the components of the microstructure. Alternatively, the increase of the gap size can be prevented by maintaining the pressure inside the gap below the pressure under which the microstructure will be in operation. Electrical contact of the substrates on which the micromirrors and electrodes are formed can be made through many ways, such as electrical contact areas, electrical contact pads and electrical contact springs.

U.S. Patent Application Publication 2010/0162109 to Chatterjee et al. published Jun. 24, 2010 titled "USER INTERFACE HAVING CHANGEABLE TOPOGRAPHY", and is incorporated herein by reference. Chatterjee et al. describe a device having changeable topography. The device can have a shape-changeable surface that can selectively alter according to an input so as to provide changeable topography of the user interface. The surface can include individual nodes that can raise above or lower below the initial surface. Alternatively, the surface can include a shape changeable material that can change the shape of portions thereof into discrete shapes above or below the initial surface. Alternatively, the surface can include a deformable material that can deform portions thereof into discrete forms above or below the initial surface. The changeable topography can define different user interface layouts.

U.S. Pat. No. 7,797,029 titled "Auditory midbrain implant" issued Sep. 14, 2010 to Peter Gibson et al. is incorporated herein by reference. Gibson et al. describe an electrode array that is implantable within the inferior colliculus of the midbrain and/or other appropriate regions of the brain of an implantee and adapted to provide electrical stimulation thereto. The electrode array an elongate member having a plurality of electrodes mounted thereon in a longitudinal array. A delivery cannula for delivering the electrode array having two half-pipes is also described.

There is a need for improved devices for generating nerve-stimulating optical signals (and optionally electrical signals, in order to trigger a nerve action potential (NAP) using a lower amount of optical-signal power than would be needed using optical stimulation alone) and for delivering the optical signals (and optionally electrical signals) to specific tissue locations in a person for the purpose of triggering desired nerve action potentials and/or inhibiting undesired nerve action potentials. There is also a need for detailed designs for an optical-signal-based (e.g., in some embodiments, laser-based) cochlear-implant system in order to restore a sense of hearing in individuals with severely impaired hearing, or with an absence of hearing altogether. There is a need for efficacious apparatus and methods for optically, or optically and electrically, stimulating auditory nerve and/or brain tissue in a living animal in order to generate a nerve action potential (NAP) in one neuron (nerve cell), or in a plurality of neurons within a nerve bundle or nerve (where the combined individual NAPs form a compound nerve action potential, or CNAP), or similar physiological response in the animal. Optical or electrical-and-optical stimulation of neurons can provide more precision in terms of stimulating a particular nerve pathway than is possible using only electrical stimulation. In some embodiments, there is a need to dissipate and spread out the heat energy from the optical laser sources and the electrical driving circuitry.

BRIEF SUMMARY OF THE INVENTION

In some embodiments, the present invention provides an apparatus and a method for optically, or optically and electrically, stimulating neurons (e.g., auditory neurons, and in particular cells in the spiral ganglion) within the cochlea to treat deafness or other hearing loss. In some such embodiments, the apparatus includes a cochlear implant is placed within the cochlea and emits light inside the cochlea from a plurality of independently controlled light emitters (e.g., in some embodiments, vertical-cavity surface-emitting lasers (VC- SELs)) that are deployed along a curled substrate surgically placed within the cochlea. In other embodiments, the apparatus includes an implant that is placed outside but immediately adjacent the cochlea and emits light that penetrated into the cochlea from a plurality of independently controlled light emitters (e.g., in some embodiments, VCSELs) that are deployed along a substrate surgically placed against the outside of the cochlea. In some embodiments, one or more electrodes are placed inside or adjacent the cochlea to provide a sensitizing stimulation signal that, by itself, would not be sufficient to, with high probability, trigger a NAP, but when combined with an optical stimulation signal applied in temporal proximity, enhances the probability of triggering a desired NAP.

In some other embodiments, the present invention provides an apparatus and a method for optically, or optically and electrically, stimulating neurons (e.g., auditory neurons) in the brainstem or midbrain (e.g., central auditory system) and/or brain tissue of a living animal (e.g., a human) to obtain a physiological response in the animal (e.g., a sense of hearing). In some embodiments, the simultaneous application of both an optical stimulation signal and an electrical stimulation signal provides more efficacious generation of NAP responses in the animal than either optical or electrical stimulation alone. In addition, the much higher precision possible when using optical stimulation permits many more channels of cochlear nerve pathways (also called auditory nerve pathways) to be individually and distinctly stimulated than is possible using electrical stimulation alone. In some embodiments, the application of an electrical field before or during the application of the optical stimulation pulse permits more reliable generation of nerve-action-potential signals than is possible using the optical signal pulse alone, and permits reliable generation of NAP signals.

In some embodiments, the present invention includes an audio-signal analyzer (such as a digital-signal-processor (DSP) chip or a microprocessor that performs spectral analysis (e.g., using a fast Fourier transform (FFT), discrete cosine transform (DCT), or other suitable digital-signal-processing means), or a set of frequency filters or other analog circuitry, or the like) that receives an audio signal (e.g., in some embodiments, the "audio signal" includes an electrical signal representative of a sound, pressure or sound signal that was sensed by a microphone or other pressure sensor, and optionally pre-amplified to a usable signal strength) and that outputs a plurality of analyzed-audio (AA) signals that are based on the frequency and loudness content of the audio signal. In some embodiments, the AA signals include a plurality of narrow-band frequency-filtered signals, wherein the amplitude of each represents the magnitude of the spectrum of the audio signal at each of a plurality of frequencies. In some embodiments, the AA signals are used to generate stimulation-control signals that control the electrical and optical stimulation pulses. In some embodiments, the AA signals further include one or more signals that represent certain broadband content of the audio signal (e.g., that a plurality (or a particular set) of the frequency bands each contain spectral content, such as when a three (or more)-part harmony is sensed, or a dissonance, or a sudden impulse (such as a snare drum or gun shot), or white noise is sensed). In some embodiments, when a first set of broadband content is sensed, a threshold-level electrical-stimulation signal is activated to simultaneously (or sequentially in a very short time period) trigger NAPs in a plurality of audio-nerve pathways. In some embodiments, such an arrangement saves power relative to using electrical and optical signals to trigger the NAPs individually in each the plurality of audio-nerve pathways. In other words, when certain types of broadband audio content are detected (e.g., when the audio analyzer determines that there is content in five frequency channels (e.g., f50, f75, f100, f400, and f500)), rather than sending a sub-threshold electrical signal and then activating sub-threshold optical signals to each one of the plurality of different frequency channels f50, f75, f100, f400, and f500 (i.e., optical signals directed to triggering NAPs in the audio-nerve pathways for 50 Hz, 75 Hz, 100 Hz, 400 Hz and 500 Hz), the system instead activates an electrical signal that triggers NAPs in a large number of audio-nerve pathways. In some embodiments, this saves electrical power because the electrical signal takes less power than the multiplicity of optical emitters (e.g., VCSELs). In some embodiments, this also enhances the perceived audio content (perhaps more quickly alerting the patient to danger, or providing the sensation of particular harmonic content). In some embodiments, optical stimulation pulses are also provided at short repeated intervals (called "spikes") shortly after the threshold-level electrical stimulation signal, delivered to certain frequency-specific audio-nerve pathways in order to enhance the delivery of particular frequency information.

As noted above, the auditory nerve pathways extend from spiral ganglion nerves in the organ of Corti of the cochlea to the cochlear nucleus of the brainstem, midbrain and then to the auditory cortex. It is believed that various amounts and kinds of physiological processing of the audio information take place in various parts of the nerve pathways between the cochlea and the auditory cortex. In the portions of the auditory nerve pathways that are closer to the auditory cortex, the NAPs represent this physiologically early-processed audio information. Accordingly, in some embodiments, the present invention includes electronically pre-processing the frequency and intensity information derived from the received audio signal (the signal from the microphone) to obtain information corresponding to the physiologically early-processed audio information that would have been present in a normally hearing person, and applying optical and/or electrical stimulation that represents this pre-processed information to those portions of the auditory nerve pathways (e.g., in the brainstem or midbrain) that are closer to the auditory cortex.

Thus, some embodiments selectively use electrical-only stimulation to represent broadband content of an audio signal, and electrical-optical stimulation to trigger NAPs that produce a sensation to the patient that reproduces narrow-band content (e.g., the sensation of hearing one or more particular audio frequencies, for example a single sine-wave tone, a set of harmonic frequencies, or the like). Some such embodiments use electrical sources where appropriate for widespread stimulation (to simultaneously trigger NAPs in a plurality of audio frequency channels for hearing sensation) and utilize supplemental optical stimulation sources for the frequency-specific "spikes" in the hearing sensation. This allows for power-supply savings by limiting or reducing the use of the optical sources for stimulation of all the different frequencies of broadband signals, and provides better replication of the audio-signal content by using the characteristics of both electrical stimulation (stimulation of many NAPs in many nerves in the vicinity of the electrical source) and optical stimulation (targeted stimulation of one or just a few selected nerve pathways). The electrical and optical stimulation sources are connected to the signal processor whose input comes from an acoustic detector (e.g., microphone) device typically used for conventional electrical-stimulation-only cochlear implants. The device of the present invention processes the acoustic information and separates the signals into two or more groups with at least a first group having one or more signals representative of broadband characteristics, and a second group having a plurality of signals each representing different narrow-band characteristics. The device of the present invention then selectively activates the electrical and optical sources based on the broadband and narrow-band groups.

One purpose of the present nerve-pathway (e.g., neurons in the cochlea, cochlear nerve, auditory-brainstem and/or -midbrain) optical stimulator or hybrid stimulator (wherein the hybrid stimulator uses both optical and electrical stimulation) is to provide auditory sensations for patients who are otherwise deaf (and who are not, or may not be, candidates for cochlear implants due to injured or absent auditory nerves, for example, patients with neurofibromatosis type 2, cochlear ossification and/or labyrinthitis ossificans, severe cochlear hypoplasia, traumatic bilateral auditory nerve injury and the like). Another use of some embodiments of the present invention is to provide an apparatus and method for conducting basic and clinical research on how to improve the performance of auditory brainstem implants (ABIs)) using infrared laser technology, optionally also using simultaneous electrical stimulation. The optical auditory-brainstem or -midbrain stimulator can also be used as a powerful research tool to stimulate discrete regions and neuronal populations without the concerns of shock artifact, a phenomenon that is inherent to electrical-stimulation paradigms.

In some embodiments, the present invention provides apparatus and methods for optical stimulation or optical-and-electrical stimulation of auditory nerve pathways and/or brain tissue. Peripheral neural stimulation using infrared lasers has been demonstrated in several systems; however, to the inventors' knowledge, optical stimulation of the central nervous system (CNS) has not been previously described. In some embodiments of the present invention, radiant energy exposure of the cochlear nucleus using a mid-wavelength infrared laser generates optically-evoked auditory brainstem responses (oABRs). In one experiment, the cochlear nuclei of adult male Sprague-Dawley rats were exposed using a suboccipital craniotomy approach. Different regions of left cochlear nucleus were acutely stimulated, using a 200- or 400-μm-diameter (depending on the embodiment) optical fiber placed on the surface of the brainstem, with 50-μs to 750-μs pulses of 1849-nm-wavelength to 1865-nm-wavelength radiation at a rate of 10 Hz to 40 Hz and power levels ranging from 10% to 80% of a 5-W maximum power. oABRs were recorded during the period of optical stimulation. Post-experiment histology was performed to assess the extent of any tissue damage to the brainstem.

oABRs were observed during surface exposure of the cochlear nucleus to infrared radiation. Reproducible oABRs were seen at radiant energy levels (1849 nm) as low as 30% of a 5-W maximum power (i.e., 1.5 watts), with a 150-μs pulse width, and 10-Hz pulse repetition rate. No thermal tissue damage was seen in the cochlear nucleus following these acute experiments when pulse widths were less than 1 ms and power levels did not exceed 80% of a 5-W maximum power (i.e., 4 watts).

In other embodiments, the present invention provides apparatus and methods for optical stimulation or optical-and-electrical stimulation of nerve pathways and/or brain tissue of sensory modalities other than audition. In some such embodiments, apparatus and methods are provided for optical stimulation or optical-and-electrical stimulation of nerve pathways and/or brain tissue involved in vision. In other such embodiments, apparatus and methods are provided for optical- or optical-and-electrical stimulation of nerve pathways and/or brain tissue involved in olfaction. In other such embodiments, apparatus and methods are provided for optical- or optical-and-electrical stimulation of nerve pathways and/or brain tissue involved in balance. In other such embodiments, apparatus and methods are provided for optical- or optical-and-electrical stimulation of nerve pathways and/or brain tissue involved in tactile sense. In other such embodiments, apparatus and methods are provided for optical- or optical-and-electrical stimulation of nerve pathways and/or brain tissue involved in taste.

In some embodiments, one or more of the apparatus as described in the related provisional patent applications, patent applications and/or patents incorporated by reference above (e.g., 60/715,884, 60/826,538, 60/872,930, 60/884,619, 60/885,879, 60/964,634, 61/015,665, 61/102,811, 61/147,073, 11/257,793, 11/536,639, 11/948,912, 11/536,642, 11/971,874, 12/018,185, 12/191,301, 12/505,462, 12/573,848, and 12/693,427) are used to generate and/or deliver the optical-stimulation signals and optionally the electrical-stimulation signals that are delivered to the brainstem or the midbrain of the patient using methods and apparatus of the present invention.

This is the first known description of optical stimulation of the CNS in an in vivo model. Mid-wavelength infrared lasers are capable of generating oABRs during acute stimulation of the cochlear nucleus without tissue damage and may provide the basis for novel auditory brainstem implant stimulation paradigms in the future.

As used herein, an "optrode" is the light-emitting end from which a light signal is emitted to assist in, or by itself cause, stimulation of a nerve action potential (NAP). Similarly (and as conventionally used), an "electrode" is an end of a conductor through which an electrical signal is transmitted to assist in, or by itself cause, stimulation of a nerve action potential (NAP). In some embodiments, an optrode is the light-emitting end of an optical fiber or similar waveguide that couples light from a light source (such as a laser, particularly a vertical-cavity surface-emitting laser (VCSEL), or light-emitting diode (LED) or the like) connected to an electrical controller (e.g., an implanted battery-operated device) to a location at a distance from the controller (i.e., the light is coupled from where it is generated in or near the controller to the nerve to be stimulated, which is at a distance from the controller), while in other embodiments, the VCSEL is located proximate to the nerve to be stimulated, and is electrically coupled to the distal controller (i.e., the electrical signal is coupled from the controller to a VCSEL located proximate to the nerve to be stimulated, wherein the VCSEL and the nerve are at a distance from the controller).

In some embodiments, a sub-threshold optical signal is emitted from an optrode (wherein the optical signal by itself has a low probability of triggering a NAP), and at approximately the same time or slightly before, a sub-threshold electrical signal is applied from an electrode (wherein the electrical signal by itself has a low probability of triggering a NAP), but that such signals applied together in time are sufficient to have a high probability of triggering a NAP. In some embodiments, a plurality of the optical-stimulation optrodes are associated with each of one or more electrical-stimulation electrodes (e.g., in some embodiments, a plurality of separately and independently activatable electrodes are provided, wherein each one of the plurality of electrodes has a plurality of associated optrodes).

In some embodiments, a ring electrode is provided, wherein one or more optrodes are within the ring. In some such embodiments, the ring electrode also serves as one of the electrical connections to one or more VCSELs that serve as the optrodes. In some such embodiments, the electrical-stimulation signal (which is started slightly earlier than the optical signal activation) serves as at least part of the bias used to activate the VCSEL so it can emit light. See FIGS. 25A-25E, which show optical and electrical sources adjacent to each other, wherein optionally all optrodes are paired with an electrode, and all electrodes are paired with an optrode and optionally additional optrodes added between the pairs.

In some embodiments, the controller is reprogrammable to compensate for movement of the optrodes and electrodes relative to the nerves to be stimulated. For example, if some time (days, weeks or years) after the device is implanted, the patient thinks that the hearing restoration is not as it should be, she can return to the hearing specialist, who then causes a series of test signals to be applied through the implanted device and either through a response reported by the patient or by some other measurement of a physiological response, the various frequencies or other hearing parameters that are evoked by each of a plurality of optical and/or electrical signals is mapped and the map stored in a memory device. The map is then used to assist in performing the conversion of a sound signal (received by a microphone) to the proper corresponding optical and electrical stimulation signals that trigger the appropriate NAPs in the appropriate nerves.

In some embodiments, a heat spreader is provided that thermally couples a first region having a relatively lower density of optical emitters to a second region having a relatively higher density of optical emitters, in order to even out the heat load between the two regions.

BRIEF DESCRIPTION OF THE DRAWINGS

FIG. 1A is a generic block diagram of implantable or partially implantable functional elements for an electrical-optical nerve-stimulator-implant system 100.

FIG. 1B is a more-detailed block diagram of an implantable or partially implantable system 100.

FIG. 5A is a block diagram of a VCSEL-based system 500 for insertion into the scala tympani.

FIG. 5B is a schematic diagram of VCSEL-based system 500 inserted into the scala tympani.

FIG. 6A is a block diagram of an implant system 600 for insertion into the cochlea for stimulating nerve cells with light according to one embodiment of the invention.

FIG. 6B is a schematic diagram of implant system 600 that has been inserted into the cochlea for stimulating nerve cells with light according to one embodiment of the invention.

FIG. 7A is a block diagram of an implant system 700 for insertion into the cochlea for stimulating nerve cells with light according to another embodiment of the invention.

FIG. 7B is a schematic diagram of implant system 700 that has been inserted into the cochlea for stimulating nerve cells with light according to one embodiment of the invention.

FIG. 8A is a block diagram of a system 800 for resting outside the cochlea for stimulating nerve cells with light according to one embodiment of the invention.

FIG. 8B is a schematic diagram of a system 800 that is resting outside the cochlea for stimulating nerve cells with light according to one embodiment of the invention.

FIGS. 10A, 10B, and 10C are diagrams of 3D VCSEL-array system 1000A, 1000B, and 1000C, respectively, resting outside the cochlea for stimulating nerve cells with light according to another embodiment of the invention.

FIGS. 11A, 11B, and 11C are diagrams of system 1100A, 1100B, and 1100C, respectively, implanted and resting outside the cochlea for stimulating nerve cells with light that propagates through bone according to another embodiment of the invention.

FIG. 16A is a side view of a stimulation system 1600.

FIG. 16B is a perspective cross-section view of stimulation system 1600.

FIG. 23A is a perspective-view schematic diagram of a single fiber ribbon 2300 according to some embodiments of the present invention.

FIG. 23B is a side-view schematic diagram of single fiber ribbon 2300 according to some embodiments of the present invention.

FIG. 24A is a perspective-view schematic diagram of a fiber ribbon assembly 2410 having a plurality of fiber ribbons 2300 according to some embodiments of the present invention.

FIG. 24B is a plan-view schematic diagram of a VCSEL-array assembly 2420 having a plurality of VCSELs 2421 according to some embodiments of the present invention.

FIG. 24C is a plan-view schematic diagram of a VCSEL-ribbon-fiber array assembly 2400 having a fiber ribbon assembly 2410 and a VCSEL-array assembly 2420 according to some embodiments of the present invention.

FIG. 25A is a perspective-view schematic diagram of a subsystem 2501 according to some embodiments of the present invention.

FIG. 25B is a perspective-view schematic diagram of a subsystem 2502 according to some embodiments of the present invention.

FIG. 25C is a perspective-view schematic diagram of a subsystem 2503 according to some embodiments of the present invention.

FIG. 25D is a perspective-view schematic diagram of a subsystem 2504 according to some embodiments of the present invention.

FIG. 33 is a flow diagram of methods of substrate-level packaging 3000 according to some embodiments of the present invention.

FIG. 37 is a block diagram of leak testing system 3700, according to some embodiments of the present invention.

FIG. 38 is a stimulation system 3800 configured to be implanted within the cochlea of a living subject (e.g., a human) according to some embodiments of the present invention.

FIG. 39 is a diagram of methods 3900 to physically secure an implant to the cochlea according to some embodiments of the present invention.

DETAILED DESCRIPTION OF THE INVENTION

Figure 2A:
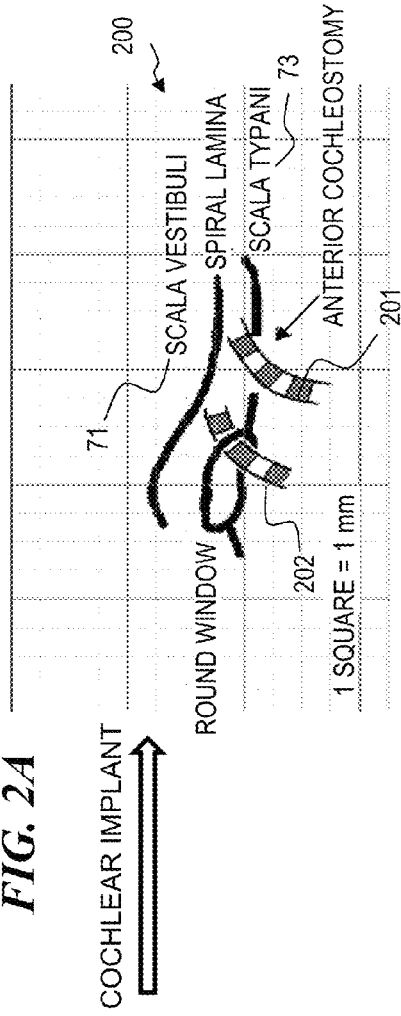
FIG. 2A is a block diagram of the general nerve-stimulation-implant method 200 concept, according to some embodiments.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon, the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In some embodiments, the present invention uses a light-propagating transmission medium to carry optical signals between a light source and the tissue (e.g., neurons) of the patient, in order to stimulate a nerve action potential. In some embodiments, the light source includes a VCSEL that outputs its light directly onto the tissue being stimulated. In some similar embodiments, a focussing element (such as a lens or graded-index (GRIN) fiber) is placed in the light path between the VCSEL output and the tissue (e.g., in some embodiments, such a focussing element placed directly against or very close to the VCSEL) to focus and/or guide more effectively to a particular destination (e.g., one or more cells of a spiral ganglion). In some embodiments, the transmission medium includes one or more optical fibers (e.g., a bundle of optical fibers, each of which includes a waveguide (e.g., the core of the fiber, which has a higher index of refraction than the cladding). In some embodiments, the light-propagating medium includes a plurality of side-by-side longitudinal (parallel-like) waveguides formed in an optical fiber or optical "ribbon". In some embodiments, a planar substrate is used, wherein the planar substrate includes a plurality of waveguides, and optionally includes other optical components such as filters, evanescent couplers, optical-fiber interfaces, selective gates that control the amplitude of light output, focusing elements, light-output ports (e.g., gratings that allow light to exit the waveguides toward the tissues of interest) and the like. In some embodiments, a tapered silicon substrate is used, the substrate having a plurality of waveguides formed by three-dimensional (3D) etching at the light-output tip (and optionally also at an input interface that receives light (e.g., from a plurality of optical fibers).

In some embodiments, the output end of such an optical element is called a "probe" and allows a large number of light-output ports, such that after implantation inside the cochlea, outside but adjacent the cochlea, adjacent the auditory nerve leaving the cochlea, or adjacent to the brainstem or midbrain of the patient, individual ones of the output ports are individually activatable to determine which ports stimulate which nerve pathways. A mapping of which port is coupling light to which nerve pathway is then programmed into the controller that drives a particular optical signal to the desired nerve pathway to be stimulated. Because there are many more light-output ports than nerve destinations utilized by the device for processing of the audio content, the implanted device can be programmed to send the appropriate signals to each of a plurality of nerve pathways, greatly simplifying placement of the output probe (as compared to having to individually place each of a plurality of separate fibers). Further, at a later time, the implanted device can be recalibrated, remapped and reprogrammed to compensate for movement of the probe relative to the tissue to be stimulated. In addition, refinements based on later-discovered principles can be reprogrammed into the implanted device to provide a better sense of hearing for audio implants. Of course, other embodiments include implanted devices that provide other sensations, such as vision, olfaction, touch (some embodiments including sexual sensations), temperature, pressure, and the like.

There are at least ten patents and patent applications (included in the list of related patent applications set forth above) that are assigned to Lockheed Martin Corporation that describe various apparatus, including the fundamental devices, as well as methods of making, methods of using, specific applications for use, and key system subcomponents to commercialize this technology. Two specific patent applications are related to this disclosure: the first one, U.S. patent application Ser. No. 11/971,874 titled "Method and Vestibular Implant using Optical Stimulation of Nerves" (which issued as U.S. Pat. No. 8,012,189 on Sep. 6, 2011), describes the use of infrared nerve stimulation for cochlear implants, and the second, U.S. patent application Ser. No. 12/191,301 titled "VCSEL Array Stimulator Apparatus and Method for Light Stimulation of Bodily Tissues" (which issued as U.S. Pat. No. 8,475,506 on Jul. 2, 2013), describes the use of vertical-cavity surface-emitting lasers (VCSELs) for implantable neuro-stimulation systems, including cochlear implants. Each of these patent applications is incorporated herein by reference. Various embodiments of the present invention set forth novel design permutations of a practical cochlear-implant system using a combination of electrical and laser technology to stimulate nerves, and the details of system subcomponents, as well as surgical approaches for how these devices are implanted and used in a practical manner in people.

In some embodiments, the laser sources and optical delivery waveguides and tissue interfaces of present invention use connections to an implanted sound sensor and controller (such as an existing cochlear-implant device (which includes microphone(s), power supply, audio processor and the like)), but replaces the conventional electric stimulator portion with an optical (e.g., laser)-stimulation system to provide higher-precision stimulation to smaller subsets of the excitable tissues in the cochlea (e.g., in some embodiments, providing precision stimulation of hair cells and/or spiral-ganglion cells). In some embodiments this allows for improved performance (a higher-quality hearing sensation for the user) in existing cochlear implants by allowing greater hearing fidelity in noisy environments and more frequency bands for improved speech intelligibility. The present invention utilizes three unique approaches for the practical implementation of these systems: (1) implanting the VCSELs directly into the cochlea in a sealed package, (2) using waveguides to shine individual lasers to specific sites within the cochlea, or (3) using a gratings approach to use a single source outside the cochlea to stimulate multiple points within the cochlea. Each of these various embodiments of the present invention has multiple permutations and different subcomponents, which are described in detail below and in the accompanying figures.

Neural prosthetic devices are artificial extensions of the body that restore or supplement nervous-system functions that were lost due to disease or injury. Particular success has been realized in the cochlear-prostheses development (which is approximately a $500-million market, with a 25% compound-growth rate (CGR) predicted over the next decade, and an estimated 3% total market penetration to date). Certain conventional cochlear-implant devices bypass damaged hair cells in the auditory system by instead providing coarse direct electrical stimulation of the auditory nerve. The cochlear implants stimulate discrete spiral ganglion cell populations in the user's ears, which is similar to the encoding of small acoustic frequency bands in a normal-hearing person's ear. However, for closely spaced electrode pairs at required current levels, a broad region of auditory neurons is activated. Consequently, overlapping electric fields (channel cross-talk) leads to confused sound sensation encoded via these few electrode contacts. Consequently, stimulation of spatially discrete spiral ganglion cell populations is difficult and only few independent "channels" are possibly available to encode acoustic information into action potentials on the auditory nerve. This fundamental limitation reduces the number of independent channels that can be conveyed to the cochlear implant user.

Currently, a conventional implanted 16-channel electrode can be used to provide pulsed current stimulation of excitable cells in the cochlea. The discrete coarse functional channels available with this type of implant are unable to provide true hearing restoration for existing cochlear-implant users. These devices could be improved by combination with the present invention to allow for enhanced hearing intelligibility in noisy environments, hearing of music, or hearing of multiple voices in speech.

Infrared nerve stimulation (INS) may dramatically improve the function of auditory prosthetics. The number of frequency bands required to transmit speech information accurately is an important measurement used in the optimization of multiple-electrode cochlear stimulation. Previous work with cochlear implants demonstrated that speech-recognition scores increase with the number of electrodes. The use of laser light to stimulate spiral-ganglion cells enables a more precise stimulation of the auditory system (as experimentally verified by the inventors' collaborators at Northwestern University). Development of these light-based systems can provide high-fidelity cochlear implants by enabling stimulation of an increased number of independent sub-populations of spiral-ganglion cells for speech processing.

The present invention relates to laser stimulation of animal tissues and more particularly to lasers and methods for making and using devices that generate optical signals, and optionally also electrical signals in combination with the optical signals, to stimulate and/or simulate an auditory signal in nerve and/or brain tissue of a living animal (e.g., a human) to treat deafness or hearing loss and provide sensations related to hearing, and/or to stimulate and/or simulate other "sensory" signals in nerve and/or brain tissue of a living animal (e.g., a human) to treat other sensory deficiencies (e.g., balance, visual or olfactory) and provide sensations related to those sensory deficiencies.

In some embodiments, the light signal used to stimulate a nerve action potential includes wavelengths in the range of 1800 nm to 2100 nm, and in some particular embodiments wavelengths between 1830 nm and 1870 nm. In other embodiments, the stimulation light signal includes wavelengths in the range of 1400 nm to 1500 nm, the range of 1500 nm to 1600 nm, or other suitable light wavelength in the range of 300 nm to 10,000 nm.

FIG. 1A is a generic block diagram of an implantable or partially implantable system 100 that uses both electrical stimulation and light stimulation of neuronal tissue in the brainstem and/or midbrain nerves such as the auditory brainstem to obtain an auditory brainstem response (ABR) for patient 99. In some embodiments, system 100 includes an external portion 130 and an implanted portion 120 that is within patient 99.

FIG. 1B is a more-detailed block diagram of an implantable or partially implantable system 100 (according to some embodiments of the present invention) that uses both electrical stimulation and a VCSEL (vertical-cavity surface-emitting laser) array for light stimulation of neuronal tissue 98 in the cochlea, in the cochlear nerve (also called the auditory nerve) and/or in the brainstem and/or midbrain nerves such as the auditory brainstem to obtain an auditory brainstem response (ABR) (e.g., some embodiments use a VCSEL array such as described by U.S. Provisional Patent Application No. 60/964,634 filed Aug. 13, 2007, titled "VCSEL Array Stimulator Apparatus and Method for Light Stimulation of Bodily Tissues"). System 100 represents one embodiment of the present invention, wherein an external portion 130 (located outside the body of the user) receives sound signals with a microphone 141 that generates an analog electrical signal 142, preamplifies the analog signal with preamplifier 143 and converts the pre-amplified analog signal 144 to a digital signal 146 using an analog-to-digital converter (ADC) 145, performs digital signal processing using a digital signal processor (DSP) 147 on the digital signal 146 to obtain processed digital information 148, modulates an RF (radio-frequency) signal with the processed digital information using modulator 149, to obtain a modulated RF signal 150, power amplifies the modulated RF signal using power amplifier 151 and transmits that power-amplified modulated RF signal 152 from an antenna or transmitting coil 153 outside the body of patient or user 99 to an internal receiving antenna (e.g., a receiving coil) 161 that is part of circuitry 120 that is implanted within the body of user 99. In some embodiments, circuitry 120 receives the modulated RF signal using its receiving coil 161, and uses much of the received RF signal 162 to power the rest of circuitry 120 (e.g., by rectifying the RF signal 162 to a DC voltage 164 and then regulating that DC voltage using rectifier-and-regulator unit 163 to obtain energy (from DC voltage 164) to power the circuitry 120 and/or recharge any internal battery source). In some embodiments, a demodulator 165 is used to demodulate the RF signal to retrieve the already processed digital information 166, then a decoder-DAC 167 decodes and optionally converts the digital result 166 to analog 168 (called digital-analog conversion (DAC)), uses that resulting analog signal 168 to generate pulse information or data (e.g., in some embodiments, generating bi-phasic pulses 170 having both a positive excursion and a negative excursion using bi-phasic pulse generator 169), which are de-multiplexed using demultiplexor 171 and used to drive the electrical-current drivers 175 (for electrical-stimulation pulses 116 to the electrodes) that electrically stimulate or pre-condition the neuron(s) for triggering a NAP. In some embodiments, demultiplexor 171 also drives one or more laser drivers 113 (to drive the lasers 112 that output optical-stimulation signals 111 (delivered by any suitable optical delivery means, such as optical delivery means 400 described in FIG. 4 below) which combine with the electrical stimulation 116 to trigger the desired fine-grain precise NAPs for the desired sensory response for user 99).

In some embodiments, electrical preconditioning/stimulation from the electrical-stimulation portion (through the electrical current sources 175 in the upper-right-hand corner of implant 120 of FIG. 1B) applies electrical current 116 to the nerve tissue to be stimulated using an electrode array (in some embodiments, the electrical signal 116 is sub-threshold relative to triggering a NAP in the neuron(s), meaning that when applied by itself, it has a low probability of triggering a NAP), and a low-power, low-lasing-threshold (i.e., efficient diode lasers having a low threshold for lasing (i.e., requiring little electrical current to initiate lasing)) VCSEL array 112 (in the lower-right-hand portion of FIG. 1) is selectively activated by electrical current from drivers 113. The VCSEL array selectively emits laser light from each of a plurality of VCSELs 112, for example VCSELs implemented as an array of separately activatable lasers formed in a monolithic semiconductor chip, in order that the optical energy combines with the electrical preconditioning to trigger NAPs with fine-grained and precise accuracy not available if using electrode stimulation alone, and with lower optical power than if using optical stimulation alone. The lower-power optical output provides at least some of the following advantages: it reduces the power needed from the battery, it reduces the amount of heat generated by the VCSEL or other optical source, and it reduces the possibility of tissue damage from the optical signal.

In some embodiments, each laser beam is separately controlled by laser-and-power controller 113 that drives the laser-diode VCSELs under control of a processor or circuitry 109 that generates combined electrical signals 116 and optical signals 111 that are configured to stimulate the nerve tissue as desired. For example, in some embodiments, the light signals 111 are collimated, focused and/or guided by optics 103 (e.g., a lens or other suitable optical device; see FIG. 3) within device enclosure 110 into delivery medium 107 (e.g., a bundle of optical fibers), which extends from the enclosure 110 to a remote location such as in the cochlea, cochlear nerve, brainstem or midbrain (any one or more of which can comprise the appropriate neuronal tissue 98 of the desired auditory nerve pathways) of patient 99. In some embodiments, the system includes an internal transmitter/receiver 180 that obtains data and power signals 181; e.g., in some embodiments, wirelessly using RF signals to and from an external transmitter/receiver 130, and that optionally sends data (on signals 181) to external transmitter/receiver 130. In some embodiments, the data received by internal transmitter/receiver 180 includes instructions that program and map the relationship between sensed signals and the desired NAPs to be stimulated, and the data sent by internal transmitter/receiver 180 includes data that is usable for diagnostics and for testing (e.g., to determine the proper mapping between analyzed audio signals and the particular ones of the auditory nerve pathways to be stimulated to obtain the desired auditory sensation by the person having the implant (and, accordingly, the optical emitters and electrodes to activate to trigger NAPs in those auditory nerve pathways).

In some embodiments, the system also uses a visible laser and/or LED array that are selectively activated to produce visible light signals to help align the VCSEL laser array signals 111 with optics (e.g., the lens array/beam coupler/combiner optics) 103 during the implantation surgery, and/or to indicate where the IR signals are being emitted from the far end of delivery medium 136 to help the surgeon align the distal tip of the delivery medium 136 to the appropriate neuronal tissue during the implantation procedure. In some embodiments, one or more sensors are used to obtain the above-described audio information, balance or orientation information, temperature information, and/or other information that is to be converted to nerve-stimulation signals (e.g., optical signals and optionally also electrical signals) to deliver to patient 99 via stimulation of NAPs in the cochlea, the cochlear nerve, and/or through the patient's brainstem or midbrain neurons 98. In some embodiments, the sensors are implanted inside the patient 99. In other embodiments one or more sensors are part of an external unit 130 that is wirelessly coupled to the implanted device 120.

In some embodiments, electrical nerve-stimulation signals 116 are generated by stimulation-calculation processor or circuitry 109, and are delivered to the stimulation site using a series of spaced electrodes (e.g., a bundle having a plurality of electrical conductors and a plurality of optical fibers), such as described in U.S. patent application Ser. No. 12/018,185 filed Jan. 22, 2008, titled "Hybrid Optical-Electrical Probes" (which issued as U.S. Pat. No. 7,883,536 on Feb. 8, 2011), U.S. patent application Ser. No. 12/191,301 filed Aug. 13, 2008, titled "VCSEL Array Stimulator Apparatus and Method for Light Stimulation of Bodily Tissues" (which issued as U.S. Pat. No. 8,475,506 on Jul. 2, 2013), and U.S. patent application Ser. No. 12/573,848 filed Oct. 5, 2009, titled "Nerve Stimulator and Method using Simultaneous Electrical and Optical Signals" (which issued as U.S. Pat. No. 8,160,696 on Apr. 17, 2012), each of which is incorporated herein by reference in its entirety.

In some embodiments, the electrical signals 116 are used to sensitize the neuronal tissue 98 (as opposed to being sufficient to trigger a nerve action potential using only the electrical signal) in order that a lower-power optical stimulation signal is sufficient to trigger the desired nerve action potential (NAP) in one or more neurons via stimulation of NAPs in the cochlea, the cochlear nerve, and/or in the brainstem or midbrain of the patient.

In some embodiments, the optical (and optional electrical) signals are delivered and directed upon the auditory brainstem nerves, i.e., Cranial Nerve VIII (the cranial nerve for hearing and balance), or other brainstem or midbrain tissue 98 of a patient 99. In some embodiments, some or all of system 100 is implanted within patient 99. In some embodiments, the end of delivery medium that is distal to optics (e.g., beam combiner) 103 includes a plurality of optical fibers that are configured to output light in a plurality of different locations and/or different directions from a single location. In some embodiments, the optical-electrical delivery medium (e.g., beam combiner 809 and waveguide unit 807 of FIG. 8) also includes a plurality of electrical conductors that are configured to output electrical signals in a plurality of different locations (e.g., to one or more of those locations at any one time (e.g., from a point-type exposed electrode to a general ground voltage) and/or different directions (e.g., to one or more of those directions at any one time) from a single location. In some embodiments, the electrical signals are used to precondition the neurons to be stimulated such that a lower-intensity optical signal can be used to trigger the desired nerve-action-potential pulse.

In some embodiments, the optical (and optional electrical) signals are delivered and directed upon other brainstem nerves, for instance, Cranial Nerve II (the cranial nerve for vision), Cranial Nerve I (the cranial nerve for olfaction), or the like. In some such embodiments, suitable external sensors 108 (or internal sensors 108' for sensing environmental parameters that are external to the person) for the necessary input data (sensors such as, for example, microphones, pressure sensors, vibration sensors, gyroscopes, accelerometers, gravity-direction sensors, electromagnetic-radiation sensors such as imaging devices, light sensors and color sensors, chemical sensors (i.e., for odors and/or taste), and the like) are used to obtain data that can be used to generate the stimulation signals (optical and/or electrical) of device 300 (referring to FIG. 3) used to trigger NAPS in the nerve pathways of person 99. In some such embodiments, the data from such external sensors 108 are transmitted in signals 181.

Thus, in some embodiments, an imaging device is used as a sensor (or as part of an external sensor-transmitter 120) to obtain image data, this image data is processed to detect vision aspects of the image data such as patterns (e.g., vertical objects, horizontal objects, diagonal objects, curved objects and the like), color (e.g., hue, saturation, brightness, contrast and the like with regard to various objects and patterns), motion (direction, speed, enlargement, and the like) and the processed image data is used to generate stimulation signals used to drive optical and/or electrical probes that stimulate the midbrain or brainstem portion of Cranial Nerve II (the cranial nerve for vision) in order to provide a simulated vision sensation for the patient. In some embodiments, electromagnetic-radiation sensors that do not generate image data as such, for example light sensors and color sensors, are used to obtain more generic electromagnetic-radiation data from the environment (such as the color of an object), and this generic electromagnetic-radiation data is processed to provide optical- and/or electrical-stimulation signals that stimulate the midbrain or brainstem portion of Cranial Nerve II to provide more fundamental sensations (such as the color of whatever the color sensor is aimed at).

Further, in some embodiments, one or more chemical sensors are used to obtain chemical data (e.g., data relating to gasses or particulates from the atmosphere, or materials such as salts, sugars and the like dissolved in a liquid), this chemical data is processed to detect odor aspects of the chemical data, and the processed odor data is used to generate stimulation signals used to drive optical and/or electrical probes that stimulate the midbrain or brainstem portion of Cranial Nerve I (the cranial nerve for olfaction) in order to provide a simulated smell and/or taste sensation for the patient.

Yet further, in some embodiments, one or more pressure, texture, vibration, weight and/or similar sensors are used to obtain touch-and-feel data, this touch-and-feel data is processed to detect mechanical-touch aspects of an object, and the processed mechanical-touch data is used to generate stimulation signals used to drive optical and/or electrical probes that stimulate the midbrain or brainstem portion of other nerve pathways in order to provide a simulated touch-and-feel sensation for the patient.

Still further, in some embodiments, one or more nerve-action-potential (NAP) sensors are used to obtain nerve-and-movement-disorder data, this nerve-and-movement-disorder data is processed to detect nerve-signal patterns that are indicative of Parkinson's Disease or other movement disorders, and the processed nerve-signal data is used to generate stimulation signals used to drive optical and/or electrical probes that stimulate the midbrain or brainstem portions (such as the red nucleus and substantia nigra) of affected nerve pathways in order to treat or inhibit the movement disorder of the patient.

In some embodiments, the optical-fiber bundle end of device 100 is situated in or along the brainstem (the medulla, pons and/or midbrain), or along the cranial nerves, or even, in some embodiments, in or along side of the higher brain centers such as the cerebral cortex. In some embodiments, at least a portion of the optical-fiber bundle end of device 100 is situated in or along the spinal cord of the patient, further from the brain than the brainstem. In some embodiments, the optical-fiber bundle end of device 100 is situated in or along the limbic system (e.g., thalamus, hypothalamus, amygdala, and/or hippocampus), or the pituitary gland, cerebellum, or corpus callosum.

The human brain has twelve pairs of special nerves called the cranial nerves. These are specific bundles of neurons and axons which transmit special information to and from the brain, without going through the spinal cord. The cranial nerves each provide highly specific functions (sensory or motor). The cranial nerves all exit from the bottom of the brain and brainstem and exit the skull through various foramina to reach their sources or targets. In some embodiments, the optical-fiber-bundle light-delivery (and optionally electrical-stimulation) end of device 120 is situated in or along one or more of the cranial nerves to obtain one or more of the following responses of Table 1:

TABLE 1

| CRANIAL NERVE | NAME | MAIN FUNCTION |
| --- | --- | --- |
| Cranial Nerve I | Olfactory Nerve | Smell |
| Cranial Nerve II | Optic Nerve | Vision |
| Cranial Nerve III | Oculomotor Nerve | Eye movement |
| Cranial Nerve IV | Trochlear Nerve | Eye movement |
| Cranial Nerve V | Trigeminal Nerve | Facial sensation |
| Cranial Nerve VI | Abducens Nerve | Eye movement |
| Cranial Nerve VII | Facial Nerve | Facial movement |
| Cranial Nerve VIII | Auditory Nerve | Hearing and balance |
| Cranial Nerve IX | Glossopharyngeal Nerve | Organs and Taste |
| Cranial Nerve X | Vagus Nerve | Organs and Taste |
| Cranial Nerve XI | Accessory Nerve | Shoulder shrug & head turn |
| Cranial Nerve XII | Hypoglossal Nerve | Tongue movement |

FIG. 2A is a block diagram of the general nerve-stimulation-implant method 200 concept, according to some embodiments. In contrast to conventional electrical techniques that include insertion of the electrode into the cochlea, some embodiments of the present invention include invasive insertion of one or more electro-optical stimulation probes 202 through the round window of the cochlea, or an antero-inferior insertion of one or more electro-optical stimulation probes 201. In other embodiments, the implantation is minimally invasive and does not break the bone-cochlea barrier, but instead applies the electrical and light stimulation signals across tissue boundaries (e.g., implanting the one or more electro-optical stimulation probes in the bone behind the ear and leaving a thin layer of bone through which the electrical and optical signals are applied to the organs of the inner ear or to the nerves that connect those organs to the brain (e.g., in some embodiments, optical signals are transmitted through the round window of the cochlea without requiring invasive insertion of the electro-optical probe through the round window)). In some embodiments, each of the permutations of the present invention will connect to the electronics and sensors of a conventional cochlear implant system except that the electrical signal generator and electrodes of the conventional cochlear implant system are replaced by the laser and electrical driver electronics of the present invention, which drive the fiber-optics-electrode-combination probes (called "optrodes") of the present invention.

Figure 2C:
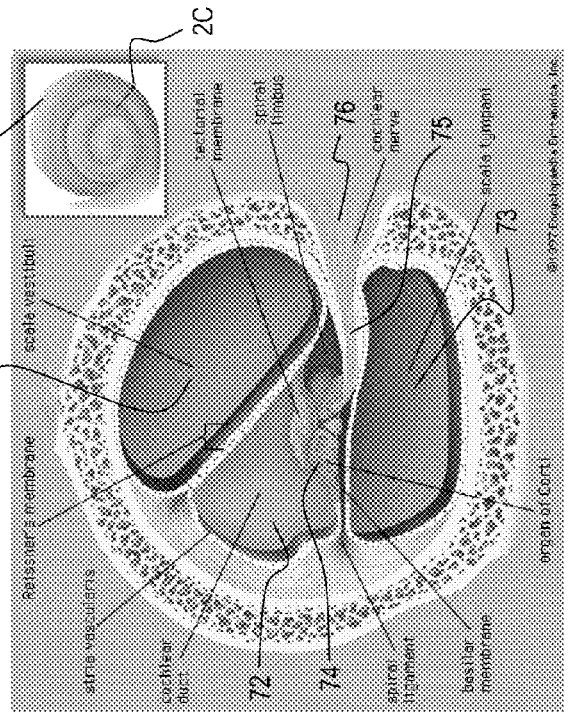
FIG. 2C is a cross-section diagram of the cochlea 78 of the inner ear of a person 99.
Figure 2B:
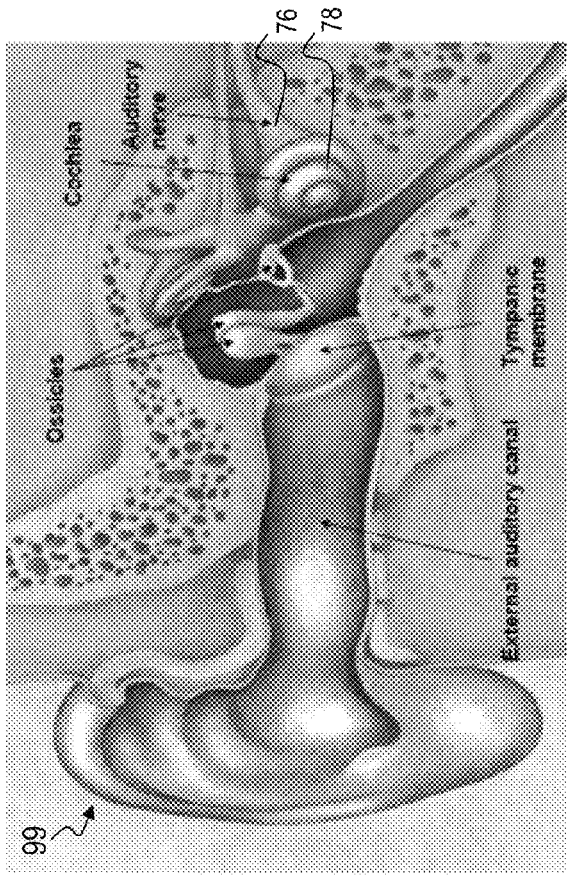
FIG. 2B is a cross-section diagram of the organs of the inner ear of a person 99.

FIG. 2B is a cross-section diagram of the organs of the inner ear of a person 99. Shown is the external auditory canal leading to the tympanic membrane. Sound is transmitted from the tympanic membrane to the cochlea 78 by the ossicles. Nerve action potentials (NAPs) generated by neurons in the cochlea 78 travel through the auditory nerve 76 to the auditory cortex (not shown) via a plurality of auditory nerve pathways (which each carry different information indicative to frequency and intensity in the received sound).

FIG. 2C is a cross-section diagram of the cochlea 78 of the inner ear of a person 99. Cochlea 78 includes three primary fluid-filled channels: the scala vestibuli 71, the cochlear duct 72 and the scale tympani 73. Hair cells in the organ of Corti 74 receive vibrations and generate NAPs in the spiral ganglion cells 75 that extend to or through the cochlear nerve 76. In some embodiments, the device of the present invention delivers light stimulation pulses and/or electrical stimulation pulses to the organ of Corti, the spiral ganglion cells and/or the cochlear nerve in and around the cochlea 78 (the inset box shows the cochlea 78 from the outside and shows the cut line 2C for the representation in the main FIG. 2C). In various embodiments, some or all of the stimulation part(s) of the device of the present invention are implanted and located in the scala tympani 73, the cochlear duct 72, and/or the scala vestibuli 71. In other embodiments, some or all of the stimulation part(s) of the device of the present invention are implanted and located outside the cochlea, e.g., in the bone surrounding the cochlea 78.

Figure 3:
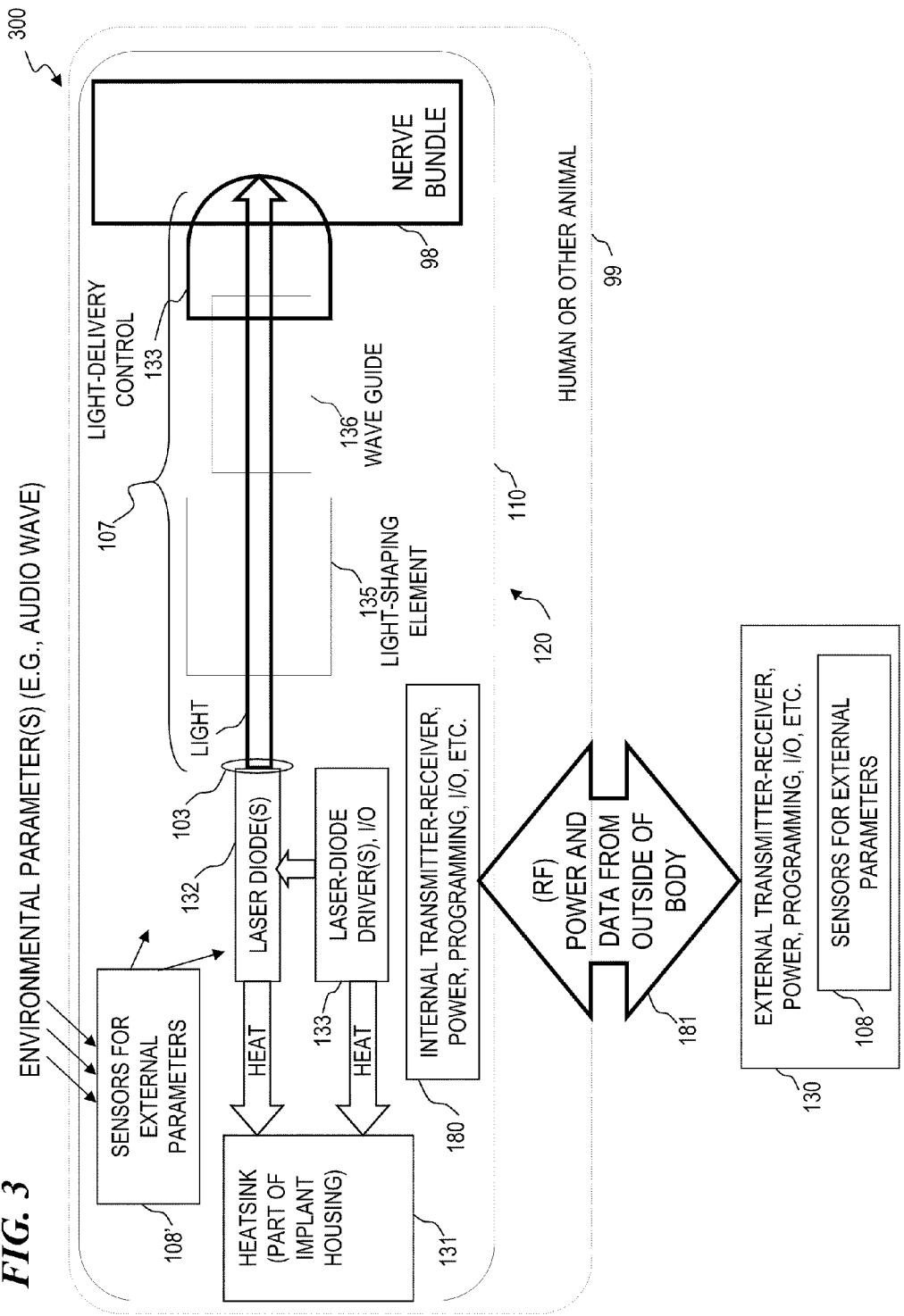
FIG. 3 is a block diagram of general functional elements for a nerve-stimulator-implant system 300.

FIG. 3 is a block diagram of general functional elements for a nerve-stimulator-implant system 300. System 300 includes an external unit 130, such as shown in FIG. 1, and internal unit 120 that includes implant housing heatsink 131, laser drivers 133 that drive lasers 132. The light from lasers 132 is shaped by shaping optics 135, guided by waveguide 136, and delivered towards the nerves 98 of patient 99. In some embodiments, the implant housing heatsink 131 is made of a heat-conducting bio-compatible material that has a relatively large thermal mass that readily absorbs short heat spikes from the laser-diode drivers 133 and the laser diodes 132 and then dissipates the heat over a longer period of time to the body of patient 99. In some embodiments, the inner surface of implant housing heatsink 131 includes an inside layer of very-high thermal-conductivity material (e.g., in some embodiments, a layer of copper that is 0.5 mm to 3 mm thick) that readily absorbs short heat spikes from the pulsed signals (which can be 1 microsecond to 0.01 seconds or somewhat longer in duration), and an outer layer of thinner biocompatible material such as titanium or a polymer, which has a lower (but not too low) thermal conductivity to dissipate the heat over a longer period of time (e.g., 10 to 100 seconds) in order to prevent thermal damage to the tissue surrounding implant housing heatsink 131. Some embodiments include a heat sink for a cochlear implant that extends outside of the cochlea or that is placed outside of the cochlea. In some embodiments, the light from lasers 132 is shaped and inserted into waveguide(s) 136 by light-shaping element 135, and delivered by light waveguide 136 to light-delivery control optics 133, which control the final propagation of the light to the nerve bundle 98 in the patient 99 (which can be a human or other animal). As described above, some embodiments include an external-to-the-body portion 130 that includes sensors (e.g., microphones, accelerometers, gyroscopes and the like), electrical power, programming, input/output signals, transmitter/receiver and/or other devices.

Figure 4:
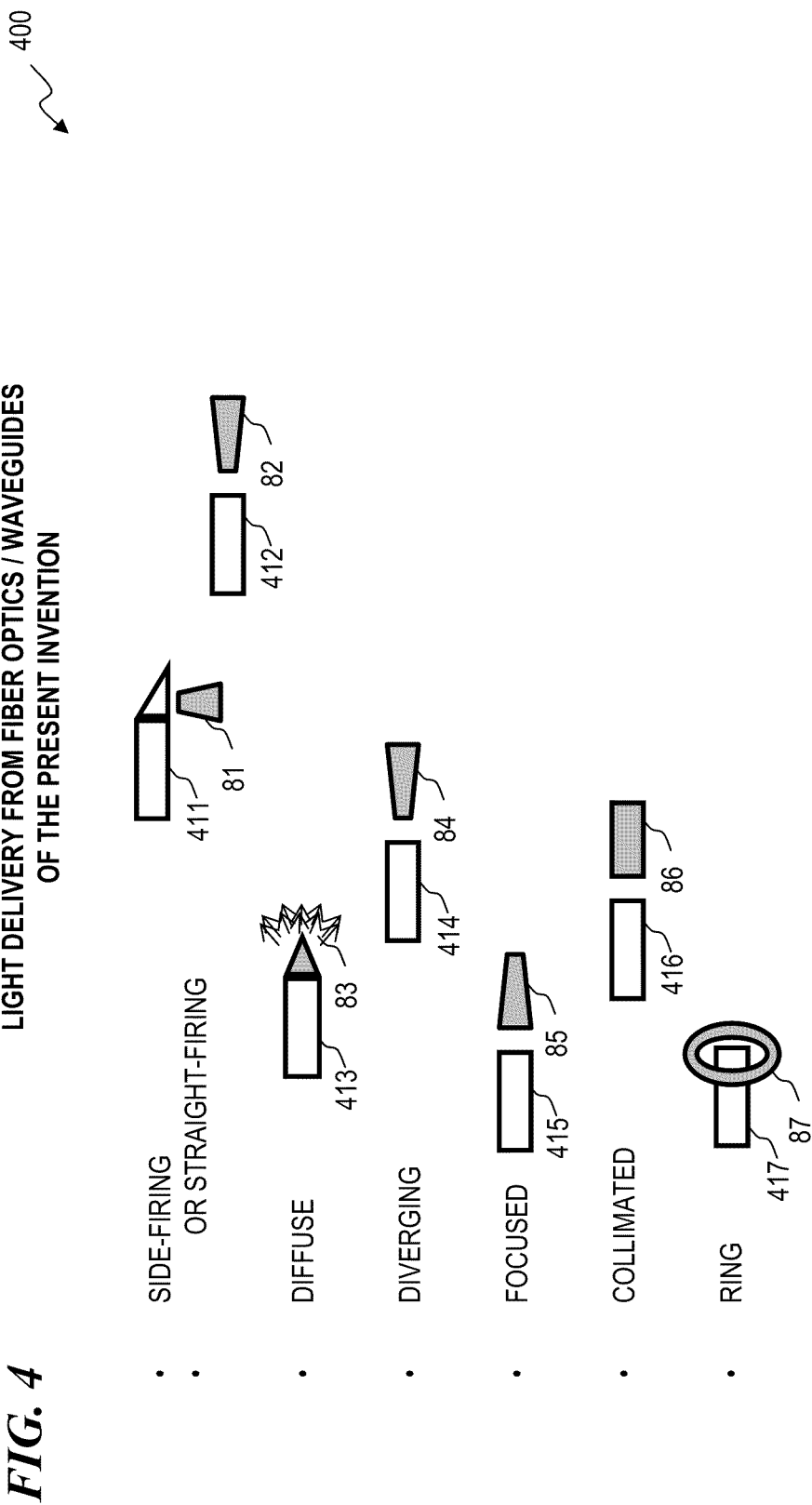
FIG. 4 is a specification of a plurality of light-delivery options 400 from fiber optics/waveguides.

FIG. 4 is a specification of a plurality of light-delivery options 400 from fiber optics/waveguides. In some embodiments, one or more of the light-delivery options is used in a system 100 as described above for FIG. 1B. In a first option, a waveguide 411 ends in an angled facet and/or fiber-Bragg grating that reflects or diffracts the light out in a radial or side ("side firing") direction of the waveguide as laser beam 81, and such a waveguide can be implanted such that the length of the end of fiber 411 is parallel to the nerve to be stimulated. In a second option, a waveguide 412 ends in an end facet that transmits the light out in an axial direction of the waveguide as laser beam 82, and such a waveguide can be implanted such that the length of the end of fiber 412 is perpendicular or at some other steep angle to the nerve to be stimulated. In a third option, a waveguide 413 ends in a conical (as shown), rough or ground "frosted" end that diffuses the light out in both axial and radial directions of the waveguide as laser pattern 83. In a fourth option, a waveguide 414 ends in a lens-type end facet that transmits and diverges the light out in an axial direction of the waveguide as laser beam 84. In a fifth option, a waveguide 415 ends in a lens-type end facet that transmits and focusses the light out in an axial direction of the waveguide as laser beam 85. In a sixth option, a waveguide 416 ends in a lens-type end facet that transmits and collimates the light out in a parallel beam in an axial direction of the waveguide as laser beam 86. In a seventh option, a waveguide 417 ends in an annular lens-type end facet that transmits and focusses the light out in a radially and axially extending conical ring centered about an axial direction of the waveguide as laser beam 87. In some such embodiments, the very end facet is polished and coated with a metallic or dielectric-layered reflective structure to better facilitate the ring-shaped output beam 87. In some embodiments, a combination of two or more of such features as shown in fiber ends 411, 412, 413, 414, 415, 416, and/or 417 are applied to a single fiber tip to provide a hybrid beam shape combining some aspects of light beams and/or patterns 81-87. In some embodiments, a bundle having a plurality of such fibers and ends are used in combination to get a plurality of beams and/or a plurality of beam shapes in a small area. In some embodiments, the ends of the plurality of fibers terminate at a plurality of different axial lengths to provide output beams that leave the bundle at different points along the length of the fiber bindle.

FIG. 5A is a block diagram of a VCSEL-based system 500 designed to be inserted (as a biocompatible, sealed package (in some embodiments, a hermetically sealed package)) into the scala tympani. In some embodiments, VCSEL system 500 includes a flexible substrate 501, onto which a plurality of VCSEL arrays 502 are affixed and electrically connected. A plurality of electrical signals 503 from diode driver(s) 133 drive the various VCSELs to emit light, and, in some embodiments, a plurality of other electrical signals is passed in electrical conductors on substrate 501 that are connected to exposed electrodes along the length of substrate 501, such that combined electrical and optical stimulation signals can be applied to each of a plurality of neurons. In some embodiments, the laser source includes a single VCSEL, having a light output beam in a single direction with the beam oriented towards the excitable tissue. In other embodiments, the laser source includes a plurality of VCSELs each oriented in the same direction (i.e., with their optical axes substantially parallel), and optionally with overlapping spots on the excitable tissue. In still other embodiments, the laser source includes a plurality of VCSELs oriented in many directions (i.e., with their optical axes directed in a plurality of different directions (e.g., in some embodiments, radially outward from a central axis)). In some embodiments, the laser source has no lens (since in some cases, the VCSEL is pressed against or located immediately next to the tissue it will be stimulating), while in other embodiments, the VCSEL is coupled to one or more micro-lenses that either: disperse the light over a larger area than the area of the emitter VCSEL, collimate the light (forming a beam of parallel rays), or focus the light to a smaller spot (having a smaller area than the area of the emitter) on excitable tissue (in some embodiments, the tissue includes the hair cells of the organ of Corti or spiral ganglion nerve cells). In some embodiments, the number of channels ranges from one to a hundred or more, and the number of VCSELs per channel ranges from one to five or more. For example, in some embodiments, 32 to 256 or more channels are used (each channel corresponding to a row of VCSELs across the width of substrate at a particular length location along the length of substrate 501, and thus to a location in the cochlea that corresponds to a particular frequency detection and sensation), wherein the pitch (spacing) between adjacent channels may be varied along the substrate length (providing a finer resolution in certain frequency ranges (e.g., frequencies needed for understanding speech) and coarser resolution for other frequencies (to reduce power and heat, and/or to reduce extraneous audio stimulation (background noise) to, for example, enhance speech understanding)). In some embodiments, each VCSEL will have two electrical leads to provide power, such that a linear array will grow in diameter as the electrical leads are twisted; thus in some embodiments, very thin wires are required (e.g., in some embodiments, carbon-nanotube conductors or other suitable high-conductivity electrical wires).

In some embodiments, device 500 is enclosed in a biocompatible external package having a natural affinity to bend in the shape of cochlear spiral, and is soft and flexible so no damage is occasioned during insertion. In some embodiments, the materials on the outside include Kapton® brand polyimide flex circuits, and/or a polyimide coating.

FIG. 5B is a schematic diagram of a VCSEL-based system 500 that is coiled from a base end (that is electrically connected to a driver circuit 133) to an apex end, such that the coiling of system 500 matches the coiling of the cochlea and is inserted into the cochlea. In some embodiments, system 500 is configured to be inserted within the cochlea, while in other embodiments, system 500 is configured to be placed outside and along the exterior of the cochlea. In some embodiments, each VCSEL source 502 includes a single VCSEL, while in other embodiments, each VCSEL source 502 includes a plurality of individually activatable lasers oriented to emit light along substantially parallel axes with somewhat overlapping spots of illumination (such that, in some embodiments, one or more of the group of VCSELs can be individually activated at a succession of different times after implantation, in order to dynamically determine which of the plurality of VCSELs in a single array 502 is best suited to stimulate one or more nerves that are very near to one another, but for which it is desired to selectively stimulate one or more individually without stimulating the adjacent neighboring nerves). In other embodiments, each group of VCSELs 502 are configured to emit laser light beams in a plurality of non-parallel directions to stimulate nerves that are not right next to one another. In some embodiments, each group of VCSELs 502 have an associated one or more lenses to focus the light (e.g., graded-index-fiber (GRIN) lenses or other suitable microlenses that either disperse the light in some embodiments, or in other embodiments, focus the light to a small spot of excitable tissue such as hair cells in the cochlea or spiral ganglion cells (SGCs)), while in other embodiments, no lenses are used. In some embodiments, a plurality of channels (e.g., two to a hundred or more channels) each have one or more VCSELs (e.g., in some embodiments, 1 to 5 VCSELs per channel), such that one or more of the VCSELs on a given channel can be selectively activated to stimulate nerves associated with that channel. In some embodiments, a plurality of VCSELs are each activated to trigger NAPs in additional neighboring spiral ganglion cells, and/or to increase the pulse repetition rate of NAPs in a particular set of nerve pathways in order to provide loudness control, as mentioned earlier. In some embodiments, each VCSEL is connected to two electrical conductors (namely, its individual signal conductor and a common or ground conductor that is shared with other VCSEL emitters). In some embodiments, an array of VCSELs will be arranged such that all VCSELs in any one row share an anode connection and all VCSELs in any one column share a cathode connection, and such that each VCSEL emitter is uniquely addressed by electrically driving its row anode and its column cathode (of course, the terms row and column can be interchanged). In some embodiments, the "rows" and "columns" and the conductors to each extend across a plurality of the VCSEL groups labeled 502 in FIG. 5A and FIG. 5B. That is, an array of ten rows and ten columns needs only twenty conductors to individually address one-hundred VCSEL emitters, and if each VCSEL group 502 includes five individual emitters, and there are twenty VCSEL groups 502, a single first column conductor can connect to the cathodes of all VCSELs on the first and second VCSEL group 502, while the first five row conductors connect to five respective VCSELs in the first VCSEL group 502, and the second five row conductors connect to five respective VCSELs in the second VCSEL group 502. The first column conductor thus does not need to extend beyond the second VCSEL group 502. Similarly, a single second column conductor can connect to the cathodes of all VCSELs on the third and fourth VCSEL group 502, while the first five row conductors connect to five respective VCSELs in the third VCSEL group 502, and the second five row conductors connect to five respective VCSELs in the fourth VCSEL group 502. The second column conductor thus does not need to extend beyond the fourth VCSEL group 502. A similar pattern then extends to the other sixteen VCSEL groups 502. Since the optical pulse to trigger a NAP can be very short (e.g., about 1 to 10 microseconds in duration, in some embodiments), up to all one-hundred emitters can be successively activated in a single millisecond interval, and for physiological effects, may appear for all intents and purposes to have all been substantially simultaneous.

In some embodiments, the implanted device of the present invention includes a sound sensor (microphone; not shown) that, upon activation by an external sound (pressure wave), generates one or more electrical signals. In some embodiments, a computerized sound analyzer decomposes the audio signal (e.g., using a fast Fourier transform (FFT), discrete cosine transform (DCT), or other suitable digital signal processor (DSP) or analog means) to output time-varying frequency components. In some embodiments, the optical stimulation signals from VCSEL arrays 502 and electrical stimulation signals are generated based on the outputted time-varying frequency components signals.

In some embodiments of the device 500 of FIG. 5A and FIG. 5B, the electrical stimulation portions (electrode driver 175, conductors 505 and 506 and electrodes 504 and 508) and are omitted and only the optical stimulation portions are implemented.

In some other embodiments, device 500 further includes electrical stimulation and/or sensitization functionality, as provided by electrode drivers (current sources) 175 that, for example, drive electrical conductors 505 that connect to a plurality of ring electrodes 504, each of which is on a surface of substrate 501 and surrounds a corresponding one the plurality of VCSEL arrays 502, and that faces the excitable tissue 98 (e.g., the spiral ganglion cells and the hair cells inside the cochlea) from inside the cochlea 78 (e.g., in some embodiments, substrate 501 extends inside the scala tympani 79 (the lower channel) in the cochlea 78 from near the base to near the apex, such that each VCSEL array 502 emits light toward the excitable tissue 98, and each electrode 504 creates an electric field and current that is most concentrated on the subportion of tissue 98 to which the light is directed. In some embodiments, each VCSEL array has a plurality of emitters that emit light for one or more sensory frequency channels (each sensory frequency channels being the nerve pathway from hair cells located to respond to a particular audio frequency and to initial NAPs in one of the auditory nerve pathways associated with that frequency). In the embodiment shown in FIG. 5, two rows of five VCSEL emitters extend across a width of each VCSEL array 502, while in other embodiments, other numbers of rows and other numbers of VCSEL emitters per row are provided. In some embodiments, via testing and mapping after implantation, one or more of the VCSEL emitters in one row is mapped and used to stimulate NAPs for one sensory frequency channel, while one or more of the VCSEL emitters in another row is mapped and used to stimulate NAPs for another sensory frequency channel. Multiple VCSELs are provided in each row (e.g., in some embodiments, many more than end up actually being used) in order that, to accommodate placement errors, testing of all or most of the stimulation sources, and then mapping of which stimulation causes each of a plurality of sensory responses or perceptions so that only the subset of stimulation sources that are most effective in causing a response are used to generate NAPs based on the information content of the audio signal.

In some embodiments, a second substrate 507 is placed in the scala vestibuli channel 77 and/or cochlear channel (see FIG. 26) in the cochlea 78, wherein the second substrate 507 includes one or more counter electrodes 508 that provide a return path for electrical current from the one or more electrodes 504 on substrate 501 located in the scala tympani channel 79 in the cochlea 78. In some embodiments, a single counter electrode 508 is used (equivalent to electrically connecting all the counter electrodes 508 of FIG. 5A together) and a single electrode 504 is used (equivalent to electrically connecting all the ring electrodes 504 of FIG. 5A together), which greatly reduces the wiring (the number of parallel conductors) needed for the electrical stimulation, but increased the current needed since much of the current is applied to tissue that is not going to be optically stimulated. In other embodiments, a single counter electrode 508 is used (equivalent to electrically connecting all the counter electrodes 508 of FIG. 5A together), but a plurality of electrodes 504 are used (such that each of a plurality of electrodes 504 of FIG. 5A are independently activatable), which still reduces the wiring needed for the electrical stimulation somewhat, but substantially reduces the electrical current used since current flows from one electrode to the portion of the counter electrode immediately opposite through only the subportion of excitable tissue that is to be optically stimulated (thus much less current is used stimulating tissue that is not to be optically stimulated). Similarly, in yet other embodiments, a single electrode 504 is used (equivalent to electrically connecting all the electrodes 504 of FIG. 5A together), but a plurality of counter electrodes 508 is used (such that each of a plurality of counter electrodes 508 of FIG. 5A are independently activatable), which also reduces the wiring needed for the electrical stimulation, and also substantially reduces the electrical current used since current flows from one electrode to the portion of the counter electrode immediately opposite through only the subportion of excitable tissue that is to be optically stimulated.

In still other embodiments, a plurality of electrodes 504 is used (equivalent to electrically connecting all the electrodes 504 of FIG. 5A together), but a plurality of counter electrodes 508 are used (such that each of a plurality of counter electrodes 508 of FIG. 5A are independently activatable), which increases (as compared to the approaches described in the prior paragraph) the wiring needed for the electrical stimulation, but also substantially reduces the electrical current used and increases the granularity of stimulation since current flows from one electrode to the portion of the counter electrode immediately opposite through only the subportion of excitable tissue that is to be optically stimulated. In some such embodiments, the plurality of electrodes 504 and the plurality of electrodes 508 are arranged in a cross-hatched pattern (e.g., with one or more groups of the electrodes 504 elongated in one direction (e.g., the X direction) and one or more groups of the counter electrodes 508 elongated in a perpendicular direction (e.g., the Y direction), such that when one of the X electrodes 504 is activated and one of the Y counter electrodes is activated (i.e., one to supply electrons and the other to provide a return path for the electrons), primarily only the tissue between the selected X electrode 504 and the selected Y counter electrode is stimulated (e.g., having a plurality of X-direction elongated electrodes in the scala tympani channel 79 and a plurality of Y-direction elongated electrodes in the scala vestibuli channel 77 and/or cochlear channel (see FIG. 26), wherein the X direction can be lengthwise (parallel), widthwise (perpendicular), or at an oblique or acute angle relative to the longest-length axis of the 501 substrate and the Y direction can be perpendicular to the X direction or at some other non-parallel angle to the X direction, such that only tissue between the closest intersection is stimulated.

In some embodiments, the optical stimulation portions of device 500 are omitted and electrical-only stimulation using a plurality of electrodes 504 and a plurality of electrodes 508 is used, wherein the improvement over conventional electrical-only stimulation devices is reduced power consumption and/or a finer granularity of stimulation that is obtained by using crossed elongated electrodes located on opposite sides of the excitable tissue (e.g., having a plurality of X-direction elongated electrodes in the scala tympani channel 79 and a plurality of Y-direction elongated electrodes in the scala vestibuli channel 77 and/or cochlear channel (see FIG. 26), wherein the X direction can be parallel or perpendicular, or at an oblique relative to the longest-length axis of the 501 substrate and the Y direction can be perpendicular to the X direction or at some other non-parallel angle to the X direction).

FIG. 6A is a block diagram of an implant system 600 for insertion into the cochlea for stimulating nerve cells with light according to one embodiment of the invention. In some embodiments, system 600 includes a plurality of light and electrical sources 602 that are outside the cochlea, connected via waveguides 604 to a combined waveguide 607 that conducts light of different wavelengths as separate signals in a wavelength-division-multiplexing (WDM) manner, such that the different-colored light is extracted by, e.g., gratings 623, 626, and 629, or by tuned wavelength filters. In this way, a first light signal having a first wavelength is emitted through window 622 as a first beam 621 and focussed on a first area of excitable tissue (e.g., cochlear hair cells for a first audio frequency), a second light signal having a second wavelength is emitted through window 625 as a second beam 624 and focussed on a second area of excitable tissue (e.g., cochlear hair cells for a second audio frequency), and a third light signal having a third wavelength is emitted through window 628 as a third beam 627 and focussed on a third area of excitable tissue (e.g., cochlear hair cells for a third audio frequency). In some embodiments, a plurality of electrical signals is also generated by sources 602 and electrically conducted (e.g., by conductors applied to the outside of optical waveguides 604 and 607), and applied to pre-sensitize the excitable tissue 98 such that a lower-powered optical signal beam (e.g., 621) can be used to trigger a NAP. In some embodiments, the optical windows 622, 625, and 628 include microlenses between the gratings and the target tissue in collimated, diverging, or converging patterns. In some embodiments, the microlenses direct light in circular path, or disperse light from 0 to 360 degrees in a radial pattern perpendicular to fiber with set area and divergence angle. In some embodiments, the window is hermetically sealed to the waveguide for output, and optionally may have a shape configured to shape the optical beam, while in other embodiments, there may be no window. In some embodiments, a MEMS (micro-electro-mechanical systems) device having a plurality of movable mirrors (e.g., see U.S. Pat. No. 4,596,992 to Hornbeck and U.S. Pat. No. 7,787,170 to Patel et al., which are both incorporated herein by reference) is activated to switch or move the mirrors into or out of the beam path, or otherwise deflect the optical signals to selectively stimulate neurons that lie along the path of the waveguide. In some embodiments, the device controls mirrors with piezoelectric material to 'move' the mirrors, while in other embodiments, electrostatic or other means are used.

FIG. 6B is a schematic diagram of implant system 600 that has been inserted into the cochlea 97 for stimulating nerve cells with light according to one embodiment of the invention.

FIG. 7A is a block diagram of an implant system 700 for insertion into the cochlea for stimulating nerve cells with light according to another embodiment of the invention. In some embodiments, system 700 uses a plurality of sources 702 that each emit a different wavelength of light and that generate coordinated electrical stimulation signals to sensitize the excitable tissue. In other embodiments, all of the light signals have substantially the same wavelength, since each signal is carried by a separate waveguide 704, 705, . . . 706 from the sources 702 to their respective ends where they emit the respective light beams 714, 715, . . . 716, each directed at a different target of excitable tissue 98. In some embodiments, the wavelength is matched to the desired penetration depth. In some embodiments, the sources 702 include VCSEL arrays. In some embodiments, the sources 702 include edge emitters. In some embodiments, each waveguide 704, 705, . . . 706 includes one or more electrical conductors that carry the electrical stimulation signals used to sensitize the excitable tissue of interest. In some embodiments, each waveguide 704, 705, . . . 706 includes one or more of the optical tips as described in FIG. 4 above.

FIG. 7B is a schematic diagram of implant system 700 that has been inserted into the cochlea 97 for stimulating nerve cells with light according to one embodiment of the invention, such that the plurality of waveguides 704, 705, . . . 706 and the respective electrical conductors are inserted in a spiral geometry inside the cochlea of the patient.

FIG. 8A is a block diagram of a wavelength-division multiplexing (WDM) system 800 for resting outside the cochlea for stimulating nerve cells with light according to one embodiment of the invention. System 800 is much the same as system 600 at the block-diagram level, but is configured to be implanted in the inner-ear region but outside the cochlea (e.g., in some embodiments, system 800 is imbedded in the temporal bone and light signals are transmitted through the temporal bone to the target). In some embodiments, system 800 includes a plurality of light and electrical sources 802 that are outside the cochlea, connected via waveguides 804-806 to a combined waveguide 807 (also outside the cochlea) that conducts light of different wavelengths as separate signals in a wavelength-division-multiplexing (WDM) manner, such that the different-colored light is extracted by, e.g., gratings 823, 826, and 829. In this way, a first light signal having a first wavelength is emitted through window 822 as a first beam 821 and focussed on a first area of excitable tissue (e.g., through the cochlea wall to cochlear hair cells for a first audio frequency), a second light signal having a second wavelength is emitted through window 825 as a second beam 824 and focussed on a second area of excitable tissue (e.g., cochlear hair cells for a second audio frequency), and a third light signal having a third wavelength is emitted through window 828 as a third beam 827 and focussed on a third area of excitable tissue (e.g., cochlear hair cells for a third audio frequency). In some embodiments, a plurality of electrical signals is also generated by sources 802 and electrically conducted (e.g., by conductors applied to the outside of optical waveguides 804-806 and 807), and applied to pre-sensitize the excitable tissue 98 such that a lower-powered optical signal beam (e.g., 821) can be used to trigger a NAP. In some embodiments, the optical windows 822, 825, and 828 include microlenses between the gratings and the target tissue in collimated, diverging, or converging patterns. In some embodiments, the microlenses direct light in a circular path, or disperse light from 0 to 360 degrees in a radial pattern perpendicular to the fiber with a set area and divergence angle. In some embodiments, the window is hermetically sealed to the waveguide for output, and optionally may have a shape configured to shape the optical beam, while in other embodiments, there may be no window. In some embodiments, system 800 is oriented in parallel to the cochlea, is situated in the temporal bone, and is shaped in the geometry of the cochlear target. In some embodiments, light signals are transmitted from system 800 through the round window of the cochlea and to the basal turn of the cochlea. In some embodiments, as shown in FIG. 8A, gratings 823, 826, and 829 are arranged in a linear array. In some embodiments, gratings 823, 826, and 829 are arranged in a three-dimensional array. In some embodiments, the invention includes multiple arrays of system 800 arranged in a parallel configuration.

FIG. 8B is a schematic diagram of implant system 800 that is placed outside but adjacent the cochlea 97 for stimulating nerve cells with light, according to one embodiment of the invention.

Figure 9:
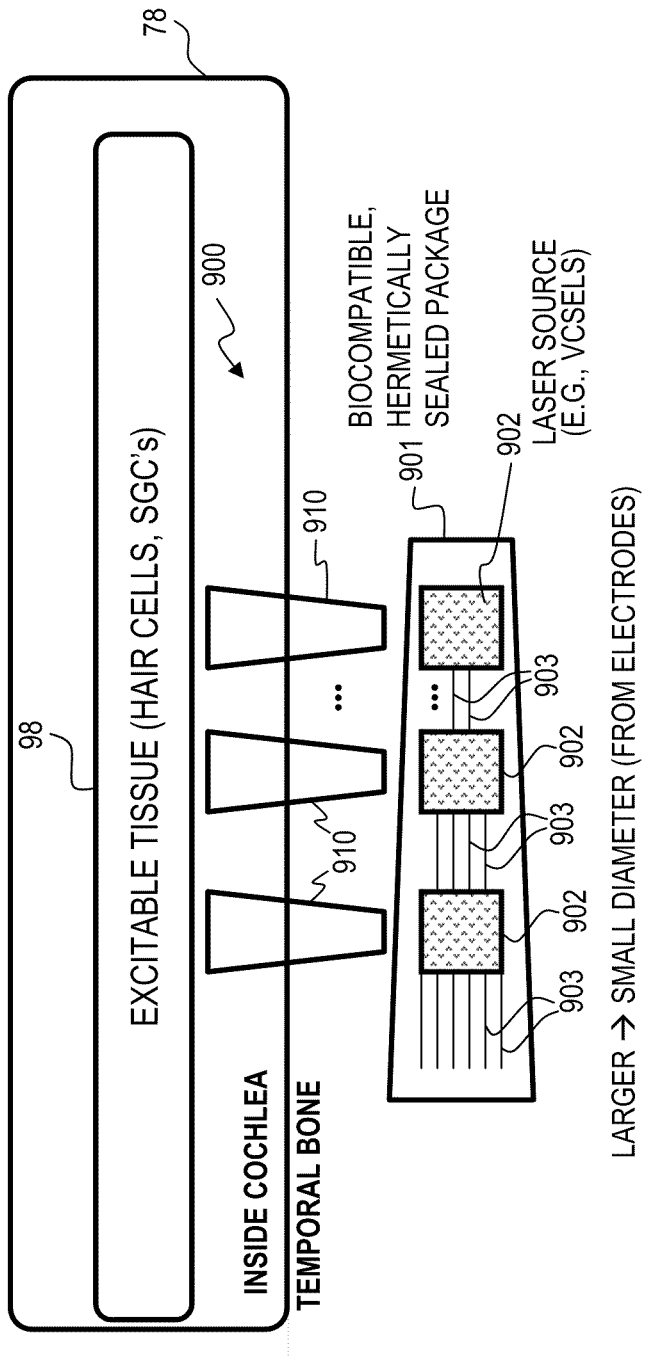
FIG. 9 is a diagram of a system 900 resting outside the cochlea for stimulating nerve cells with light according to another embodiment of the invention.

FIG. 9 is a diagram of a system 900 resting in the temporal bone outside the cochlea for stimulating nerve cells with light according to another embodiment of the invention. This system 900 is much the same as system 500 described in FIG. 5A above, except that system 900 is designed to be implanted within the temporal bone behind the ear and includes optical elements configured to focus the stimulation light through the inner surface of the temporal bone towards the plurality of areas of the cochlea to be stimulated. In some embodiments, VCSEL system 900 includes a flexible substrate 901, onto which a plurality of VCSEL arrays 902 are affixed and electrically connected. A plurality of electrical signals 903 drive the various VCSELs to emit light, and, in some embodiments, a plurality of other electrical signals is passed in electrical conductors on substrate 901 that are connected to exposed electrodes along the length of substrate 901, such that combined electrical and optical stimulation signals can be applied to each of a plurality of neurons. In some embodiments, the light output beam 910 of a VCSEL array 902 propagates in a single direction with the beam 910 oriented towards the excitable tissue 98.

FIGS. 10A, 10B, and 10C are diagrams of embodiments of three-dimensional (3D) VCSEL-array system 1000 resting outside the cochlea for stimulating nerve cells with light according to another embodiment of the invention. System 1000C of FIG. 10C can be used for system 1008 that emits light beams 1009 through the round window or oval window into the cochlea (excitable tissue 98) of the inner ear as shown in FIG. 10A, or for system 1006 that emits light beams 1007 through the inner surface of temporal bone towards the cochlea 97 of the inner ear as shown in FIG. 10B. In some embodiments, the target of the emitted light beams 1009 and/or emitted light beams 1007 is the basal turn of the cochlea 97. As shown in FIG. 10C, in some embodiments, system 1000C includes a hermetically sealed package 1001 having a heat-sink structure 1012 having an outer surface that conducts heat to the body of the patient 99, and an inner surface onto which is mounted VCSEL array 1013, which is facing and emitting light towards and through lens array 1002 to output a plurality of N output beams 1003 that are collimated in some embodiments, and focussed in other embodiments, to stimulate cochlea excitable tissue. In some embodiments, electrical signals are also applied to sensitize the excitable tissue.

FIGS. 11A, 11B, and 11C are diagrams of system 1100 (shown as system 1100A in FIG. 11A, which can be used to excite through bone (e.g., system 1100B as shown in FIG. 11B) or through the round or oval window of the inner ear (e.g., system 1100C as shown in FIG. 11C), implanted and resting outside of the cochlea for stimulating auditory nerve cells with light that propagates through bone (of the embodiment of FIG. 11B) according to another embodiment of the invention. As shown in FIG. 11A, system 1100A is much the same as system 700 of FIG. 7A, and includes a plurality of sources 1120 that each emit a different wavelength of light and that (in some embodiments) generate coordinated electrical stimulation signals to sensitize the excitable tissue. In other embodiments, all of the light signals have substantially the same wavelength, since each signal is carried by its own separate waveguide 1140 from the sources 1120 to their respective ends where they emit the respective light beams 1111, 1112, . . . 1113, each directed at a different target of excitable tissue 98. In some embodiments, the wavelength is matched to the desired penetration depth. In some embodiments, the sources 1120 include VCSEL arrays. In some embodiments, the sources 1120 include edge emitters. In some embodiments, each waveguide 1140 includes one or more electrical conductors that carry the electrical stimulation signals used to sensitize the excitable tissue of interest. In some embodiments, each separate waveguide 1140 includes one or more of the optical tip designs as described in FIG. 4 above.

FIG. 11B shows a system 1100B in which the source array of VCSELs 1150 (e.g., in some embodiments, source array of VCSELs 1150 is such as a system 1000C described in FIG. 10C) is connected to a plurality of waveguides 1113, each of which is outside and adjacent the cochlea and emits light towards the cochlea. In some embodiments, different wavelengths in the various waveguides 1113 are used to obtain different penetration depths, and thus allow selective excitation of different nerves.

FIG. 11C shows a system 1100C in which the source array of VCSELs 1151 (e.g., in some embodiments, source array of VCSELs 1150 is such as a system 1000C described in FIG. 10C) is connected to a plurality of waveguides 1114, each of which is outside and terminates at the round window or the oval window of the cochlea and emits light towards and into the cochlea. In some embodiments, different wavelengths in the various waveguides 1114 are used to obtain different penetration depths, and thus allow selective excitation of different nerves.

In some embodiments, the stimulation sources are distributed non-uniformly to optimize hearing perception (having a higher density of excitation units where a higher resolution (more different frequency channels) is desired and a lower density in other areas.

Note that in each instance herein where electrical stimulation is discussed, it is to be understood that in instances where optical stimulation is also discussed, some embodiments have a first mode of operation that uses a sub-threshold electrical stimulation (also called electrical sensitization), wherein the electrical stimulation alone is not enough (i.e., it is sub-threshold) to cause triggering of a NAP, but the electrical stimulation causes a sensitization that reduces the threshold for optical stimulation to cause a NAP. Thus the electrical "sensitization" cooperates with the optical stimulation together to cause one or more NAPs. In some such embodiments, the device also has a second mode that increases the electrical current such that the electrical stimulation alone is sufficient to trigger one or more NAPs. In some embodiments, this second mode is used to trigger NAPs to represent a wideband audio signal, while the first mode is used to trigger NAPs representing narrow-band audio signals having discrete frequencies, to which the small-spot-size optical stimulation is directed.

Figure 12C:
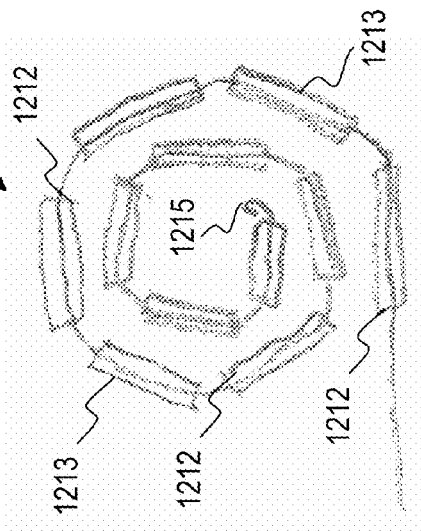
FIG. 12C is a cross-sectional diagram of a stimulation system 1201 in a unfolded and curled deployed configuration 1201-3 that would be after implantation, according to some embodiments of the invention.
Figure 12A:
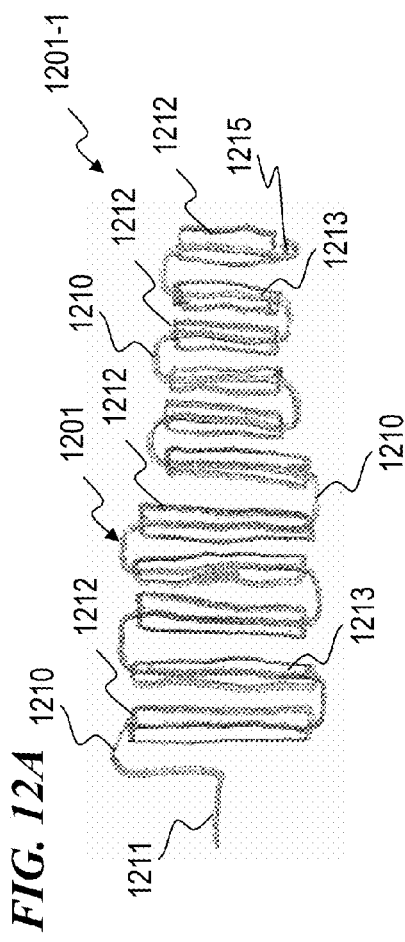
FIG. 12A is a cross-sectional diagram of a stimulation system 1201 in a folded configuration 1201-1 that would be seen before implantation, according to some embodiments of the invention.

FIG. 12A is a cross-sectional diagram of a stimulation device 1201 in a folded configuration 1201-1 that would be seen before implantation, according to some embodiments of the invention. In some embodiments, device 1201 starts in a folded-up configuration having a plurality of stimulation units 1212 (e.g., each having a plurality of optical stimulation emitters and one or more electrical stimulation electrodes) located on the top side (the side that would face the organ of Corti and/or the spiral ganglion cells if implanted in the scale tympani) of substrate 1210. Substrate 1210 extends from a first end 1211 (that would end up near the base of the cochlear channels) to a distal end (that would end up near the apex of the cochlear channels). In some embodiments, a second plurality of stimulation units 1213 is located on an opposite face of substrate 1210. In some such embodiments, the second plurality of stimulation units 1213 include electrodes only, and are used to provide a return electrical path for electrodes that surround or is adjacent the optical emitters in stimulation units 1212. In other embodiments, the stimulation units 1212 and stimulation units 1213 both emit light towards the target tissues from opposite sides and one or both are used to direct the electrical current from their electrodes. In some embodiments, substrate 1210 is made of a shape-memory metal or similar material that when deployed returns to a desired spiral shape as shown in FIGS. 12B and 12C.

Figure 12B:
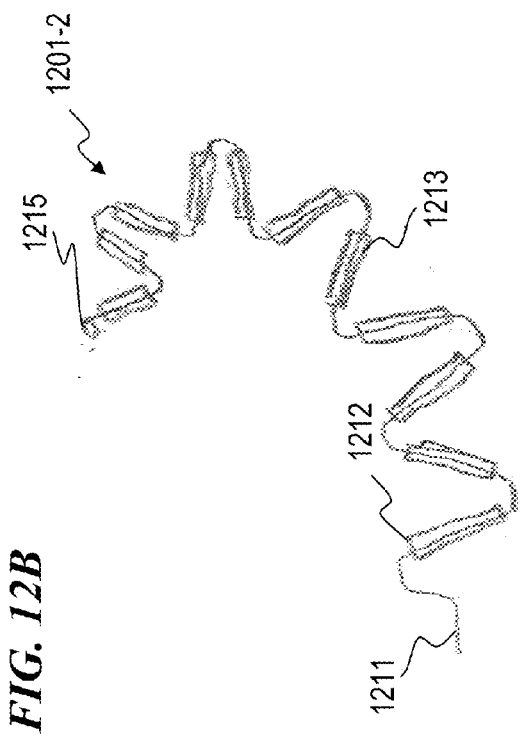
FIG. 12B is a cross-sectional diagram of a stimulation system 1201 in a partially unfolded configuration 1201-2 that would be during implantation, according to some embodiments of the invention.

FIG. 12B is a cross-sectional diagram of a stimulation device 1201 in a partially unfolded configuration 1201-2 that would be during implantation, according to some embodiments of the invention. At this point in deployment, device has partially unfolded along a path and shape that permits easier insertion into the cochlea (e.g., into the scala tympani channel).

FIG. 12C is a cross-sectional diagram of a stimulation device 1201 in a unfolded and curled deployed configuration 1201-3 that would exist after implantation in the cochlea (e.g., into the scala tympani channel), according to some embodiments of the invention. In some such embodiments, the resulting shape has a spring tension that presses the emitting elements against the tissue to be stimulated (e.g., the organ of Corti and the spiral ganglion cells) (see also FIG. 30). In other embodiments, the sides of substrate 1210 include one or more tiny hooks that hold device 1201 in place by hooking into edges of the tissue of the cochlea. In still other embodiments, a soft polymer material (such as a soft silicon tube or rod that is, in some embodiments, transparent) is inserted along one face of device 1201 to press device 1201 against the surface of the tissue to be stimulated.

Figure 13A:
FIG. 13A is a cross-sectional diagram of a stimulation system 1301 in a straight configuration 1301-1 that would be seen before implantation, according to some embodiments of the invention.

FIG. 13A is a cross-sectional diagram of a stimulation device 1301 in a straight configuration 1301-1 that would be seen before implantation, according to some embodiments of the invention. In some embodiments, this device 1301 is the converse of device 1201, in that it starts out straight and as it is inserted, the shape-memory metal returns to the curled-up state. In some embodiments, device 1301 includes a substrate 1310 having a plurality of stimulation units 1312 (e.g., each having a plurality of optical stimulation emitters and one or more electrical stimulation electrodes) located on the top side (the side that would face the organ of Corti and/or the spiral ganglion cells if implanted in the scale tympani) of substrate 1310. Substrate 1310 extends from a first end 1311 (that would end up near the base of the cochlear channels) to a distal end (that would end up near the apex of the cochlear channels). In some embodiments, a second plurality of stimulation units 1313 is located on an opposite face of substrate 1310. In some such embodiments, the second plurality of stimulation units 1313 include electrodes only, and are used to provide a return electrical path for electrodes that surround or is adjacent the optical emitters in stimulation units 1312. In other embodiments, the stimulation units 1312 and stimulation units 1313 both emit light towards the target tissues from opposite sides and one or both are used to direct the electrical current from their electrodes. In some embodiments, substrate 1310 is made of a shape-memory metal or similar material that when deployed returns to a desired spiral shape as shown in FIGS. 13B and 13C.

Figure 13B:
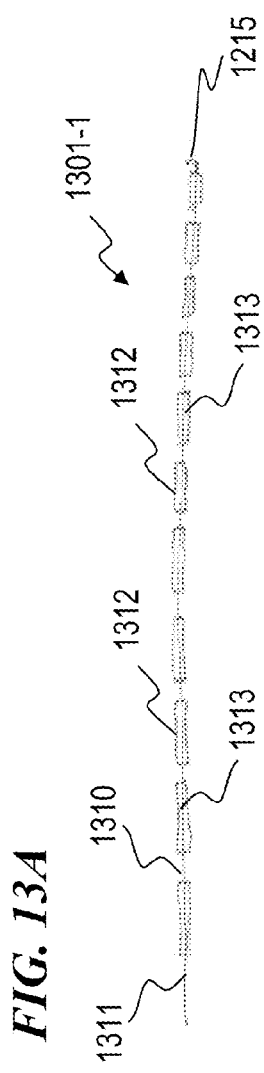
FIG. 13B is a cross-sectional diagram of a stimulation system 1301 in a partially curled configuration 1301-2 that would be during implantation, according to some embodiments of the invention.
Figure 13C:
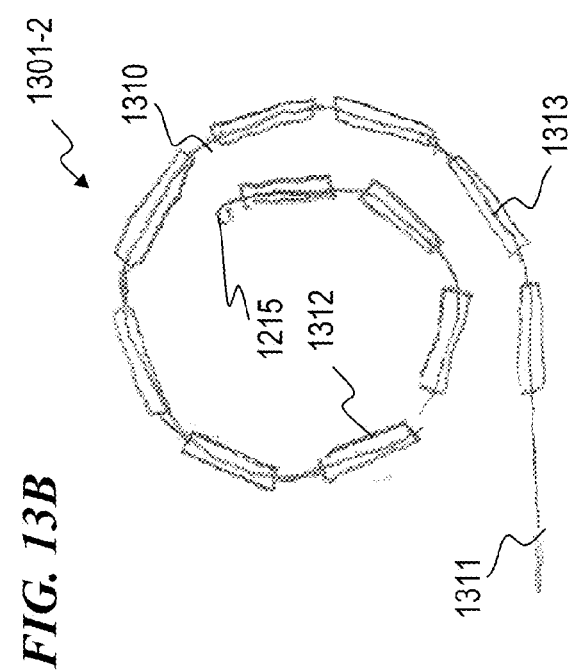
FIG. 13C is a cross-sectional diagram of a stimulation system 1301 in a curled deployed configuration 1301-3 that would be after implantation, according to some embodiments of the invention.

FIG. 13B is a cross-sectional diagram of a stimulation device 1301 in a partially curled configuration 1301-2 that would be during implantation, according to some embodiments of the invention.

FIG. 12C is a cross-sectional diagram of a stimulation device 1301 in a curled deployed configuration 1301-3 that would be after implantation, according to some embodiments of the invention.

In some embodiments, the non-uniform distribution includes a logarithmic spatial distribution to correlate optical-stimulation-source spatial distribution with frequency spatial distribution in the cochlea. In some embodiments, optical sources are distributed in a non-uniform pattern with a higher density of sources in the area of the cochlea to optimize hearing and/or music (e.g., fewer stimulation sources at high frequencies (above 3000 Hz) and/or fewer sources at low frequencies (those below about 300 Hz), such that a concentration of independent stimulation channels or optical sources are in the central portion of cochlea such that more channels are associated with respective frequencies that are most important for the type of hearing needed (e.g., in some embodiments, speech comprehension, then perhaps music and/or danger recognition or the like). In some embodiments, channels are added that are associated with frequencies most critical to speech comprehension (e.g., the 500 Hz to 3 kHz region of the cochlea (in other embodiments, other suitable frequency ranges are used)).

In some embodiments, the optical and electrical sources are adjacent to each other. In some of these embodiments, any or all optrodes are paired with an electrode. In others of these embodiments, any or all electrodes are paired with an optrode and additional optrodes added between the pairs. In some embodiments, an optrode is located inside a ring electrode. For example, in some embodiments, the VCSEL housing is made of an electrically conductive material to be used as an electrode.

In some embodiments, the implant of the present invention has a non-uniform spacing of stimulation optrodes and/or electrodes, and in some embodiments, the non-uniform spacing includes a logarithmic spacing for at least a plurality of the excitation units.

In some embodiments, the implant of the present invention includes a heat spreader strip in the cochlea on which lasers (e.g., VCSELs or edge-emitting semiconductor devices) are mounted (and, in some embodiments, extending outside of the cochlea to dissipate heat out of the patient).

In some embodiments, the implant of the present invention includes reprogrammable hearing mapping, such that the controller can be reprogrammed after implantation to stimulate each nerve pathway using the stimulation optrodes and electrodes that are most effective in obtaining the desired sensation for the patient. In some embodiments, the optrodes include a VCSEL array having emitters distributed along both a width and a length of the cochlear implant substrate (e.g., providing individually addressable VCSEL patterns in X and Y dimensions in the cochlea). In some embodiments, the stimulation and/or sensitization electrode serves as one electrical connection to neighboring VCSELs. In some embodiments, loudness compensation is achieved by adjusting which VCSELs are activated to recruit additional spiral ganglion cells, and/or increasing the pulse repetition rate of NAPS in a particular set of nerve pathways.

In some embodiments, MEMS (micro-electro-mechanical systems) units having a plurality of electrically activatable or controllable mechanical actuators that adjust positions of light emitters or light-guiding elements (moving optical fibers, lenses, mirrors or other light-guiding elements) in the array.

In some embodiments, the present invention includes an apparatus and method of shining through the round window of the cochlea in a plurality of directions in combination with selective electrical sensitization to achieve finely selective NAP triggering.

In some embodiments, the present invention includes controlling the VCSEL array to provide benefits including optimizing spatial location to stimulate intended frequency area in the cochlea, adjusting stimulation location to compensate for movement of the implant after implantation, or to adjusting for biological changes in excitability of tissue in the cochlea, and using the VCSEL as a means for loudness adjustment by activating adjacent VCSELS to recruit additional hair cells in the cochlea.

In some embodiments, the present invention provides a method and apparatus for electronically addressing an optical-emitter array. In some such embodiments, microprocessor-controlled multiplexers are used to select optical channels to be activated. In some embodiments, the microprocessor-controlled multiplexers are substantially similar to a row/column dot-matrix controller.

In some embodiments, the present invention includes optrodes connected in series. In some embodiments, the present invention includes optrodes connected in parallel.

Figure 14A:
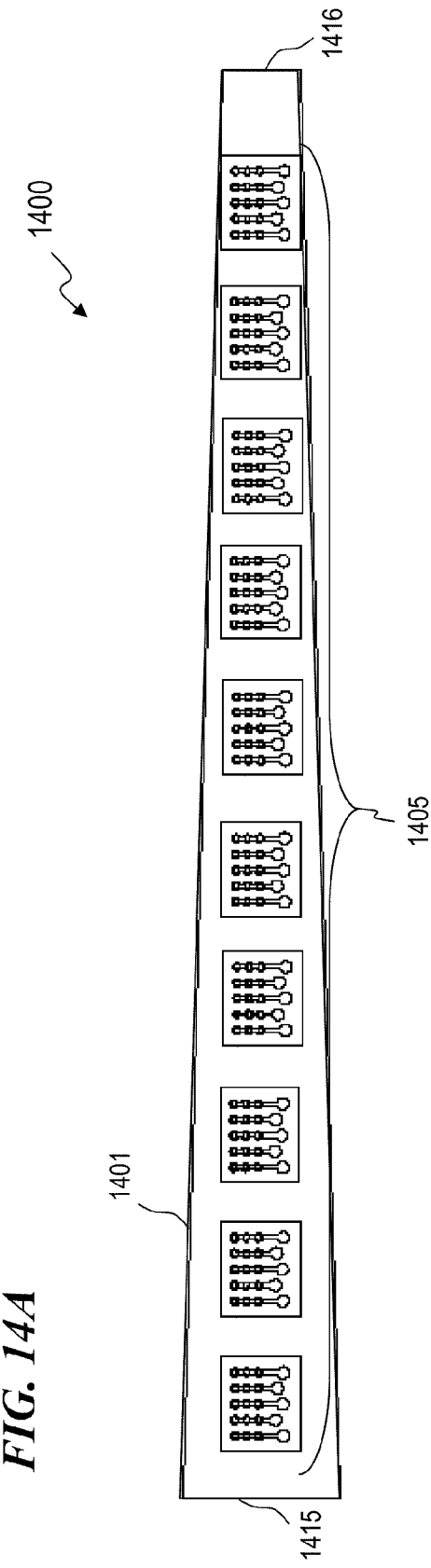
FIG. 14A is a stimulation system 1400 configured to be implanted within the cochlea of a living subject (e.g., a human).

FIG. 14A is a stimulation system 1400 configured to be implanted within the cochlea of a living subject (e.g., a human). In some embodiments, for example, system 1400 is inserted into the scala tympani 79 of the cochlea 78. In some embodiments, system 1400 includes a flexible substrate 1401, onto which a plurality of optical-emitter arrays 1405 are affixed and electrically connected. In some embodiments, system 1400 is substantially similar to system 500 of FIG. 5A. In some embodiments, substrate 1401 tapers from a first end 1415 to a second end 1416 such that substrate 1401 has a shape that conforms to the inner surface area of the cochlea. In some embodiments, each one of the plurality of optical-emitter arrays 1405 include a plurality of individually controlled optical emitters 1406 (see FIG. 14B). In some embodiments, the plurality of optical emitters 1406 is vertical-cavity-surface-emitting lasers (VCSELs). In some embodiments, the optical-emitter arrays 1405 are arranged in an addressable laser pattern to facilitate locality identification and/or selection for optimal stimulation.

Figure 14B:
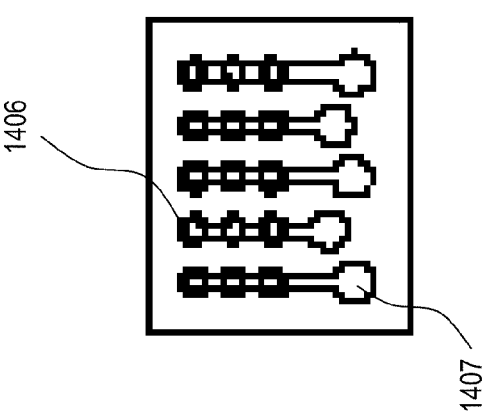
FIG. 14B is a plan view of an individual optical-emitter array 1405.

FIG. 14B is a plan view of an individual optical-emitter array 1405. In some embodiments, optical-emitter array 1405 includes a plurality of optical emitters 1406 and a plurality of electrical contacts 1407. In some embodiments, optical-emitter array 1405 includes five columns of one-by-three (1×3) optical emitters 1406 (in other embodiments, each optical-emitter array 1405 includes five columns of one-by-four (1×4) optical emitters 1406, in still other embodiments, five columns of one-by-five (1×5) optical emitters 1406, or, in other embodiments, any other suitable number and arrangement of optical-emitters 1406). In some embodiments, a plurality of electrical signals are passed in electrical conductors on substrate 1401 and are connected to exposed electrical contacts 1407 along the length of substrate 1401, such that combined electrical and optical stimulation signals can be applied to each of a plurality of neurons.

Figure 15C:
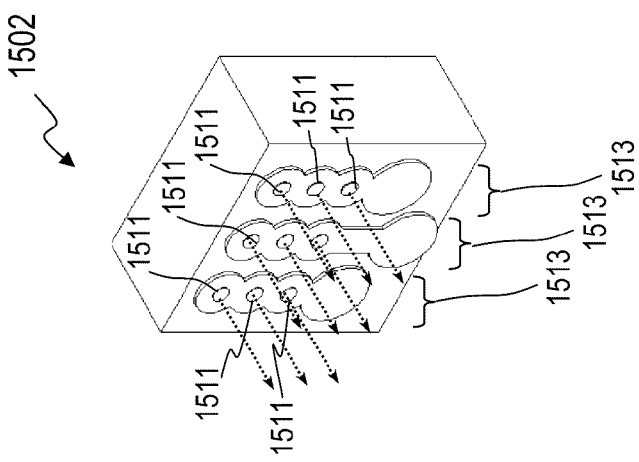
FIG. 15C is a perspective view of a portion of an optical-emitter array 1502 used in some embodiments of the present invention.
Figure 15B:
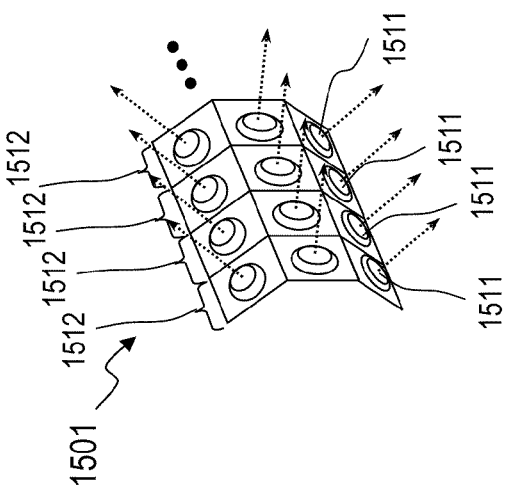
FIG. 15B is a perspective view of a portion of an optical-emitter array 1501 used in some embodiments of the present invention.
Figure 15A:
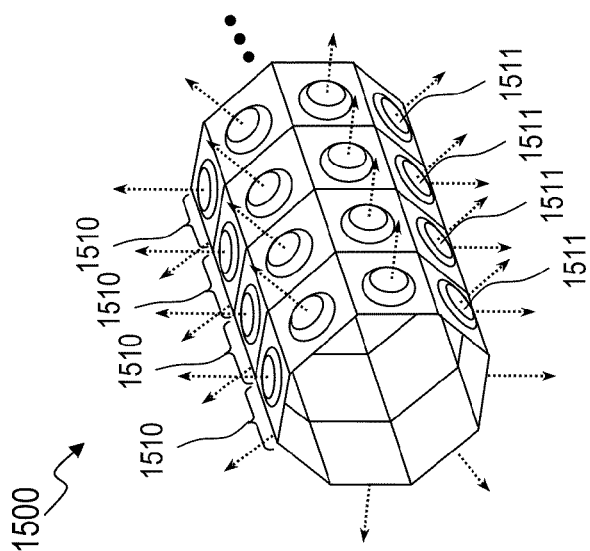
FIG. 15A is a perspective view of a portion of an optical-emitter array 1500 used in some embodiments of the present invention.

In some embodiments, the present invention includes VCSELs placed on substrate in a shape optimized to conform to the inner surface area of the cochlea, e.g., radially pointing in a plurality of different angles in a plane perpendicular to the longitudinal axis extending the longest dimension of the cochlear emitter array, as shown in FIG. 15A and FIG. 15B.

FIG. 15A is a perspective view of a portion of an optical-emitter array 1500 used in some embodiments of the present invention. In some embodiments as shown here, each of a plurality of optical emitters 1511 of each of the plurality of radial emitter sets 1510 of array 1500 are radially pointing in one of a plurality of different angles, with the optical axis of each optical beam being substantially in a plane perpendicular to the longitudinal axis extending the longest dimension of the optical-emitter array 1500, while in other embodiments, the light is directed at other angles (e.g., in some embodiments, the optical axes of the beams lie in a cone or other configuration) relative to the longitudinal axis. In some embodiments, optical-emitter array 1500 includes a plurality of (e.g., four) adjacent one-by-eight (1×8) emitter sets 1510 of optical emitters 1511 (in other embodiments, other numbers of emitter sets 1510 per array 1500 (e.g., integer values between 2 and 512, or more, emitter sets 1510 per array 1500) are provided, and other numbers of optical emitters 1511 per emitter set 1510 (e.g., integer values between 2 and 64, or more, optical emitters 1511 per emitter set 1510) are provided). In some embodiments, each individual 1×8 emitter set 1510 is arranged such that the angle of the light propagation (i.e., the optical axis of the light beam) of an individual emitter differs by 45 degrees with the optical axis of adjacent light emitters (e.g., in some embodiments, each 1×8 emitter set 1510 of system 1500 forms an octagonal shape). In some embodiments, optical-emitter array 1500 includes a plurality of (e.g., four) adjacent one-by-six (1×6) emitter sets 1510 of optical emitters 1511. In some such embodiments, each individual 1×6 emitter set 1510 is arranged such that the angle of the light propagation (i.e., the optical axis of the light beam) of an individual emitter differs by 60 degrees with the optical axis of adjacent light emitters (e.g., in some embodiments, each 1×6 emitter set 1510 of system 1500 forms a hexagonal shape). In some embodiments, array 1500 includes a plurality of emitter sets, at least some of which have a larger number of optical emitters 1511 than other emitter sets have (for example, at the larger end of a cochlear implant, there may be one or more emitter sets each having sixteen emitters per emitter set, and then next to those are one or more emitter sets each having twelve emitters per emitter set, then one or more emitter sets each having ten emitters per emitter set, then one or more emitter sets each having eight emitters per emitter set, then one or more emitter sets each having six emitters per emitter set, and then one or more emitter sets each having four emitters per emitter set). In still other embodiments, optical-emitter arrays include any other suitable number and configuration of optical emitters 1511 per emitter set 1510, or emitter sets 1510 per array 1500. By providing a large number of emitters arranged to emit light in a plurality of different circumferential angles, the device 1500 can be implanted in the cochlea in approximately the position needed, and then its controller can be programmed to use the emitters that stimulate NAPs in particular nerve pathways, and not to use emitters that do not stimulate NAPs in those particular nerve pathways.

FIG. 15B is a perspective view of a portion of an optical-emitter array 1501 used in some embodiments of the present invention. In some embodiments, optical-emitter array 1501 includes a plurality (e.g., four) of one-by-three (1×3) emitter sets 1512 of optical emitters 1511, wherein each individual 1×3 emitter set 1512 is arranged such that the angle of light propagation of an individual emitter differs by 45 degrees with the light-propagation angle of adjacent light emitters. In some embodiments, each individual 1×3 emitter set 1512 is arranged such that the angle of light propagation of an individual emitter differs by any other suitable angle with the light-propagation angle of adjacent light emitters.

FIG. 15C is a perspective view of a portion of an optical-emitter array 1502 used in some embodiments of the present invention. In some embodiments as shown here, optical-emitter array 1502 includes a plurality (e.g., three) of one-by-three (1×3) planar emitter sets 1513 of optical emitters 1511. In some embodiments, the plurality of emitter sets 1513 are arranged on a first surface of a three-dimensional chip such that the optical axis of each optical beam from each emitter 1511 is substantially in a plane perpendicular to the first surface (i.e., all of the optical emitters 1511 propagate light in a substantially parallel direction).

FIG. 16A is a side view of a stimulation system 1600. In some embodiments, stimulation system 1600 includes a plurality of optical emitters 1621 located on a flexible heat-sink spine 1611. In some embodiments, the plurality of optical-emitters 1621 includes VCSELs. In some embodiments, heat-sink spine 1611 is configured to coil such that it can be implanted inside a cochlea (e.g., in some embodiments, substrate system 1600 is implanted in the scala tympani 79 of a cochlea 78).

FIG. 16B is a perspective cross-section view of stimulation system 1600. In some embodiments, heat-sink spine 1611 is configured to remove excess heat generated by optical emitters 1621. In some embodiments, heat-sink spine 1611 extends outside of the cochlea when system 1600 is implanted in the cochlea. In some embodiments, heat-sink spine 1611 includes very-high thermal-conductivity material (e.g., in some embodiments, a layer of copper that is 0.5 mm to 3 mm thick) that readily absorbs short heat spikes from the pulsed signals (which can be 1 microsecond to 0.01 seconds or somewhat longer in duration). In some embodiments, system 1600 includes an encapsulant 1615 configured to encapsulate at least the portion of system 1600 that is implanted within the cochlea. In some embodiments, encapsulant 1615 has a lower (but not too low) thermal conductivity to dissipate the heat over a longer period of time (e.g., 10 to 100 seconds) in order to prevent thermal damage to the tissue surrounding system 1600. In some embodiments, the encapsulant includes a biocompatible material such as polyanhydride, silicon, or any other suitable biocompatible material. In some embodiments, electrical power is provided to system 1600 along a conduit 1606 (shown as dark line in FIG. 16B) that is located on heat-sink spine 1611.

Figure 17:
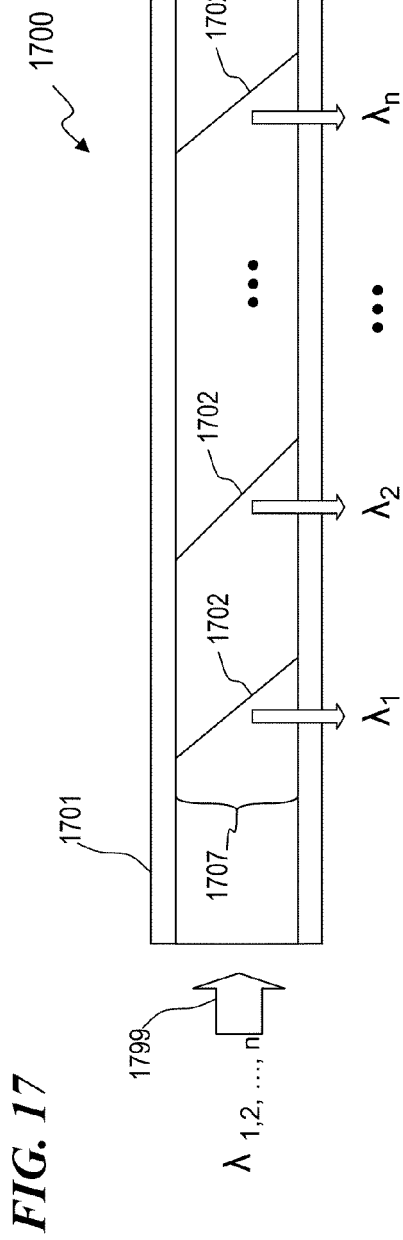
FIG. 17 is a schematic cross-section view of a waveguide-light-delivery system 1700 that is wavelength encoded with mirrors.

FIG. 17 is a schematic cross-section view of a waveguide-light-delivery system 1700 that is wavelength encoded with mirrors. In some embodiments, light 1799 enters waveguide 1701 at a first end, passes through a plurality of electrically controlled dielectric mirrors 1702, and exits at a second end of waveguide 1701. In some embodiments, light 1799 includes a plurality of wavelengths when it enters waveguide 1701, and light-delivery system 1700 is configured such that only a single wavelength of light 1799 is propagated down the entire length waveguide 1701. In some embodiments, a different wavelength of light 1799 is reflected out of the side of the waveguide 1701 at each different dielectric mirror 1702. For example, in some embodiments, the plurality of dielectric mirrors 1702 includes a first mirror 1702 that reflects light of a first wavelength $\lambda_1$, a second mirror 1702 that reflects light of a second wavelength $\lambda_2$, and an nth mirror 1702 reflects light of a wavelength $\lambda_n$. In some embodiments, if switched fast enough, all channels can be serviced with one laser. In some embodiments, mirrors 1702 reflect light 1799 from the core 1707 out to the side of waveguide 1701 in the "ON" state, and light 1799 passes through mirrors 1702 in the "OFF" state.

Figure 18:
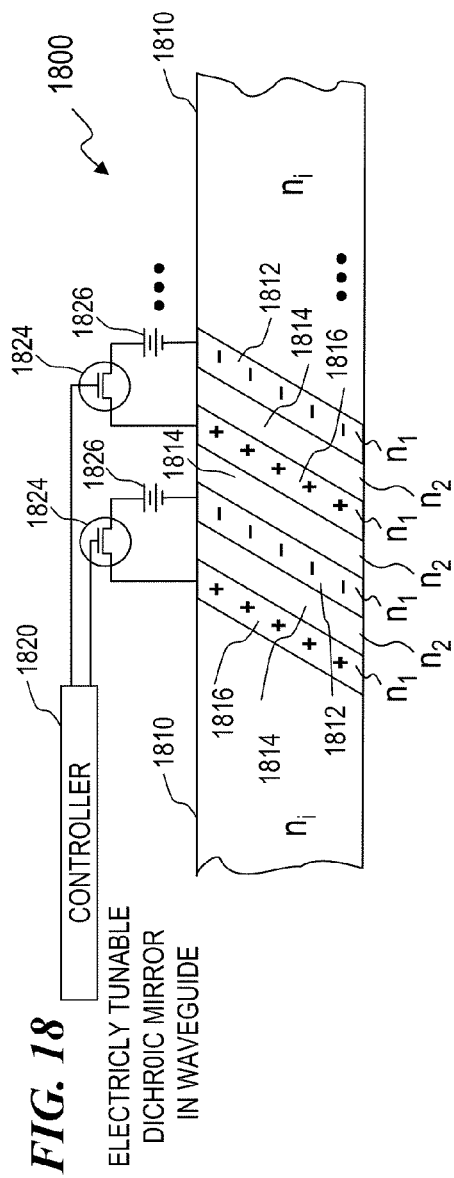
FIG. 18 is a schematic diagram of a wavelength-light-delivery system 1800 that is wavelength encoded with mirrors.

FIG. 18 is a schematic diagram of a wavelength-light-delivery system 1800 that is wavelength encoded with mirrors. In some embodiments, system 1800 includes a waveguide 1810 that has one or more dielectric-mirror stacks configured to selectively reflect desired wavelengths of light passing through waveguide 1810. In some embodiments, waveguide 1810 has an index of refraction $n_f$. In some embodiments, the one or more dielectric-mirror stacks include a plurality of transparent conductors having a first index of refraction $n_1$, wherein the transparent conductors are interleaved with a plurality of dielectric layers having a second index of refraction $n_2$. For example, in some embodiments, the one or more dielectric-mirror stacks include seven successively alternating layers of positively charged transparent conductors 1816, negatively charged transparent conductors 1812, and dielectric layers 1814 (e.g., a first positively charged transparent conductor 1816, followed by a first dielectric layer 1814, followed by a first negatively charged transparent conductor 1812, followed by a second dielectric layer 1814, followed by a second positively charged transparent conductor 1816, followed by a third dielectric layer 1814, followed by a second negatively charged transparent conductor 1812). In some embodiments, a voltage is applied to the transparent conductors 1816 and 1812 from voltage supply 1826 to stress the dielectric stack and thus change the wavelength of light to be reflected out of waveguide 1810. In some embodiments, the application of voltage across the dielectric-mirror stack is controlled by a controller 1820 that connects to the voltage supply 1826 via a transistor 1824 (e.g., in some embodiments, as shown in FIG. 18, each pair of positively charged conductor 1816 and negatively charged conductor 1812 has a voltage supply 1826 controlled by the controller 1820 via a transistor 1824). In some embodiments, transistor 1824 is a metal-oxide semiconductor field-effect transistor (MOSFET).

Figure 19:
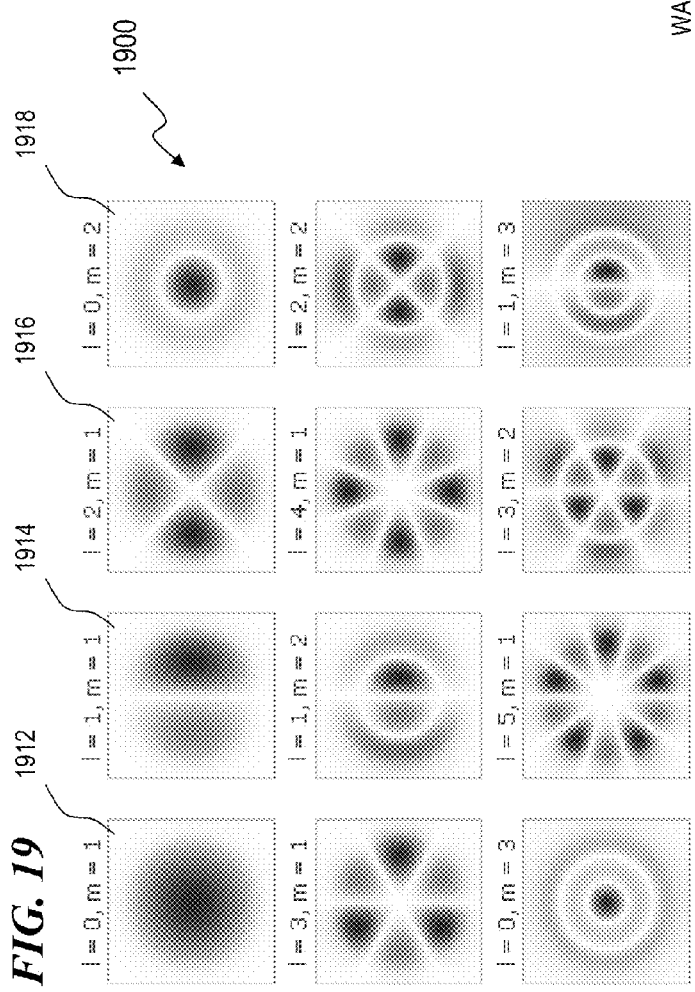
FIG. 19 is a diagram of a plurality of low-order fiber modes 1900 encoded by some embodiments of the waveguide light-delivery systems of the present invention.

FIG. 19 is a diagram of a plurality of low-order fiber modes 1900 encoded by some embodiments of the waveguide light-delivery systems of the present invention. In some embodiments, the set of solutions to a cylindrical waveguide form an orthogonal set of modes 1900, namely the $LP_{LM}$ modes. In some embodiments, the $LP_{LM}$ modes 1900 include $LP_{01}$ mode 1912, $LP_{11}$ mode 1914, $LP_{21}$ mode 1916, and $LP_{02}$ mode 1918. In some embodiments, because of the orthogonality of modes 1900, light launched into the $LP_{01}$ will not couple into any other mode. In some embodiments, light for each channel of the implanted waveguide light-delivery system is launched into a unique mode (e.g., in some embodiments, channel A is launched in $LP_{01}$ mode 1912, channel B is launched in $LP_{11}$ mode 1914, and channel C is launched in $LP_{21}$ mode 1916). In some such embodiments, the invention includes a mechanism for filtering modes.

Figure 20:
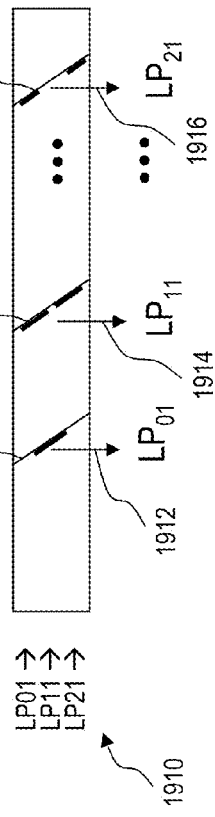
FIG. 20 is a schematic cross-section view of a waveguide light-delivery system 2000.

FIG. 20 is a schematic cross-section view of a waveguide light-delivery system 2000. In some embodiments, $LP_{LM}$ modes 1910 are launched into waveguide system 2000 and a unique $LP_{LM}$ mode is reflected out of waveguide system 2000 at each of a plurality of dielectric mirrors. For example, in some embodiments, $LP_{01}$ mode 1912 is reflected out by dielectric mirror 2022, $LP_{11}$ mode 1914 is reflected out by dielectric mirror 2024, and $LP_{21}$ mode 1916 is reflected out by dielectric mirror 2026.

Figure 21:
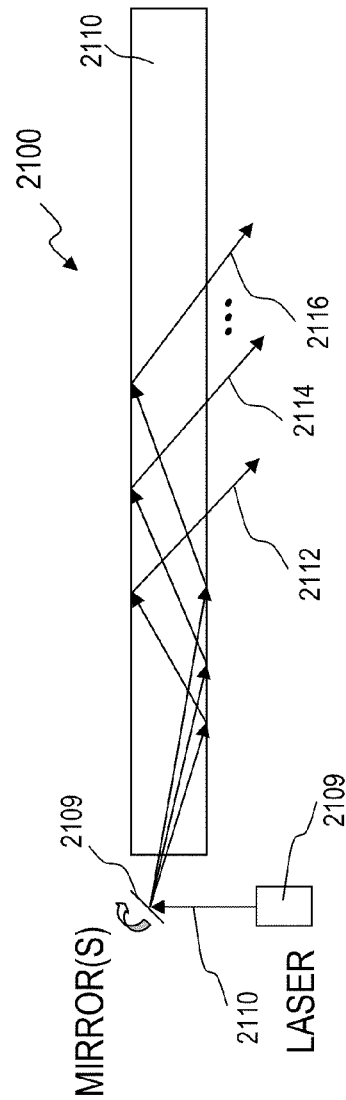
FIG. 21 is a schematic cross-section view of a high-order fiber-mode waveguide-light-delivery system 2100.

FIG. 21 is a schematic cross-section view of a high-order fiber-mode waveguide-light-delivery system 2100. In some embodiments, system 2100 includes a waveguide 2110. In some embodiments, higher-order modes are treated with ray tracing, unlike the low-order modes discussed in the description of FIG. 19 and FIG. 20 above. In some embodiments, channels (e.g., channels 2112, 2114, ... 2116) are encoded by launching light at different angles and/or locations. In some embodiments, a single laser 2109 with a mirror 2111, or other pointing adjustment element, is used to launch light at different angles.

Figure 22:
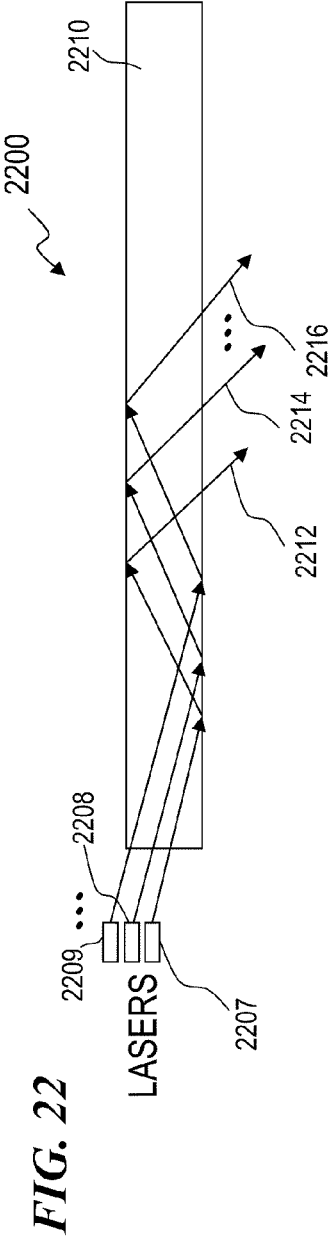
FIG. 22 is a schematic cross-section view of a high-order fiber-mode waveguide-light-delivery system 2200.

FIG. 22 is a schematic cross-section view of a high-order fiber-mode waveguide-light-delivery system 2200. In some embodiments, system 2200 includes a waveguide 2210. In some embodiments, system 2200 is substantially similar to system 2100 except that in system 2200, multiple lasers 2207, 2208, ... 2209, one for each channel 2212, 2214, ... 2216, are positioned at different angles and create an effect substantially similar to mirror 2111 of system 2100.

FIG. 23A is a perspective-view schematic diagram of a single fiber ribbon 2300 according to some embodiments of the present invention. In some embodiments, fiber ribbon 2300 includes a plurality of parallel waveguides 2310, each of which has a notch (e.g., notches 2311, 2312, 2313, 2314 and 2315) cut into it, wherein a face of the notch is highly reflective of the signal light in its waveguide 2310.

FIG. 23B is a side-view schematic diagram of single fiber ribbon 2300 according to some embodiments of the present invention. The light in at the left includes a separate signal for each waveguide 2310, wherein the light in a first waveguide 2310 is reflected as LIGHT $OUT_1$ by a reflector in notch 2311, the light in a second waveguide 2310 is reflected as LIGHT $OUT_2$ by a reflector in notch 2312, the light in a third waveguide 2310 is reflected as LIGHT $OUT_3$ by a reflector in notch 2313, the light in a fourth waveguide 2310 is reflected as LIGHT $OUT_4$ by a reflector in notch 2314.

FIG. 24A is a perspective-view schematic diagram of a fiber-array ribbon assembly 2410 having a plurality of fiber ribbons 2300 (including ribbon 2301, ribbon 2302, ribbon 2303) such as described above for FIG. 23A and FIG. 23B, according to some embodiments of the present invention. In some embodiments, ribbon 2301 is shorter than ribbon 2302, which is shorter than ribbon 2303 (as shown in FIG. 24C).

FIG. 24B is a plan-view schematic diagram of a VCSEL-array assembly 2420 having a plurality of VCSELs 2421 according to some embodiments of the present invention. While a four-by-four VCSEL array is shown here, the numbers of rows and columns corresponds to the numbers of ribbons 2300 and the number of waveguides 2310 per ribbon 2300, in some embodiments.

FIG. 24C is a plan-view schematic diagram of a VCSEL-ribbon-fiber array assembly 2400 having a fiber ribbon assembly 2410 and a VCSEL-array assembly 2420 according to some embodiments of the present invention. In some embodiments, the successive ribbons 2301, 2302, and 2303 (each having a plurality of emitting wedges) are longer than the ribbon inside it, thus providing a long extent of emitters on fine pitches, to provide fine granularity of frequency sensations.

FIG. 25A is a perspective-view schematic diagram of a subsystem 2501 according to some embodiments of the present invention. In some embodiments, subsystem 2501 includes an electrode-optrode device 120A having a single VCSEL 2520 surrounded by a ring electrode 2512 that, in some embodiments, is exposed on more than half its circumference at the tip of device 120A, but covered by an insulator 2515 for the rest of its circumference. In some embodiments, ring electrode 2512 is the exposed end of an electrical conductor 2513 (such as silver, copper, or other metal) that substantially surrounds the length of device 120A in a cylindrical manner, and is itself surrounded by a bio-compatible electrical insulator 2511 for the length of device 120A. In some embodiments, a second exposed electrode 2514 at or near the tip provides an electrical return path such that an electrical field (between electrode 2512 and electrode 2514 and extending into the nearby tissue of the patient) can be generated directly over the optical output face of VCSEL 2520. In some embodiments, the electrical connections to VCSEL 2520 are made using suitable connections to the ring electrode 2512 and auxiliary electrode 2516. Thus ring electrode 2512 provides both an electrical-stimulation electrode as well as an electrical contact to drive the optical signal from VCSEL 2520 (which, in some embodiments, is connected using flying-wire bonds 2517 and 2518 to electrical connections 2512 and 2516). In the embodiment shown, the additional electrical connection(s) 2516 and electrode(s) 2514 are connected to insulated conductors located inward from the circumferential conductor 2513 that connects to electrode 2512 and that provides shielding for the conductors within it. In some embodiments, the core of device 120A is a glass or polymer fiber 2510, and conductor 2513 is a metal film that is evaporated or plated or otherwise deposited on the circumference surface of fiber 2510, and then in turn coated with insulator 2511. In some embodiments, conductor 2513 does not completely surround the inner conductors that connect to electrode 2514 and VCSEL connection 2516, but has one or more lengthwise gaps. In some embodiments, the conductor connected to electrode 2514 is also a film deposited on fiber 2510 and separated from conductor 2513 by electrical insulation. In some such embodiments, the conductor connected to electrode 2514 is a film deposited concentrically, either inside or outside of conductor 2513 and separated therefrom by an insulator film. In the embodiment shown, the VCSEL 2520, mounted with its major face (its top in FIG. 25A) oriented perpendicular to the axis of fiber 2510, emits its optical stimulation signal in an axial direction (upward in FIG. 25A) from the end of fiber 2510, while in other embodiments, VCSEL 2520 is mounted at a non-perpendicular angle to the longitudinal axis of fiber 2510 (e.g., in some embodiments, at 45 degrees) such that it emits its light at a non-parallel angle (e.g., radially) to the axis of fiber 2510. In some embodiments, device 120A is used for the electrical-optical stimulation device 120 described in FIG. 1A and FIG. 1B.

FIG. 25B is a perspective-view schematic diagram of a subsystem 2502 according to some embodiments of the present invention. In some embodiments, subsystem 2502 includes electrode-optrode device 120B that includes a plurality of electrode-optrode devices 120A (such as described above for FIG. 25A), each of which is exposed at their ends but covered by an electrical insulator or one or more conductor-insulator pairs of films for the rest of the circumference of device 120B. In some embodiments, as shown in FIG. 25B, each of a plurality of electrode-optrode devices 120A have their operative stimulation ends at a common axial termination location, while in other embodiments, each of a plurality of electrode-optrode devices 120A have their operative stimulation ends at different axial termination locations (e.g., terminating and providing their respective stimulation at different longitudinal distances along the length of device 120B). In the embodiment shown, each VCSEL 2520, mounted with its major face (its top in FIG. 25B) oriented perpendicular to the longitudinal axis of device 120B, emits its optical stimulation signal in an axial direction (upward in FIG. 25B) from the end of device 120B, while in other embodiments, each VCSEL 2520 is mounted at a non-perpendicular angle to the axis of device 120B (e.g., in some embodiments, at 45 degrees) such that it emits its light at a non-parallel angle (e.g., radially) to the axis of fiber 2510.

FIG. 25C is a perspective-view schematic diagram of a subsystem 2503 according to some embodiments of the present invention. In some embodiments, subsystem 2503 includes electrode-optrode device 120C that includes a plurality of VCSEL emitters 2530, and an inner ring electrode 2534 and an outer ring electrode 2532 each of which is exposed at its end but covered by an electrical insulator 2531 and separated from one another by insulating layer 2535. In some embodiments, each of a plurality of VCSELs 2530 are mounted between electrodes 2532 and 2534, and use one or both electrodes 2532 and 2534 as electrical connections to receive electrical power to activate the VCSEL. In some embodiments, a plurality of signal connections (not shown) is used to turn on each VCSEL independently. In some embodiments, a central insulating fiber core 2536 is used, wherein a metal conductor (e.g., a film) 2534 is plated or otherwise deposited on the fiber core 2536, then an insulating layer 2533 is deposited and another metal conductor (e.g., a film) 2532 is plated or otherwise deposited on the insulator 2532, then an outer bio-compatible insulating layer 2531 is deposited. The electric sensitization field is formed between the exposed ends (electrodes) 2532 and 2534.

FIG. 25D is a perspective-view schematic diagram of a subsystem 2504 according to some embodiments of the present invention. In some embodiments, subsystem 2504 includes electrode-optrode device 120D that includes a plurality of VCSEL emitters 2540, and split outer ring electrode including half ring electrode 2544 and half ring electrode 2542 each of which is exposed at its end but covered by an outer electrical insulator and separated from one another by insulating layer 2549. In some embodiments, each of a plurality of VCSELs 2540 are mounted in a central area between electrodes 2542 and 2544, and use one or both electrodes 2542 and 2544 as one of their electrical connections to receive electrical power to activate the VCSEL. In some embodiments, a plurality of signal connections 2516 (the ends of which are shown) is used to turn on each VCSEL independently. In some embodiments, a central insulating fiber core 2536 (as in FIG. 25C) is used, wherein a metal conductors (e.g., a film) 2544 is plated or otherwise deposited on the right-hand half of fiber core 2536, another metal conductor (e.g., a film) 2542 is plated or otherwise deposited on the left-hand half of fiber core 2536, then an outer bio-compatible insulating layer 2531 (not labeled here, but as shown in FIG. 25C) is deposited. The electric sensitization field is formed between the exposed ends (electrodes) 2542 and 2544.

Figure 25F:
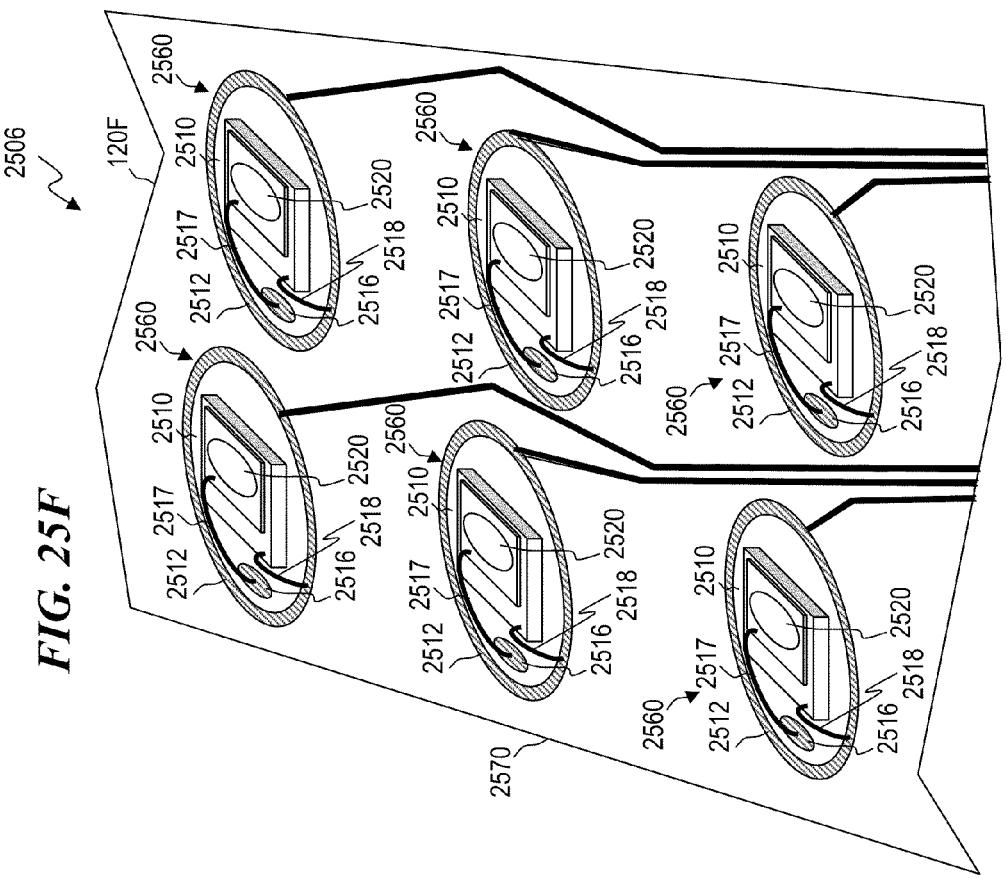
FIG. 25F is a perspective-view schematic diagram of a subsystem 2506 according to some embodiments of the present invention.
Figure 25E:
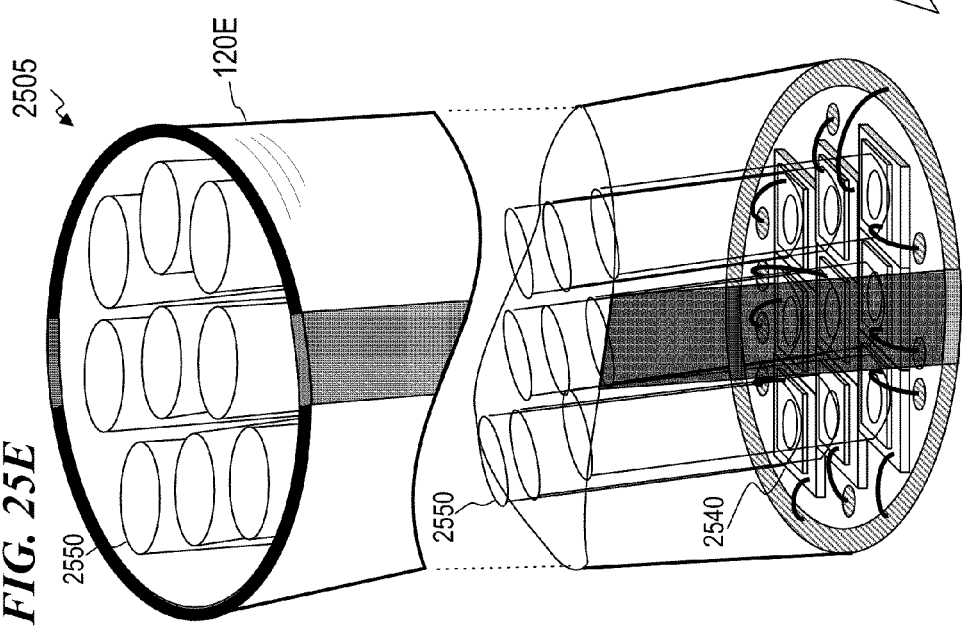
FIG. 25E is a perspective-view schematic diagram of a subsystem 2505 according to some embodiments of the present invention.

FIG. 25E is a perspective-view schematic diagram of a subsystem 2505 according to some embodiments of the present invention. In some embodiments, subsystem 2505 includes a plurality of VCSELs 2540 in a configuration such as shown in FIG. 25D, but at the distal end of the device relative to the light-emitting ends of optical fibers 2550, which transport light from the emitting ends of VCSELs 2540 to the tissue being stimulated.

FIG. 25F is a perspective-view schematic diagram of a subsystem 2506 according to some embodiments of the present invention. In some embodiments, subsystem 2506 includes a ribbon substrate 2570 on which a plurality of VCSEL assemblies 2560 are placed in an array (the array extending for a length and across a width of substrate 2570. In some embodiments, each assembly 2560 includes a mounting surface 2510 having one or more VCSELs 2520, and surrounded by a ring electrode 2512. Each VCSEL 2520 has a wire 2517 to an electrical connection 2516 to activate it (in some embodiments, each uses the ring electrode 2512, connected by wire 2518, as the other electrical contact)

Figure 26:
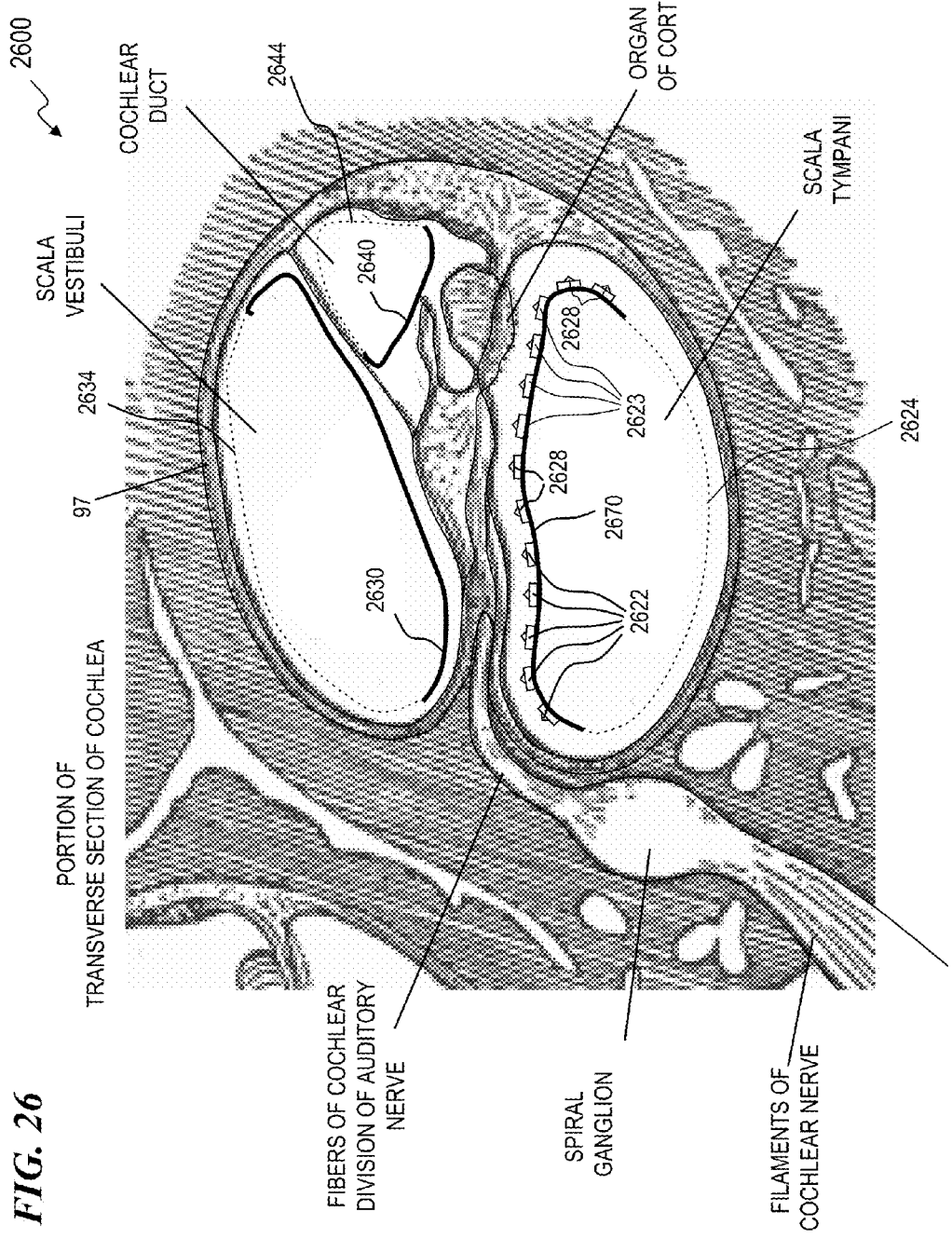
FIG. 26 is a perspective-view schematic diagram of a subsystem 2600 according to some embodiments of the present invention.

FIG. 26 is a perspective-view cross-section schematic diagram of a subsystem 2600 according to some embodiments of the present invention. In some embodiments, subsystem 2600 includes an electrical-optical stimulation system (such as subsystem 2506 of FIG. 25F) having a first substrate 2670 (like ribbon substrate 2570 of FIG. 25F) on which a plurality of electro-optical stimulation units (2622, 2628, 2623, each substantially like VCSEL assemblies 2560 of FIG. 25F) are located. In some embodiments, first substrate 2670 is located in the scala tympani of the cochlea. In some embodiments, a soft pliable assembly 2624 presses substrate 2670 and its stimulation units (2622, 2628, 2623) against the excitable tissue (comprised of the organ of Corti and/or the spiral ganglion cells that extend from it to the filaments of the cochlear nerve). In some embodiments, a soft pliable assembly 2634 presses substrate 2630 against the opposite side of the excitable tissue (e.g., against the neurons extending from the organ of Corti to the filaments of the cochlear nerve), and/or a soft pliable assembly 2644 presses substrate 2640 against the opposite side of the excitable tissue (e.g., against the organ of Corti and/or the neurons extending from the organ of Corti to the filaments of the cochlear nerve). In some embodiments, a second substrate 2630 located in the scala vestibuli and/or third substrate 2640 located in the cochlear duct are used to support the electrodes providing an electrical return path for the electrical signal provided by the ring electrodes of stimulation units (2622, 2628, 2623). In some embodiments, a plurality of return electrodes (e.g., striped across a width of the respective substrates 2630 and 2640) are provided.

Thermal Management:

In some embodiments, a substrate is used as a heat sink. In some such embodiments, the substrate/heat sink extends outside of the round window. In some embodiments, heat generated by optical source is used to power electronics (e.g., a pyro-electric thin film). In other embodiments, electricity is possibly generated by a device that interacts with its surrounding biological tissue (e.g., extracting energy from ATP).

In some embodiments, a substrate-extension design is used to spread heat out of cochlear so as to implement maximum amount of channels without exceeding the temperature rise limit (e.g., 2° Celsius). In some such embodiments, this includes application of high thermal conductivity materials such as carbon nanotubes (CNT) and unique insulation/coating design (e.g., see FIG. 3's implant housing heatsink 131). In some embodiments, the substrate design converts heat to electricity to power up electrodes (full or partially) for hybrid integrated nerve-stimulator implant (see FIG. 29).

VCSEL Hermetically-Sealed Packaging and Process:

In some embodiments, the micro-lens and sub-mount design to allow wafer-level packaging and dicing of a hermetically-sealed package.

In some embodiments, anti-reflective (AR) coatings are used on at least a portion of the hermetically-sealed package (see FIG. 37) to ensure 95% or better transmittance (e.g., coatings on optical window 628 of FIG. 6).

Figure 36:
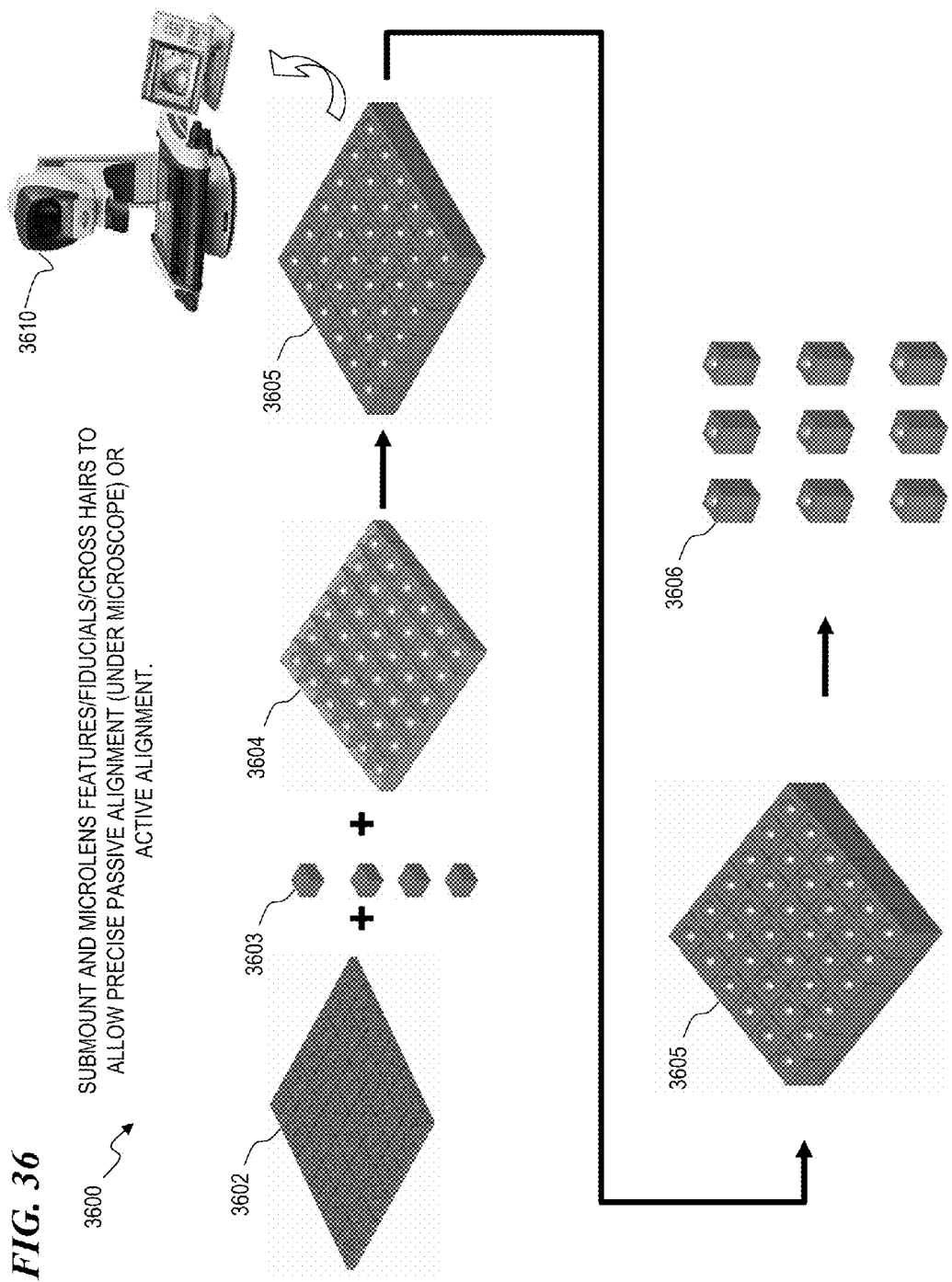
FIG. 36 is a flow diagram 3600 according to some embodiments of the present invention.

In some embodiments, the hermetically-sealed packaging design includes sub-mount and micro-lens features/fiducials/cross hairs to allow precise passive alignment (under microscope) or active alignment (see the description of FIG. 36).

In some embodiments, the hermetically-sealed packaging design allows fast hermeticity examination by optical leak testing, mainly by unique wall thickness, package aspect ratio, or necessary features such as "testing windows" (see the description of FIG. 37)

In some embodiments, other potential hermeticity test methods can be used, for example:
1) helium sensor chip in place of VCSEL inside dummy package to measure helium leaked in directly instead of trying to measure from outside;
2) die bond humidity sensor chip in place of VCSEL to measure humidity leak rate (this is not a direct measure of hermeticity, but it simulates the use environment);
3) rely on live VCSEL test in accelerated stressed environment such as high pressure high humidity (this is a direct measurement of the reliability of VCSEL package and need theory correlate the test time to equivalent life time).

Beam Steering/Beam-Shaping Designs:

In some embodiments, the present invention provides an optical-simulation device that includes a digital light projector chip (many individually tiltable mirrors) to steer and/or shape the optical beam (e.g., DLP®-type projection system). In some embodiments, a MEMS (micro-electro-mechanical systems) device having a plurality of movable mirrors (such as described in, e.g., U.S. Pat. No. 4,596,992 to Hornbeck and U.S. Pat. No. 7,787,170 to Patel et al., which are both incorporated herein by reference) is activated to switch or move the mirrors into or out of the beam path, or otherwise deflect the optical signals to selectively stimulate neurons.

In some embodiments, MEMS units having a plurality of electrically activatable or controllable mechanical actuators are use to adjust positions of light emitters or light-guiding elements (moving optical fibers, lenses, mirrors or other light-guiding elements) in the array. In some embodiments, the device controls mirrors with piezoelectric material to 'move' the mirrors, while in other embodiments, electrostatic or other means are used.

In some embodiments, the MEMS actuators are used to change the relative position of the VCSEL and/or the lens/mirror. In some embodiments, the MEMS actuators are used to change mechanical positioning of lenses. In some embodiments, the MEMS actuators are used to change mechanical positioning of the VCSEL. In some embodiments, piezo material is used to electrically control beam direction. In some such embodiments, the piezo material is embedded in substrate.

In some embodiments, one or more lenses are used to shape optical beam (e.g., collimated, focused, unfocussed/divergent). In some such embodiments, the lens is intrinsic to VCSEL. In other such embodiments, the lens is extrinsic to VCSEL.

Some embodiments use a biocompatible silicon coating shaped to be a lens to enclose the VCSEL (i.e., transparent to wavelength for stimulation—e.g., 1850 nm).

Figure 27A:
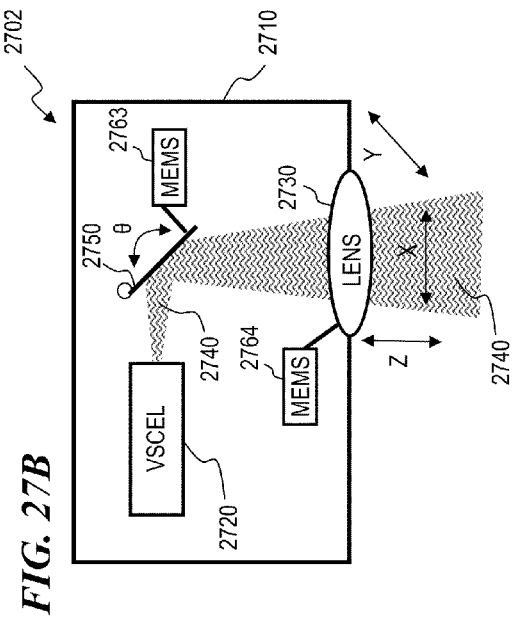
FIG. 27A is a schematic block diagram of nerve stimulator 2701, according to some embodiments of the present invention.

FIG. 27A is a schematic block diagram of nerve stimulator 2701, according to some embodiments of the present invention. In some embodiments, nerve stimulator 2701 includes package 2710. In some such embodiments, nerve stimulator 2701 steers and/or shapes the VCSEL beam 2740 to a selected nerve external to the package 2710 to increase effectiveness (i.e., its effectiveness in obtaining triggering of NAPs in a particular nerve pathway; note that identifying which nerve pathway need not be physically measured, since it is the resulting sensation that is important to the patient, and the sensation can be stimulated and detected or reported by the patient, so it will then be assumed that the appropriate NAP was triggered in one or more neurons of the appropriate nerve pathway). In some embodiments, the VCSEL beam generator 2720 is movable in one or more of the X, Y, and Z directions to steer and/or shape the VCSEL beam 2740. In some such embodiments, a MEMS activator 2761 is used to move the VCSEL beam generator 2720 in one or more of the X, Y, and Z directions. In some embodiments, the lens 2730 is movable in one or more of the X, Y, and Z directions to steer and/or shape the VCSEL beam 2740. In some such embodiments, a MEMS activator 2762 is used to move the lens 2730 in one or more of the X, Y, and Z directions. In some embodiments, both the VCSEL beam generator 2720 and the lens 2730 are movable in one or more of the X, Y, and Z directions to steer and/or shape the VCSEL beam 2740.

Figure 27B:
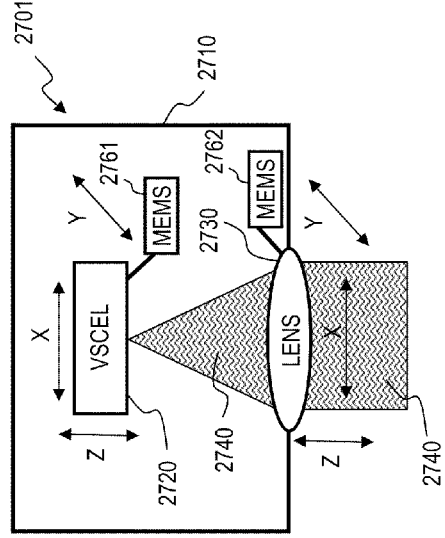
FIG. 27B is a schematic block diagram of nerve stimulator 2702, according to some embodiments of the present invention.

FIG. 27B is a schematic block diagram of nerve stimulator 2702, according to some embodiments of the present invention. In some embodiments, nerve stimulator 2702 includes package 2710. In some such embodiments, nerve stimulator 2702 steers and/or shapes the VCSEL beam 2740 on a nerve external to the package 2710 to increase effectiveness. In some embodiments, a mirror 2750 is rotatable to change the angle θ to steer and/or shape the VCSEL beam 2740. In some such embodiments, a MEMS activator 2763 is used to rotate the mirror 2750. In some embodiments, the lens 2730 is movable in one or more of the X, Y, and Z directions to steer and/or shape the VCSEL beam 2740. In some such embodiments, a MEMS activator 2764 is used to move the lens 2730 in one or more of the X, Y, and Z directions. In some embodiments, both the mirror 2750 is rotatable and the lens 2730 are movable in one or more of the X, Y, and Z directions to steer and/or shape the VCSEL beam 2740.

Figure 27C:
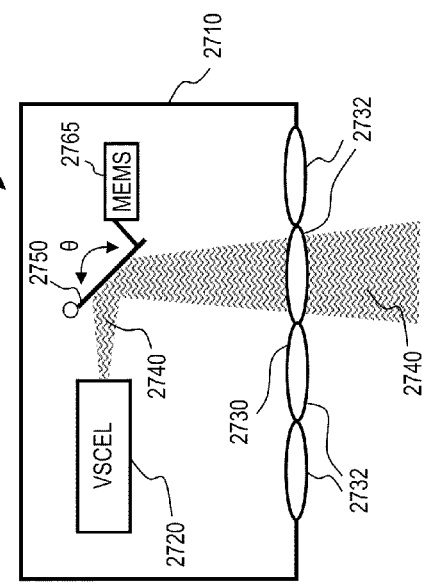
FIG. 27C is a schematic block diagram of nerve stimulator 2703, according to some embodiments of the present invention.

FIG. 27C is a schematic block diagram of nerve stimulator 2703, according to some embodiments of the present invention. In some embodiments, nerve stimulator 2703 includes package 2710. In some such embodiments, nerve stimulator 2703 steers and/or shapes the VCSEL beam 2740 on a nerve external to the package 2710 to increase effectiveness. In some embodiments, a mirror 2750 is rotatable (using MEMS 2765) to change the angle θ to steer and/or shape the VCSEL beam 2740 toward one or more lens of an array of lens 2732.

Figure 28:
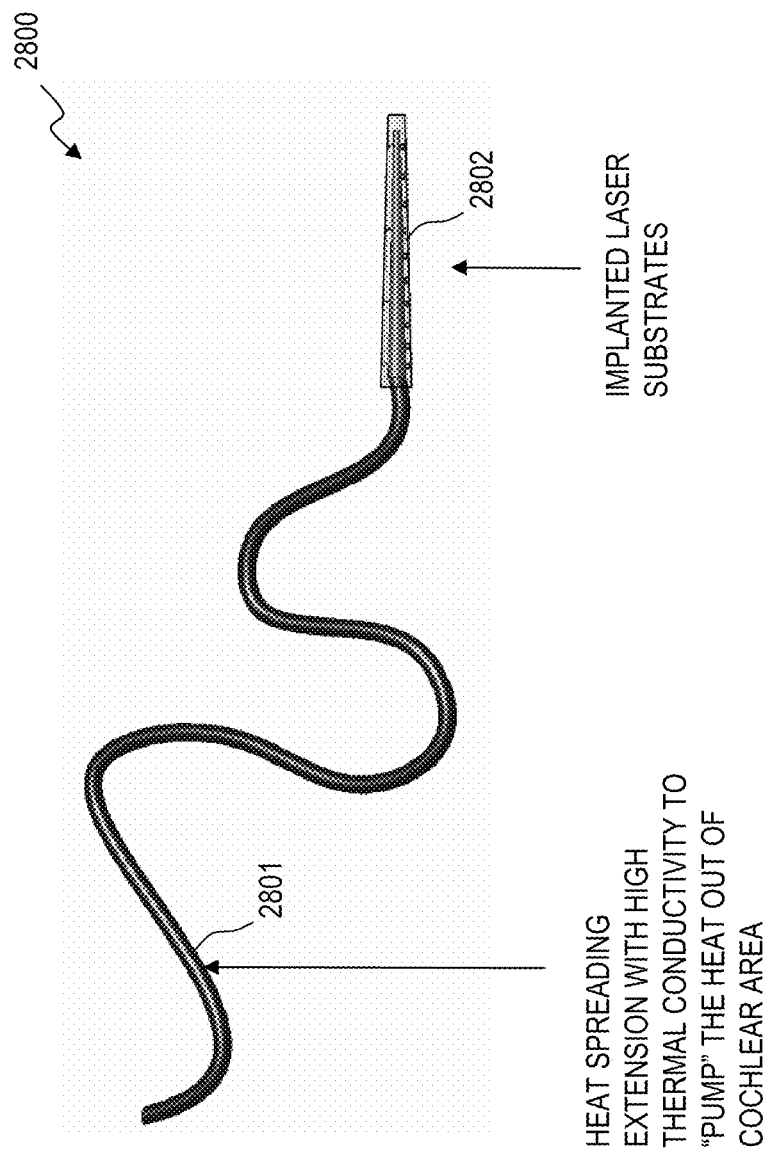
FIG. 28 is a perspective-view schematic diagram of a heat-spreader extension design 2800 according to some embodiments of the present invention.

FIG. 28 is a perspective-view schematic diagram of a heat-spreader extension device 2800 according to some embodiments of the present invention. In some embodiments, device 2800 includes a plurality of heat-generating electrical and optical components on the active portion 2801 (e.g., the portion that would be implanted inside or adjacent the cochlea), and a heat-spreading highly thermally conductive portion 2801 (e.g., a ribbon that extends 10 cm or longer) to dissipate the heat over a greater volume of the patient's body, in order to minimize the temperature rise. In some embodiments, the highly thermally conductive portion 2801 is implanted next to the skin under the scalp of the patient to readily dissipate heat external to the patient's body.

Figure 29:
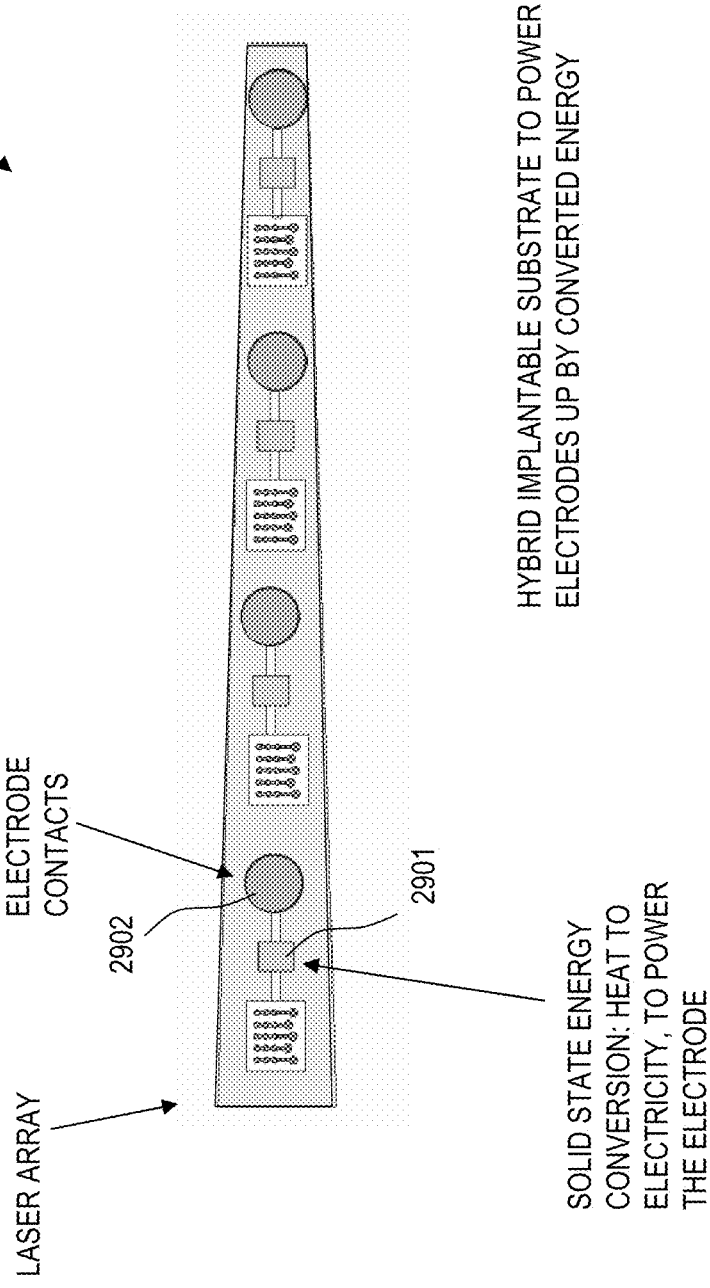
FIG. 29 is a schematic diagram of a hybrid implantable substrate 2900 according to some embodiments of the present invention.

FIG. 29 is a schematic diagram of a hybrid implantable substrate 2900 according to some embodiments of the present invention. In some embodiments, hybrid implantable substrate 2900 includes a plurality of heat-to-electricity transducers 2901 that convert body heat (e.g., a temperature difference between the body's core temperature on the inside face of device 2900 (facing the core of the body) and the opposite outer face of device 2900 (facing the skin of the body). In some embodiments, electrode contacts 2902 are provided (in some embodiments, used to provide one or more of the electrodes for electrical stimulation). In some embodiments, a plurality of VCSEL arrays 1405 such as described above in FIG. 14A and FIG. 14B are used.

Figure 30:
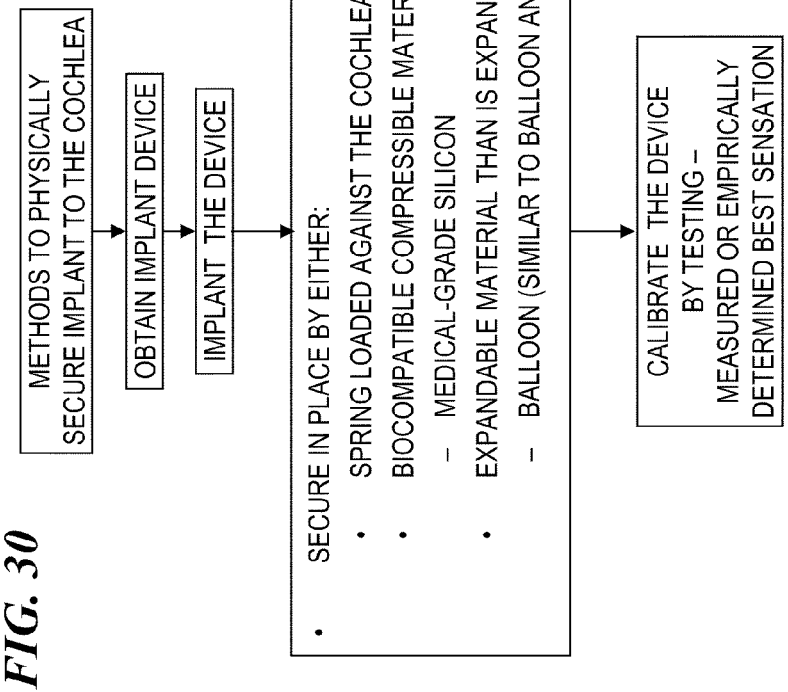
FIG. 30 is a flow diagram of methods to physically secure implant to the cochlea 3000 according to some embodiments of the present invention.

FIG. 30 is a flow diagram of methods to physically secure implant to the cochlea 3000 according to some embodiments of the present invention. In some embodiments, the methods 3000 include obtaining an implant device (i.e., the stimulation device to be implanted), implanting the device (placing it where desired) and then securing it in place (e.g., via a spring-loaded substrate that presses the active emitters against the tissue to be stimulated, or via a biocompatible resilient and/or compressible material on the "back side" of implant substrate (against cochlear wall opposite the excitable tissue (e.g., soft medical-grade silicone (either pre-cured in the desired shape, or injected as a gel or liquid to cure in place) that presses against an opposite wall so the side facing the active substrate presses it against the excitable tissue), or a balloon or other expandable material that is expanded after implant (e.g., in some embodiments, balloon (similar to balloon angioplasty) or stent (similar to arterial-stent implantation).

Figure 31:
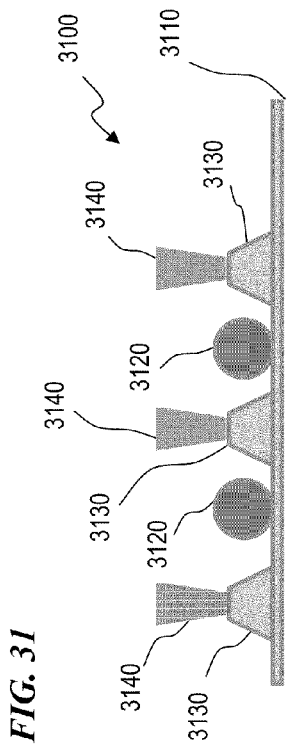
FIG. 31 is a block diagram of beam pointing control system 3100, according to some embodiments of the present invention.

FIG. 31 is a block diagram of beam pointing control system 3100. In some embodiments, beam pointing control system 3100 includes substrate 3110 with integrated shape changing material (or smart material) 3120 so that it manipulates beam pointing to maximize stimulation after implant insertion. U.S. Patent Application Publication 2010/0162109 to Chatterjee et al. published Jun. 24, 2010 titled "USER INTERFACE HAVING CHANGEABLE TOPOGRAPHY" (incorporated herein by reference) describes a shape-shifting device. In some embodiments, the In some embodiments, a shape-shifting device such as described by Chatterjee et al. is used in the present invention, which provides a substrate 3110 (that is shape-changed as per Chatterjee et al.), and that has a plurality of optical emitters 3130, each optionally and controllably emitting light 3140. In some embodiments, the substrate 3110 is also with embedded piezoelectric fiber strands 3120 that, by applying a voltage, will curl the substrate to conform to the shape of the cochlea of the patient 99. This makes it possible to produce the substrate in a flat form, easing fabrication and/or implantation in the patient 99. In some other embodiments, a layer of piezoelectric material is deposited on the substrate to accomplish the function of shaping the substrate to maintain beam-pointing directionality/stability. In some embodiments, the length of the flexible region of the substrate 3110 is minimized to limit twisting.

Figure 32:
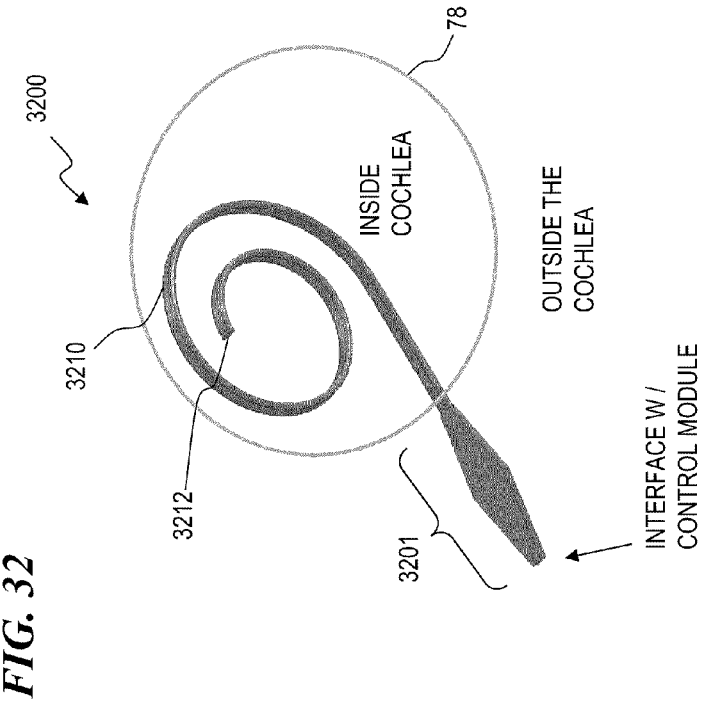
FIG. 32 is a perspective view of a cochlear implant system 3200 designed for improved cooling, according to some embodiments of the present invention.

FIG. 32 is a perspective view of a cochlear implant system 3200 designed for improved cooling of the active devices. In some embodiments, substrate 3210 includes integrated graphite fibers or carbon-nanotube-based fibers to spread the heat from the substrate 3210, including up to the tip 3212, from inside cochlea 78 to outside of cochlea 78. In some embodiments, carbon fiber is molded in biocompatible material such as polyimide, and/or coated with biocompatible coating such as thin film, pin-hole free parylene conformal coatings. In some embodiments, the carbon fiber is also laminated in layers. In some such embodiments, the heat spreading materials is extended outside of cochlear to meet the cooling needs. Once out side of cochlear, the substrate 3240 is, in some embodiments, spread over a larger area to maximize its cooling area. In some embodiments, the heat spreading area is further increased by separating the carbon fibers from each other (each with a biocompatible coating, such as thin-film pin-hole-free parylene conformal coatings).

Figure 34:
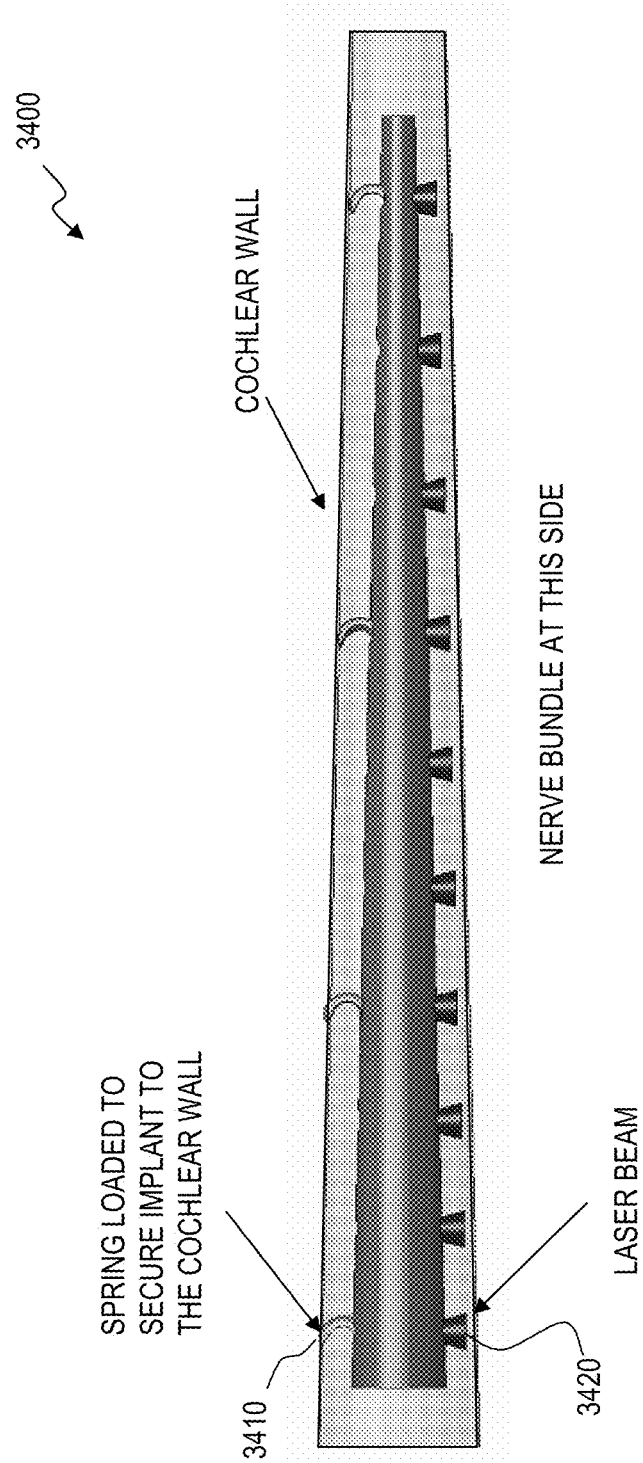
FIG. 34 is a stimulation system 3400 configured to be implanted within the cochlea of a living subject (e.g., a human) according to some embodiments of the present invention.

FIG. 33 is a flow diagram of methods of substrate-level packaging 3000 according to some embodiments of the present invention. In some embodiments, the substrate is designed to ensure short distance between laser source and cochlear nerve bundle for all lasers consistently, which will result in lower laser energy requirement, and still achieve adequate stimulation. For safety and thermal management consideration, close proximity minimizes laser energy needed to stimulate NAPS. In some embodiments, the substrate topology design is "cone" shaped to maintain close proximity to the excitable tissue FIG. 34 is a plan view of a stimulation system 3400 (having a plurality of opto-electrical stimulations units 3420, each configured to selectively activate and emit a laser beam, and optionally also provide electrical sensitization) configured to be implanted, and secured using hooks 3410, within the cochlea of a living subject (e.g., a human) according to some embodiments of the present invention.

Figure 35:
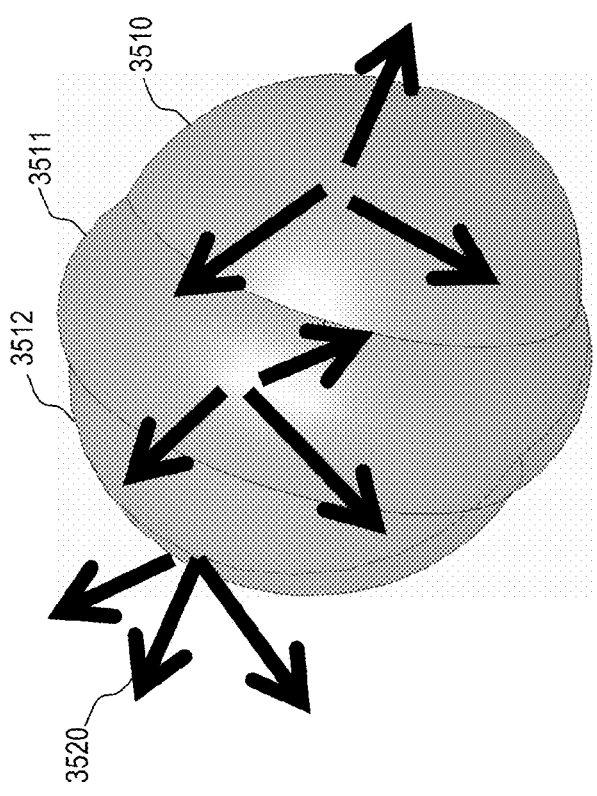
FIG. 35 is a perspective-view of a variable-curvature lens design 3500 according to some embodiments of the present invention.

FIG. 35 is a perspective-view of a variable-curvature lens design 3500 according to some embodiments of the present invention. In some embodiments, the lens 3500 includes a plurality of lens surfaces 3510, 3511, and 3512, each of which emits a light beam or pattern 3520 (e.g., conically and/or axially for lens surfaces 3512 and 3510, and radially for lens surface 3511.

FIG. 36 is a flow diagram 3600 according to some embodiments of the present invention. In some embodiments, a VCSEL wafer 3602 having a plurality of VCSELS implemented there on is joined (optionally using spacers 3603) to a wafer-like array of lenses 3604 (aligned, e.g., using a microscope 3610) to form a VCSEL-lens assembly 3605. This is then diced into a plurality of VCSEL-lens units 3606, each including one or more independent VCSELs and one or more lenses.

FIG. 37 is a block diagram of leak testing system 3700, according to some embodiments of the present invention. In some embodiments, device 3720 is tested in a sealed pressurized helium-filled chamber, and a laser beam 3701 is directed against a mirror 3710 to reflect from device 3720. If helium has leaked (in or out of the device 3720), the index of refraction changes and the beam will deflect from its normal path. This allows manufacturing to distinguish devices that are not hermetically sealed from those that are hermetically sealed. This data is used to select good devices and/or to adjust the manufacturing process to fix the problem.

FIG. 38 is a stimulation system 3800 configured to be implanted within the cochlea of a living subject (e.g., a human) according to some embodiments of the present invention. Some embodiments include a plurality of optical-stimulation light emitters 3810 distributed in a non-uniform linear pattern on the substrate of device 3800, wherein some emitters are spaced nearer to their nearest neighbors and others of the emitters are spaced further from their nearest neighbors. For example, in some embodiments, a substantially logarithmic spacing pattern is used such that the spacings between nearest-neighbor emitters differ and the spacing distances follow a logarithmic curve. In addition, some embodiments include a first emitter-spacing density in a first hearing-frequency range that is relatively less necessary for speech understandability, and a second emitter-spacing density (more dense than the first density) in a second hearing-frequency range that is relatively more necessary for speech understandability. Note that in conventional implanted multiple-electrode cochlear-stimulation devices, the electrodes are spaced with a uniform spacing (the center-to-center and the edge-to-edge spacing between each electrode and its nearest neighboring electrodes is substantially constant for all electrodes. Such conventional multiple-electrode cochlear-stimulation devices use a constant electrode-electrode spacing due to constraints imposed by electric field or electrical current spreading (if different edge-to-edge spacings were to be used, the electric fields would have different (volts-per-mm) values). One goal of conventional devices is to place as many electrical-stimulation channels as possible to increase the number of frequency bands the device can stimulate; however if too many channels are located along a length, they will be too close to one another and the electric signal between adjacent electrodes will overlap to the extent that the channels will not be capable of independently stimulating closely spaced frequency bands resulting in a loss of resolution frequency and/or loudness content of the audio signal. The spacing in such conventional devices is constrained in order to achieve the highest number of stimulation areas, while limiting the detrimental effect caused by electrical spreading as the electrodes are positioned closer together.

FIG. 39 is a diagram of methods 3900 to physically secure an implant to the cochlea according to some embodiments of the present invention. In some embodiments, a stent-like device 3910 (SEMS (self expandable metal stent) to fix a fiber or VCSEL substrate 3920 to the cochlear wall. In some embodiments, the fiber/substrate is oriented for light delivery to the nerve being stimulated.

In some embodiments, the present invention provides a method for stimulating neurons (central or peripheral projections) of the cochlea or the auditory brainstem or midbrain of a patient to provide auditory sensations for the patient. This method includes delivering light signals to a plurality of neurons of the auditory brainstem or midbrain of the patient. In some embodiments, a concurrent application of electrical stimulation sensitizes the nerves in order that a smaller amount of optical energy can be used to still obtain a NAP that otherwise would require a larger amount of optical energy.

In some embodiments, the delivering of light signals includes delivering the light signals to peripheral projections of the neurons. In some embodiments, the delivering of light signals includes delivering the light signals to central portions of the neurons.

In some embodiments, the delivering of light signals includes delivering infrared light from a laser. In some embodiments, the delivering of light signals includes delivering infrared light from a VCSEL.

Some embodiments further include delivering an electrical signal to a plurality of neurons of the auditory brainstem or midbrain of the patient.

In some embodiments, the delivering of the light signals includes obtaining a plurality of light signals from one or more laser light sources and delivering the obtained light signals to discrete portions of excitable tissues, wherein the responses triggered by the light signals are interpretable by the patient's brain as sensory responses.

In some embodiments, the delivering of the light signals further includes selectively controlling the light signals to optically stimulate the neurons in order to control nerve action potentials (NAPs) produced by the one or more nerves. In some embodiments, the selectively controlling the light signals includes controlling a pulse width of the plurality of light signals. In some embodiments, the selectively controlling the light signals includes controlling a pulse repetition rate of the plurality of light signals. In some embodiments, the selectively controlling the light signals includes controlling a pulse shape of the plurality of light signals. In some embodiments, the selectively controlling the light signals includes controlling a DC background amount of light intensity of the plurality of light signals. In some embodiments, the selectively controlling the light signals includes controlling a precharge amount of light intensity followed by a trigger amount of light intensity of the plurality of light signals. In some embodiments, the selectively controlling the light signals includes controlling the light signals to increase a frequency of the NAPs produced by the one or more nerves that would otherwise occur without the plurality of light signals.

In some embodiments, the method further includes applying a precharge current of electrical energy that is followed by a trigger amount of pulsed light intensity of the plurality of light signals.

In some embodiments, the obtaining the plurality of light signals includes implanting a self-contained battery-powered laser-light-generation device and obtaining the plurality of light signals from the battery-powered laser-light-generation device.

In some embodiments, the delivering the plurality of light signals to the plurality of neurons of the auditory brainstem or midbrain includes positioning a delivery end of one or more fibers against one or more neurons of the auditory brainstem or midbrain and using one or more optical fibers to guide the light signals from a laser source to the one or more neurons.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

Some embodiments further include sensing one or more conditions that affect balance, and wherein the selectively controlling the plurality of light signals to the brainstem or midbrain includes controlling the light signals, at least partly based on the sensed one or more conditions that affect balance, to provide a sense-of-balance nerve stimulation. In some such embodiments, the sensing of the one or more conditions that affect balance includes monitoring eye movements.

Some embodiments further include sensing one or more sounds, and wherein the selectively controlling the plurality of light signals includes controlling the light signals to the brainstem or midbrain, at least partly based on the sensed sounds, to provide a sense-of-hearing nerve stimulation.

In some embodiments, the present invention provides a method that includes obtaining a plurality of light signals from one or more laser light sources; delivering the plurality of light signals to a plurality of nerve pathways in the brainstem or midbrain of a living animal; and selectively controlling the plurality of light signals to optically stimulate the plurality of nerve pathways in order to control nerve action potentials (NAPS) produced by the plurality of nerve pathways. In some embodiments, the plurality of nerve pathways in the brainstem or midbrain includes auditory nerve pathways. In some embodiments, the plurality of nerve pathways in the brainstem or midbrain includes sense-of-balance nerve pathways.

In some embodiments, the living animal is a human person. In some embodiments, the living animal is a large non-human animal, e.g., a race horse or dairy cow. In some embodiments, the living animal is a small non-human animal, e.g., a dog, cat, rodent or the like.

In some embodiments, the selectively controlling the light signals includes controlling a pulse width of the plurality of light signals.

In some embodiments, the selectively controlling the light signals includes controlling a duty cycle of the plurality of light signals.

In some embodiments, the selectively controlling the light signals includes controlling an on-time and an off-time of the plurality of light signals.

In some embodiments, the selectively controlling the light signals includes controlling a wavelength of the plurality of light signals.

In some embodiments, the selectively controlling the light signals includes controlling a pulse repetition rate of the plurality of light signals.

In some embodiments, the selectively controlling the light signals includes controlling a pulse shape of the plurality of light signals.

In some embodiments, the selectively controlling the light signals includes controlling a minimum light intensity and a maximum light intensity of the plurality of light signals.

In some embodiments, the present invention provides a combination of electrical and optical stimulation.

In some embodiments, the selectively controlling the light signals includes controlling a DC background amount of light intensity of the plurality of light signals.

In some embodiments, the present invention provides a combination of electrical and optical stimulation. In some embodiments, the method further includes selectively controlling and applying to one or more tissues of the animal one or more electrical signals (i.e., hybrid electrical and optical stimulation of one or more tissues). In some embodiments, the selectively controlling and applying the electrical signal(s) includes controlling and applying a DC background amount of electrical signal. In some embodiments, the selectively controlling and applying the electrical signal(s) includes applying electrical pulses.

In some embodiments, the selectively controlling the light signals includes controlling a precharge amount of light intensity followed by a trigger amount of light intensity of the plurality of light signals.

In some embodiments, the selectively controlling the light signals includes controlling the light signals to delay at least some of the NAPS produced by the one or more nerves that would otherwise occur without the plurality of light signals.

In some embodiments, the selectively controlling the light signals includes controlling the light signals to increase a frequency of the NAPs produced by the one or more nerves that would otherwise occur without the plurality of light signals.

In some embodiments, the selectively controlling the light signals includes controlling the light signals to decrease a frequency of the NAPs produced by the one or more nerves that would otherwise occur without the plurality of light signals.

In some embodiments, the obtaining the plurality of light signals includes implanting a self-contained battery-powered laser-light-generation device.

In some embodiments, the plurality of light signals includes implanting self-contained infrared (IR) laser device.

In some embodiments, the delivering the plurality of light signals to one or more nerves of each of one or more inner-ear vestibular organs includes using one or more optical fibers to guide the light signals.

In some embodiments, the delivering the plurality of light signals to one or more nerves of each of one or more inner-ear vestibular organs includes positioning a delivery end of one or more fibers against a vestibular organ and using the one or more optical fibers to guide the light signals from a laser source to the vestibular organ.

In some embodiments, the one or more laser light sources include a first light source and a second light source, wherein the selectively controlling the plurality of light signals includes controlling the first light source to send a first series of pulses during a first period of time and controlling the second light source to send a second series of pulses during the first period of time, and wherein the first series of pulses differs from the second series of pulses in repetition rate.

In some embodiments, the present invention provides a method further including sensing one or more conditions that affect balance, and wherein the selectively controlling the plurality of light signals includes controlling the light signals, at least partly based on the sensed one or more conditions that affect balance, to provide a sense-of-balance nerve stimulation.

In some embodiments, the sensing of the one or more conditions that affect balance includes sensing motion and orientation.

In some embodiments, the sensing the one or more conditions that affect balance includes monitoring muscular stimulation.

In some embodiments, electrical stimulation delivered via nerves connected to muscles is sensed. In some embodiments, the result of the muscular movement is sensed.

In some embodiments of the invention, monitoring muscular stimulation includes monitoring eye movements.

In some embodiments, electrical stimulation delivered via nerves connected to eye muscles is sensed. In some embodiments, the eye movement is sensed to indirectly sense eye muscle stimulation.

In some embodiments, the present invention provides an apparatus that includes one or more laser light sources configured to generate a plurality of light signals; and a transmission medium configured to transmit the plurality of light signals from the one or more laser light sources to one or more nerves of each of one or more inner-ear vestibular organs of a living animal; a controller to selectively control the plurality of light signals from each of the one or more infrared-laser light sources such that the light signals provide controlled optical stimulation to the one or more nerves in order to control nerve action potentials (NAPS) produced by the one or more nerves.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the control of the light signals provided by the controller includes selective control of a pulse width of the plurality of light signals.

In some embodiments, the control of the light signals provided by the controller includes selective control of a duty cycle of the plurality of light signals.

In some embodiments, the control of the light signals provided by the controller includes selective control of an on-time and an off-time of the plurality of light signals.

In some embodiments, the control of the light signals provided by the controller includes selective control of a wavelength of the plurality of light signals.

In some embodiments, the control of the light signals provided by the controller includes selective control of a pulse repetition rate of the plurality of light signals.

In some embodiments, the control of the light signals provided by the controller includes selective control of a pulse shape of the plurality of light signals.

In some embodiments, the control of the light signals provided by the controller includes selective control of a minimum light intensity and a maximum light intensity of the plurality of light signals.

In some embodiments, the control of the light signals provided by the controller includes selective control of a DC background amount of light intensity of the plurality of light signals.

In some embodiments, the control of the light signals provided by the controller includes selective control of a pre-charge amount of light intensity followed by a trigger amount of light intensity amount of light intensity of the plurality of light signals.

In some embodiments, the control of the light signals provided by the controller includes selective control of the plurality of light signals to delay at least some of the NAPs produced by the one or more nerves that would otherwise occur.

In some embodiments, the control of the light signals provided by the controller includes selective control of the plurality of light signals to increase a frequency of the NAPs produced by the one or more nerves that would otherwise occur.

In some embodiments, the control of the light signals provided by the controller includes selective control of the plurality of light signals to decrease a frequency of the NAPs produced by the one or more nerves that would otherwise occur.

In some embodiments, the apparatus includes an implanted a self-contained battery-powered laser light-generation device.

In some embodiments, the obtaining the plurality of light signals includes implanting self-contained infrared (IR) laser device.

In some embodiments, the a transmission medium configured to transmit light signals from the one or more laser light sources to one or more nerves of each of one or more inner-ear vestibular organs of a living animal includes one or more optical fibers configured to guide the light signals.

In some embodiments, the one or more laser light sources include a first light source and a second light source, wherein the control of the light signals provided by the controller includes selective control of the first light source to send a first series of pulses during a first period of time and selective control of the second light source to send a second series of pulses during the first period of time, and wherein the first series of pulses differs from the second series of pulses in repetition rate.

In some embodiments, the present invention provides an apparatus further including at least one sensor configured to sense one or more conditions that affect balance, and wherein the control of the light signals provided by the controller includes selective control of the light signals to provide a sense-of-balance nerve stimulation at least partly based on a signal from the at least one sensor.

In some embodiments, the at least one sensor includes a motion sensor.

In some embodiments, the at least one sensor includes an orientation sensor.

In some embodiments, the at least one sensor includes a muscular stimulation monitor.

In some embodiments, electrical stimulation carried via efferent nerves to muscles is sensed. In some embodiments, the result of the muscular movement is sensed.

In some embodiments, the muscular stimulation monitor includes a sensor that monitors eye movements.

In some embodiments, the present invention provides an apparatus that includes means for obtaining a plurality of light signals from one or more laser light sources; means for delivering the plurality of light signals to one or more nerve pathways of each of one or more inner-ear vestibular organs of a living animal; and means for selectively controlling the plurality of light signals to optically stimulate the one or more nerves in order to control nerve action potentials (NAPS) or compound nerve action potentials (CNAPs) produced in the one or more nerve pathways.

In some embodiments, the living animal is a human person. In some embodiments, the living animal is a large non-human animal, e.g., a race horse or dairy cow. In some embodiments, the living animal is a small non-human animal, e.g., a dog or cat.

In some embodiments, the means for selectively controlling the light signals includes means for controlling a pulse width of the plurality of light signals.

In some embodiments, the means for selectively controlling the light signals includes means for controlling a duty cycle of the plurality of light signals.

In some embodiments, the means for selectively controlling the light signals includes means for controlling an on-time and an off-time of the plurality of light signals.

In some embodiments, the means for selectively controlling the light signals includes means for controlling a wavelength of the plurality of light signals.

In some embodiments, the means for selectively controlling the light signals includes means for controlling a pulse repetition rate of the plurality of light signals.

In some embodiments, the means for selectively controlling the light signals includes means for controlling a pulse shape of the plurality of light signals.

In some embodiments, the means for selectively controlling the light signals includes means for controlling a minimum light intensity and a maximum light intensity of the plurality of light signals.

In some embodiments, the means for selectively controlling the light signals includes means for controlling a DC background amount of light intensity of the plurality of light signals.

In some embodiments, the means for selectively controlling the light signals includes means for controlling a pre-charge amount of light intensity followed by a trigger amount of light intensity of the plurality of light signals.

In some embodiments, the means for selectively controlling the light signals includes means for controlling the light signals to delay at least some of the NAPs produced by the one or more nerves that would otherwise occur without the plurality of light signals.

In some embodiments, the means for selectively controlling the light signals includes means for controlling the light signals to increase a frequency of the NAPs produced by the one or more nerves that would otherwise occur without the plurality of light signals.

In some embodiments, the means for selectively controlling the light signals includes means for controlling the light signals to decrease a frequency of the NAPs produced by the one or more nerves that would otherwise occur without the plurality of light signals.

In some embodiments, the means for obtaining the plurality of light signals includes implanting a self-contained battery-powered laser-light-generation device.

In some embodiments, the obtaining the plurality of light signals includes implanting self-contained infrared (IR) laser device.

In some embodiments, the means for delivering the plurality of light signals to one or more nerves of each of one or more inner-ear vestibular organs includes using one or more optical fibers to guide the light signals.

In some embodiments, the one or more laser light sources include a first light source and a second light source, wherein the means for selectively controlling the plurality of light signals includes means for controlling the first light source to send a first series of pulses during a first period of time and means for controlling the second light source to send a second series of pulses during the first period of time, and wherein the first series of pulses differs from the second series of pulses in repetition rate.

In some embodiments, the present invention provides an apparatus further including means for sensing one or more conditions that affect balance, and wherein the means for selectively controlling the plurality of light signals includes means for controlling the light signals, at least partly based on the sensed one or more conditions that affect balance, to provide a sense-of-balance nerve stimulation.

In some embodiments, the means for sensing of the one or more conditions that affect balance includes means for sensing motion and orientation.

In some embodiments, the means for sensing the one or more conditions that affect balance includes means for monitoring muscular stimulation.

In some embodiments, electrical stimulation delivered via nerves connected to muscles is sensed. In some embodiments, the result of the muscular movement is sensed.

In some embodiments, the means for monitoring muscular stimulation includes means for monitoring eye movements.

In some embodiments, electrical stimulation delivered via nerves connected to eye muscles is sensed. In some embodiments, the eye movement is sensed to indirectly sense eye muscle stimulation.

In some embodiments, electrical stimulation to eye muscles is sensed. In some embodiments, the eye movement is sensed to indirectly sense eye muscle stimulation.

In some embodiments, the present invention provides a method that includes obtaining light from an optical source; and transmitting the light to respective nerves of each of a plurality of inner-ear balance organs of an animal. The animal can either be a human or be some other animal.

In some embodiments, the transmitting includes transmitting different amounts of the light through optical fibers to stimulate respective nerves of each of the plurality of inner-ear balance organs.

In some embodiments, the transmitting includes transmitting different wavelengths of the light to stimulate respective nerves of each of the plurality of inner-ear balance organs.

In some embodiments, various parameters are adjusted and/or controlled, such as the pulse repetition rate or pattern, the pulse width, the pulse intensity, the wavelength(s), the amount of background constant (DC) optical level, and/or selected multiple simultaneous wavelengths. Multiple wavelengths are provided, in some embodiments, by using a plurality of lasers having different wavelengths. In some embodiments, a plurality of fibers is used to deliver the stimulation light to a plurality of stimulation sites.

In some embodiments, the present invention includes triggers and sensors that generate signals that are input to software of the present invention, wherein the software analyzes the signals and based on the analysis, generates control signals that control the parameters, such as frequency and intensity of light output (e.g., laser pulses) for each of one or more channels that communicate with the vestibular nucleus. For example, some embodiments use sensors such as described in U.S. Pat. No. 6,546,291 issued to Merfeld et al. on Apr. 8, 2003, which was described above and which is incorporated herein by reference. For example, some embodiments include sensors for detecting characteristics of the patient's head, eyes, posture and the like.

Some embodiments use one or more implanted VCSEL arrays to directly stimulate the desired nerves, while in other embodiments, one or more implanted VCSELs are optically coupled using one or more optical fibers leading to the stimulation sites.

In other embodiments, one or more VCSEL arrays are located external to the patient's body and use transcutaneous coupling to one or more implanted fiber arrays. In some embodiments, the implanted fiber arrays provide one or more feedback loops (e.g., a fiber having both of its ends facing outwards from the body) in order to assist coupling alignment. In some embodiments, permanent magnets are used on the implanted fiber arrays and external VCSEL stimulator to maintain coupling and assist in coupling alignment. In some embodiments, the implanted fiber arrays have a bulbous head on each fiber to collect and direct laser light into the fiber core.

Some embodiments provide programmable and/or reprogrammable control. In some embodiments, the controller is implanted in the body, and in some other embodiments, the controller is located external to the body and coupled to an implanted fiber array using transcutaneous coupling (e.g., some embodiments use a VCSEL array to provide light from the stimulator.

In some embodiments, electrical signals of the nerves are sensed and used to provide feedback to the controller, in order to better control the laser stimulation signal.

In some embodiments, the optical nerve stimulation is used to supplement or override the nerve responses generated by the inner ear organs. Some conditions, e.g., Benign Paroxysmal Positional Vertigo (BPPV), result from over-stimulation of nerves in a normally resting position. Through additional optical nerve stimulation, the natural nerve responses can be supplemented or overridden. In some embodiments, wider pulse width optical nerve stimulations are used to override or reduce the frequency of natural nerve responses to treat some inner ear conditions.

In some embodiments, the obtaining light includes implanting a self-contained infrared laser device.

In some embodiments, the obtaining light includes implanting a self-contained battery-powered device.

In some embodiments, the animal is a human person. In some embodiments, the animal is not human. Some embodiments further include sensing a condition that affects balance, and wherein the transmitting includes transmitting different light signals to each of a plurality of different balance-sense organs to provide the person sense-of-balance nerve stimulation.

In other embodiments, the present invention provides an apparatus that includes an optical source; and a transmission medium configured to transmit light from the optical source to respective nerves of each of a plurality of inner-ear balance organs of an animal.

In some embodiments, the transmission medium includes a plurality of optical fibers, and the optical source couples different amounts of the light through the plurality of optical fibers to stimulate different respective nerves of each of the plurality of inner-ear balance organs.

In some embodiments, the optical source couples different wavelengths of the light to stimulate different respective nerves of each of the plurality of inner-ear balance organs.

In some embodiments, the optical source includes a self-contained implantable infrared laser device.

In some embodiments, the optical source includes a self-contained battery-powered device.

In some embodiments, the animal is a human person. Some embodiments further include at least one sensor configured to sense a condition that affects balance, and wherein the transmission medium transmits different light signals, based on the sensed condition, to each of a plurality of different balance-sense organs to provide the person sense-of-balance nerve stimulation.

In other embodiments, the present invention provides an apparatus that includes means for obtaining light from an optical source; and means for transmitting the light to respective nerves of each of a plurality of inner-ear balance organs of an animal.

In some embodiments of the apparatus, the means for transmitting includes means for transmitting different amounts of the light through optical fibers to stimulate respective nerves of each of the plurality of inner-ear balance organs. In some embodiments, the means for transmitting includes means for transmitting different wavelengths of the light to stimulate respective nerves of each of the plurality of inner-ear balance organs. In some embodiments, the means for obtaining light includes a self-contained infrared laser implantable device. In some embodiments, the means for obtaining light includes a self-contained battery-powered implantable device.

In some embodiments, the animal is a human person, and the apparatus further includes means for sensing a condition that affects balance, and wherein the means for transmitting includes means for transmitting different light signals, based on the sensed condition, to each of a plurality of different balance-sense organs to provide the person sense-of-balance nerve stimulation.

For each of the above embodiments that describe a stimulation of a vestibular organ, there are other embodiments of the present invention that stimulate any and/or all elements of the vestibular system: inner-ear vestibular organs, cranial nerve VIII, vestibular nucleus, or any other central process of an animal's system.

Current conventional methods to excite neurons of the auditory brainstem or auditory midbrain include surface and penetrating electrodes that electrically stimulate surrounding neural tissue. The target of these electrodes is the cochlear nucleus or the inferior colliculus.

Some Relevant Publications are the Following:

Shannon R V, Otto S R.; Psychophysical measures from electrical stimulation of the human cochlear nucleus, Hear. Res., 1990 Aug. 1; 47(1-2):159-68. Otto S R, House W E, Brickman D E, Heidelberger W E, Nelson R A.; *Auditory brain stem implant: effect of tumor size and preoperative hearing level on function*, Ann. Otol. Rhinol Laryngeal., 1990 October; 99(10 Pt 1):789-90.

Liu X, McPhee G, Seldon H L, Clark G M.; Histological and physiological effects of the central auditory prosthesis: surface versus penetrating electrodes, Hear, Res. 1997 December; 114(1-2):264-74.

Lenarz T, Lim H H, Reuter G, Patrick J F, Lenarz M.; The auditory midbrain implant: a new auditory prosthesis for neural deafness-concept and device description, Otol. Neurotol. 2006 September; 27(6):838-43. Review.

Samii A, Lenarz M, Majdani O, Lim H H, Samii M, Lenarz T.; Auditory midbrain implant: a combined approach for vestibular schwannoma surgery and device implantation. Otol. Neurotol. 2007 January; 28(1):31-8.

The cochlear nucleus is an important first relay station for all auditory information that originates in the ear and travels along the auditory nerve. This target is very small, however, and after conventional electrical auditory-brainstem-implant electrodes are placed, many patients experience non-auditory sensations because non-auditory neurons nearby are being stimulated. The fundamental advantage of optical stimulation is that only neurons that are located in the path of the radiant energy are excited, and so one can achieve far greater selectivity when targeting neural tissues optically rather than electrically. As a result, one could use many more point sources of stimulation (optical-signal fibers) and have enhanced channel selectivity using optical stimulation. This has inherent advantages in the auditory brainstem and midbrain because there are so many different (non-auditory) neurons in very close proximity to the auditory neurons. In some embodiments of the present invention, an optical auditory brainstem or midbrain implant, or a hybrid stimulator that uses both optical and electrical stimulation (either applied on the surface or when penetrated into the brainstem or midbrain), uses more stimulation channels (optical-signal fibers or electrical-signal electrodes) to provide improved auditory performance compared with a conventional electrical stimulator.

In some embodiments, the present invention provides a method for stimulating triggering of NAPs in neurons in the cochlea, in the cochlear nerve, and/or nerves of the brainstem or midbrain of a patient to provide sensations (e.g., auditory and/or balance sensations) for the patient. This method includes generating a plurality of light signals that, when applied to a neuron of a person, can stimulate a nerve action potential in the neuron; delivering the light signals to one or a plurality of neurons of the brainstem or midbrain of the patient; and selectively controlling the plurality of light signals to optically stimulate the one or more neurons in order to control nerve action potentials (NAPs) produced by the plurality of neurons. Some embodiments further include receiving (or measuring or sensing or obtaining) an audio signal; and processing the received audio signal to obtain frequency and intensity information, wherein the delivering of light signals comprises delivering the light pulses to an auditory portion of the brainstem or midbrain of the patient, and wherein the selectively controlling of the light signals includes selectively controlling the light signals to emit light pulses to selected locations of the brainstem or midbrain of the patient based on the frequency information and at selected pulse-repetition rates based on the intensity information. In some such embodiments, the method further includes delivering an electrical signal to the plurality of neurons of the auditory portion of the brainstem or midbrain of the patient, such that a combination of the electrical signal and the light signals stimulate the nerve action potentials in the plurality of neurons. In some embodiments, the present invention uses electrical sources where appropriate for widespread stimulation (either using a higher-signal-strength electrical stimulation alone to trigger widespread NAPs in surrounding tissue, and/or using a lower-signal-strength electrical stimulation signal to sensitize the nearby tissue in order to reduce the optical power needed to trigger NAPs) and utilizes optical signal sources for triggering the frequency-specific "spikes". This allows for power-supply savings by limiting (i.e., reducing) the use of the optical sources for triggering NAPs in response to sensed broadband audio signals (audio signals having many different frequency components), and better replication (improved fidelity of the hearing sensation of the patient) of the audio signal content by using the characteristics of both electrical and optical stimulation when only one or just a few frequency components are sensed. In some embodiments, the electrical and optical stimulation sources are connected to and driven by the output of a signal processor whose input is coupled to signals from a acoustic-detector device (e.g., in some embodiments, a device such as are typically used for electrical-stimulation cochlear implants). In some embodiments, the signal-processor device processes the acoustic information and separates the signals into two or more groups, including at least one with broadband characteristics and at least one with narrow band characteristics. The device then selectively activates the electrical and optical sources based at least in part on the broadband and narrow-band groups.

In some embodiments, the present invention provides a method for stimulating neurons of a brainstem or midbrain of a patient to provide sensations for the patient. This method includes generating a plurality of light signals that have different wavelengths and that, when applied to a neuron of a person, can stimulate a nerve action potential in the neuron; generating sensitizing signals that, when applied to a neuron of a person, can sensitize the neuron to trigger a nerve action potential in the neuron upon an additional application of light to the neuron; delivering the sensitizing signals to a plurality of neurons of the brainstem or midbrain of the patient; delivering the generated light signals to a plurality of neurons of the cochlea, the cochlear nerve, the auditory brainstem, or the midbrain of the patient; and selectively controlling the plurality of light signals to optically stimulate the plurality of neurons in order to control nerve action potentials (NAPs) produced by the plurality of neurons. In some embodiments, the sensitizing signals include sub-threshold electrical signals (signals that alone have a low probability (e.g., in some embodiments, less than 25% probability of triggering a NAP from one such sub-threshold electrical signal, or in other embodiments, less than 33%, 20%, 10%, 5% or 2% probability of triggering a NAP from one such sub-threshold electrical signal) that reduce the amount of optical energy needed to reliably trigger a NAP.

In some embodiments, the present invention provides a method for stimulating neurons of a plurality of auditory nerve pathways, of a person to provide sensations for the person, the plurality of auditory nerve pathways including a first auditory nerve pathway and a second auditory nerve pathway. This method includes generating a plurality of light signals, including a first light signal and a second light signal, that, when applied to a neuron of the person while the neuron is sensitized, each will stimulate a nerve action potential (NAP) in the neuron; generating a plurality of sensitizing signals, including a first sensitizing signal and a second sensitizing signal, that, when applied to the neuron of the person, will sensitize the neuron to trigger a NAP in the neuron upon application of one or more of the plurality light signals to the neuron; delivering the first sensitizing signal to a plurality of neurons of the auditory nerve pathway of the person; delivering the first light signal to one or more neurons of a first auditory nerve pathway of the person; delivering the second light signal to one or more neurons of a second auditory nerve pathway of the person; and selectively controlling the plurality of light signals to optically stimulate the one or more neurons in order to control NAPs triggered in the one or more neurons in the first auditory nerve pathway independently from NAPs in the one or more neurons in the second auditory nerve pathway.

Some embodiments of the method further include further comprising sensing one or more conditions that affect balance, and wherein the selectively controlling the plurality of light signals includes controlling the light signals, at least partly based on the sensed one or more conditions that affect balance, to provide a sense-of-balance nerve stimulation to the brainstem or midbrain of the patient.

Some embodiments of the method further include receiving image data; and processing the received image data to obtain vision information, wherein the delivering of light signals comprises delivering the light pulses to a vision portion of the brainstem or midbrain of the patient.

Some embodiments of the method further include receiving an audio signal; and processing the received audio signal to obtain frequency and intensity information, and electronically pre-processing the frequency and intensity information derived from the received audio signal (the signal from the microphone) to obtain information corresponding to the physiologically early-processed audio information that would have been present in a normally hearing person, and applying optical and/or electrical stimulation that represents this pre-processed information to those portions of the auditory nerve pathways (e.g., in the brainstem or midbrain) that are closer to the auditory cortex, and wherein the delivering of the plurality of light signals includes delivering the light pulses to an auditory portion of the brainstem or midbrain of the person, and wherein the selectively controlling of the light signals includes selectively controlling the light signals to emit light pulses to selected locations of the brainstem or midbrain of the person based on the pre-processed information.

Some embodiments of the method further include receiving an audio signal; and processing the received audio signal to obtain audio frequency and intensity information, wherein the delivering of the plurality of light signals comprises delivering the light pulses to the cochlea of the person, and wherein the selectively controlling of the light signals includes selectively controlling the light signals to emit light pulses to selected locations of the cochlea of the person based on the frequency information and at selected pulse-repetition rates based on the intensity information.

In some embodiments, the sensitizing signals include electrical signals that are applied to the tissue to which the optical signal is directed. In some such embodiments, the method further includes applying the electrical signal between one electrode located in the scala vestibuli 77 and/or cochlear channel (see FIG. 26) of the cochlea 78 and another electrode located in the scala tympani 79 of the cochlea 78. In some embodiments, a first electrode (one of a plurality of electrodes in the scala vestibuli) is selectively activated simultaneously with a second electrode (one of a plurality of electrodes in the scala tympani) being selectively activated, such that only a subportion of the organ of Corti that is located between the first electrode in the scala vestibuli and the second electrode in the scale tympani is sensitized. In some embodiments, a first optical emitter (such as a VCSEL) located next to the second electrode is selectively activated to emit a light signal to trigger one or more NAPs in one or more neurons in a first auditory nerve pathway that is sensitized by the electrical signal between the first electrode and the second electrode (e.g., in some embodiments, the light signal triggers a NAP in one or more hair cells or one or more nerve cells of the spiral ganglion). In some embodiments, the second electrode surrounds the first optical emitter (e.g., as a ring electrode). In some embodiments, the second electrode acts as an electrical-signal connection to the first optical emitter.

Some embodiments of the method include receiving an audio signal, processing the audio signal to obtain frequency and intensity information, and using the frequency and intensity information to control the electrical sensitization and optical stimulation signals.

In some embodiments, the density of optical emitters is non-uniform (e.g., the density of optical emitters is higher in some areas of the cochlea than in other areas of the cochlea). In some such embodiments, a logarithmic density distribution is used. In some embodiments, many more optical emitters are provided than are used, in order that the placement of the optical emitters is less critical, and such that testing (emitting optical signals from selected ones of the optical emitters and determining whether an auditory sensation was triggered and, if so, which audio frequency corresponds to the auditory sensation that was triggered) determines a mapping between those optical emitters that trigger an auditory sensation and which audio sensation (e.g., which audio frequency perception) is stimulated. Thereafter, the implanted device is programmed to trigger appropriate NAPS in the selected ones of the plurality of auditory nerve pathways based on the processed frequency and intensity information derived from the received audio signal.

In some embodiments, the method further includes receiving an audio signal; and processing the received audio signal to obtain frequency and intensity information, wherein the delivering of the plurality of light signals comprises delivering the light pulses to an auditory portion of the brainstem or midbrain of the person, and wherein the selectively controlling of the light signals includes selectively controlling the light signals to emit light pulses to selected locations of the brainstem or midbrain of the person based on the frequency information and at selected pulse-repetition rates based on the intensity information.

In some embodiments, the method further includes receiving an audio signal; and processing the received audio signal to obtain frequency and intensity information, wherein the delivering of the plurality of light signals comprises delivering the light pulses to an auditory portion of the cochlea of the person, and wherein the selectively controlling of the light signals includes selectively controlling the light signals to emit light pulses to selected locations of the cochlea of the person based on the frequency information and at selected pulse-repetition rates based on the intensity information.

In some embodiments, the delivering of the first light signal occurs inside a cochlea of the person and the delivering the second light signal to one or more neurons occurs inside the cochlea of the person.

In some embodiments, the delivering of light signals further includes delivering infrared light from a laser.

In some embodiments, the delivering of light signals further includes delivering infrared light from a vertical-cavity surface-emitting laser (VCSEL).

In some embodiments, the generating of the plurality of sensitizing signals includes generating electrical sensitizing signals and the delivering of the first sensitizing signal to a plurality of neurons of the auditory nerve pathway of the person.

In some embodiments, the delivering of light signals further includes delivering the light signals to central portions of the neurons.

In some embodiments, the delivering of the light signals further includes obtaining a plurality of light signals from one or more laser light sources and delivering the obtained light signals to discrete portions of excitable tissues, said signals being interpretable by the person's brain as sensory responses.

In some embodiments, the delivering of the light signals further includes selectively controlling the light signals to optically stimulate the plurality of neurons in order to control nerve action potentials (NAPs) produced by the plurality of neurons.

In some embodiments of the method, the delivering of light signals further includes delivering the light signals to peripheral projections of the neurons.

In some embodiments of the method, the delivering of light signals further includes delivering the light signals to central portions of the neurons.

In some embodiments of the method, the delivering of the light signals further includes obtaining a plurality of light signals from one or more laser light sources and delivering the obtained light signals to discrete portions of excitable tissues, said signals being interpretable by the patient's brain as sensory responses.

In some embodiments of the method, the delivering of the light signals further includes selectively controlling the light signals to optically stimulate the one or more neurons in order to control nerve action potentials (NAPs) produced by the one or more neurons. In some embodiments of the method, the selectively controlling the light signals further includes controlling a pulse width of the plurality of light signals. In some embodiments of the method, the selectively controlling the light signals further includes controlling a pulse repetition rate of the plurality of light signals. In some embodiments of the method, the selectively controlling the light signals further includes controlling a pulse shape of the plurality of light signals. In some embodiments of the method, the selectively controlling the light signals further includes controlling a DC background amount of light intensity of the plurality of light signals. In some embodiments of the method, the selectively controlling the light signals further includes controlling a precharge amount of light intensity followed by a trigger amount of light intensity of the plurality of light signals. In some embodiments of the method, the selectively controlling the light signals further includes controlling the light signals to increase a frequency of the NAPs produced by the one or more neurons that would otherwise occur without the plurality of light signals.

In some embodiments of the method, the obtaining of the plurality of light signals further includes implanting a self-contained battery-powered laser-light-generation device.

In some embodiments of the method, the delivering of the light signals to the plurality of neurons of the brainstem or midbrain of the patient includes positioning a delivery end of a plurality of optical fibers in a probe end placed against the brainstem or midbrain of the patient and using the plurality of optical fibers to guide the light signals from a laser source to the brainstem or midbrain of the patient.

In some embodiments of the method, the generating of the light signals includes providing a first laser source and a second laser source, wherein the selectively controlling the plurality of light signals includes controlling the first laser source to send a first series of pulses during a first period of time and controlling the second laser source to send a second series of pulses during the first period of time, and wherein the first series of pulses differs from the second series of pulses in repetition rate. In some embodiments of the method, the sensing of the one or more conditions that affect balance includes monitoring eye movements.

In some embodiments, the present invention provides an apparatus that includes a plurality of independently controllable light sources that are configured to generate a plurality of light signals, including a first light signal and a second light signal, that, when applied to a neuron of the person while the neuron is sensitized, each will stimulate a nerve action potential (NAP) in the neuron; a sensitizing-signal generator that generates a plurality of sensitizing signals, including a first sensitizing signal and a second sensitizing signal, that, when applied to the neuron of the person, will sensitize the neuron to trigger a NAP in the neuron upon application of one or more of the plurality light signals to the neuron; a transmission medium configured to transmit the first light signal from the plurality of light sources to one or more neurons of a first auditory nerve pathway of the person, and to transmit the second light signal from the plurality of light sources to one or more neurons of a second auditory nerve pathway of the person; and a controller operatively coupled to the plurality of light sources to selectively control the plurality of light signals, and operatively coupled to the sensitizing-signal generator to selectively control the plurality of sensitizing signals, such that in combination with the plurality of sensitizing signals the first light signal provides controlled optical stimulation to control nerve action potentials (NAPs) produced by the one or more neurons in the first auditory nerve pathway but not the second auditory pathway, and the second light signal provides controlled optical stimulation to control NAPs produced by the one or more neurons in the second auditory nerve pathway but not the first auditory pathway, in order to provide auditory sensations for the person.

Some embodiments of the apparatus further include an audio-signal processor; and an audio-signal processor that processes the received audio signal to obtain frequency and intensity information, wherein the delivering of the plurality of light signals comprises delivering the light pulses to an auditory portion of the brainstem or midbrain of the person, and wherein the selectively controlling of the light signals includes selectively controlling the light signals to emit light pulses to selected locations of the brainstem or midbrain of the person based on the frequency information and at selected pulse-repetition rates based on the intensity information.

In some embodiments of the apparatus, the control of the light signals provided by the controller includes selective control of a wavelength of the plurality of light signals.

In some embodiments of the apparatus, the transmission medium includes a plurality of parallel optical-signal-transmission channels.

In some embodiments of the apparatus, the transmission medium includes a plurality of optical fibers each of which carries a different signal.

In some embodiments of the apparatus, the transmission medium includes an optical fiber.

Some embodiments of the apparatus further include a microphone having a signal output operatively coupled to a wireless transmitter that is configured to transmit information based on the microphone signal to the controller.

In some embodiments of the apparatus, the microphone further includes a processor that is configured to receive a sound signal and based on the sound signal to generate information used by the controller to generate stimulation pulses configured to be interpretable by the living animal's brain as having one or more frequency components and an intensity, in order to encode hearing.

In some embodiments of the apparatus, the one or more light sources includes a plurality of vertical-cavity surface-emitting lasers (VCSELs).

In some embodiments, the present invention provides an apparatus for stimulating neurons of a plurality of auditory nerve pathways, of a person to provide sensations for the person, the plurality of auditory nerve pathways including a first auditory nerve pathway and a second auditory nerve pathway. This apparatus includes means for generating a plurality of light signals, including a first light signal and a second light signal, that, when applied to a neuron of the person while the neuron is sensitized, each will stimulate a nerve action potential (NAP) in the neuron; means for generating a plurality of sensitizing signals, including a first sensitizing signal and a second sensitizing signal, that, when applied to the neuron of the person, will sensitize the neuron to trigger a NAP in the neuron upon application of one or more of the plurality light signals to the neuron; means for delivering the first sensitizing signal to a plurality of neurons of the auditory nerve pathway of the person; means for delivering the first light signal to one or more neurons of a first auditory nerve pathway of the person; means for delivering the second light signal to one or more neurons of a second auditory nerve pathway of the person; and means for selectively controlling the plurality of light signals to optically stimulate the one or more neurons in order to control NAPs triggered in the one or more neurons in the first auditory nerve pathway independently from NAPs in the one or more neurons in the second auditory nerve pathway. Some embodiments of the apparatus further include means for receiving an audio signal; and means for processing the received audio signal to obtain frequency and intensity information, wherein the delivering of the plurality of light signals comprises delivering the light pulses to an auditory portion of the cochlea of the person, and wherein the selectively controlling of the light signals includes selectively controlling the light signals to emit light pulses to selected locations of the cochlea of the person based on the frequency information and at selected pulse-repetition rates based on the intensity information. Some embodiments of the apparatus further include means for determining whether a first temporal period of the received audio signal includes a wideband audio-spectral content; and means for, based on the determination of the wideband audio-spectral content, delivering an electrical signal corresponding to the first temporal period to both the first audio pathway and the second audio pathway of the person simultaneously, with sufficient current to trigger NAPs in both the first audio pathway and the second audio pathway of the person without use of the light signals.

In some embodiments, the present invention provides an apparatus that includes one or more light sources that are configured to generate a plurality of light signals; a transmission medium configured to transmit the plurality of light signals from the one or more light sources to triggering NAPs in neurons in the cochlea, in the cochlear nerve, and/or nerves of the brainstem or midbrain of a patient to provide sensations (e.g., auditory and/or balance sensations in a living animal to provide auditory sensations for the living animal; and a controller operatively coupled to the one or more light sources to selectively control the plurality of light signals from each of the one or more light sources such that the light signals provide controlled optical stimulation to the plurality of neurons in order to control nerve action potentials (NAPs) produced by the plurality of neurons.

In some embodiments of the apparatus, control of the light signals provided by the controller includes selective control of a duty cycle of the plurality of light signals.

In some embodiments of the apparatus, the control of the light signals provided by the controller includes selective control of a wavelength of the plurality of light signals.

In some embodiments of the apparatus, the transmission medium includes a plurality of data channels (i.e., input and/or output channels (called "I/Os")). In some embodiments, the transmission medium includes a plurality of optical fibers, each having a conductive material (e.g., a metal film) applied to a surface of the optical fiber, wherein the conductive material is in turn covered with an insulator (e.g., a polymer coating, and/or a silicon oxide and/or silicon nitride insulator layer), and optionally one or more additional conductive layers further coated by additional insulator layers to provide a coaxially shielded electrical conductor that is formed directly on the optical fiber, and wherein the optical fiber is used to deliver the optical stimulation pulses and the one or more electrical conductors are used to transmit electrical stimulation or pre-conditioning electrical energy to the tissue being stimulated. In some embodiments, the electrical conductors are also used to carry electrical signals sensed from the neurons of the patient (e.g., NAP signals in the nerve pathways are detected electrically using the conductors formed on the optical fibers). In some embodiments, each of a plurality of the optical fibers have a metallic coating that has an insulator formed over the metallic coating, and a bundle of such fibers deliver a plurality of different optical signals (e.g., the optical-stimulation pulses are individually controlled) in parallel and a plurality of different stimulation electrical signals (e.g., the electrical-stimulation or -preconditioning pulses are individually controlled) in parallel such that different areas of the brainstem or midbrain of the patient are stimulated in different manners (e.g., different frequencies of sensed audio are used to calculate the various streams of pulse data (the streams being the time-sequenced pulses for each channel of data that are each sent to different respective nerve pathways (wherein the different nerve pathways each initially represent nerve signals for different frequencies, but it is believed that perhaps during transmission a certain amount of audio-signal processing is performed by the various nerve interconnections such that further towards the brain, the nerve action potentials represent audio data that has been at least partially preprocessed before reaching the destinations in the audio cortex of the patient's brain), and different intensities of sensed audio at the various frequencies are used to calculate the repetition rates for the pulse data that are sent to different nerve pathways.

In some embodiments of the apparatus, the transmission medium includes a plurality of optical fibers each of which carries a different signal. In some such embodiments, the plurality of optical fibers each have one or more electrical conductors formed thereon, wherein each of a plurality of the electrical conductors carry a different signal.

In some embodiments of the apparatus, the transmission medium includes an optical fiber. In some embodiments of the apparatus, the transmission medium includes a lens. In some embodiments of the apparatus, the transmission medium delivers the light signals from the one or more light sources without using an optical fiber or a lens.

Some embodiments of the apparatus further includes a microphone having a signal output operatively coupled to a wireless transmitter that is configured to transmit information based on the microphone signal to the controller.

In some embodiments of the apparatus, the microphone further includes a processor that is configured to receive a sound signal and based on the sound signal to generate information used by the controller to generate stimulation pulses configured to be interpretable by the living animal's brain as having one or more frequency components and an intensity, in order to encode hearing.

In some embodiments of the apparatus, the one or more light sources further include one or more lasers. In some embodiments of the apparatus, the one or more light sources further include at least one tunable laser. In some embodiments of the apparatus, the one or more lasers output an infrared signal having a wavelength between about one micron and about five microns. In some embodiments of the apparatus, the one or more lasers output an infrared signal having a wavelength between about one micron and about two microns. In some embodiments of the apparatus, the one or more lasers output an infrared signal having a wavelength between about 1.8 microns and about 1.9 microns.

In some embodiments of the apparatus, the one or more lasers output an infrared signal having a wavelength between about 0.7 microns and about 0.8 microns. In some embodiments of the apparatus, the one or more lasers output an infrared signal having a wavelength between about 0.8 microns and about 0.9 microns. In some embodiments of the apparatus, the one or more lasers output an infrared signal having a wavelength between about 0.9 microns and about 1.0 microns. In some embodiments of the apparatus, the one or more lasers output an infrared signal having a wavelength between about 1.0 microns and about 1.1 microns. In some embodiments of the apparatus, the one or more lasers output an infrared signal having a wavelength between about 1.1 microns and about 1.2 microns. In some embodiments of the apparatus, the one or more lasers output an infrared signal having a wavelength between about 1.2 microns and about 1.3 microns. In some embodiments of the apparatus, the one or more lasers output an infrared signal having a wavelength between about 1.3 microns and about 1.4 microns. In some embodiments of the apparatus, the one or more lasers output an infrared signal having a wavelength between about 1.4 microns and about 1.5 microns. In some embodiments of the apparatus, the one or more lasers output an infrared signal having a wavelength between about 1.5 microns and about 1.6 microns. In some embodiments of the apparatus, the one or more lasers output an infrared signal having a wavelength between about 1.6 microns and about 1.7 microns. In some embodiments of the apparatus, the one or more lasers output an infrared signal having a wavelength between about 1.7 microns and about 1.8 microns. In some embodiments of the apparatus, the one or more lasers output an infrared signal having a wavelength between about 1.9 microns and about 2.0 microns. In some embodiments of the apparatus, the one or more lasers output an infrared signal having a wavelength between about 2.0 microns and about 2.1 microns. In some embodiments of the apparatus, the one or more lasers output an infrared signal having a wavelength between about 2.1 microns and about 2.3 microns. In some embodiments of the apparatus, the one or more lasers output an infrared signal having a wavelength between about 2.3 microns and about 2.5 microns. In some embodiments of the apparatus, the one or more lasers output an infrared signal having a wavelength between about 2.5 microns and about 5 microns. In some embodiments of the apparatus, the one or more lasers output an infrared signal having a wavelength between about 5 microns and about 10 microns.

In some embodiments of the apparatus, the one or more lasers output an infrared signal having a wavelength of about 1540 nanometers (1.54 microns). In some embodiments of the apparatus, the one or more lasers output an infrared signal having a wavelength of about 1800 nanometers. In some embodiments of the apparatus, the one or more lasers output an infrared signal having a wavelength of about 1849 nanometers. In some embodiments of the apparatus, the one or more lasers output an infrared signal having a wavelength of 1849 nanometers. In some embodiments of the apparatus, the one or more lasers output an infrared signal having a wavelength of about 1470 nanometers. In some embodiments of the apparatus, the one or more lasers output an infrared signal having a wavelength of 1470 nanometers.

In some embodiments, the present invention further includes applying a precharge amount of stimulation electrical current to the neuronal tissue of the patient that is to be stimulated (e.g., to a plurality of nerve pathways the brainstem or midbrain of the patient), which is then followed by a trigger amount of pulsed light intensity of the plurality of light signals.

In some embodiments, the nerve stimulation includes an electrical current of about 0.1 mA to about 10 mA, plus an optical energy of about 0.01 J/cm$^2$ to about 1 J/cm$^2$. In some embodiments, the stimulation includes an electrical current of about 0.01 mA to about 0.02 mA between closely spaced electrodes (in some embodiments, the closely spaced electrodes include a metallization layer on each of two optical fibers that are both in one fiber-optic bundle; while in other embodiments, the closely spaced electrodes include separated portions of a metallization layer on a single optical fiber (e.g., wherein the metallization has been etched into a plurality of separate longitudinal conductors, and, in some embodiments, wherein the etching is helical around the optical fiber such that a twisted pair of conductors (or a plurality of such pairs) is formed, while in other embodiments, coaxial metallization layers are formed using an insulating layer to separate each pair of conduction layers). A current is sent through the separate conductors on the optical fiber and thus through the tissue that is adjacent to the light-emitting end of the optical-fiber waveguide such that the electrical field and the optical radiation are self aligned with one another. In some embodiments, the stimulation includes an electrical current of about 0.02 mA to about 0.05 mA between closely spaced electrodes. In some embodiments, the stimulation includes an electrical current of about 0.025 mA to about 0.035 mA between closely spaced electrodes. In some embodiments, the stimulation includes an electrical current of about 0.035 mA to about 0.05 mA between closely spaced electrodes. In some embodiments, the stimulation includes an electrical current of about 0.025 mA between closely spaced electrodes. In some embodiments, the stimulation includes an electrical current of about 0.035 mA between closely spaced electrodes. In some embodiments, the stimulation includes an electrical current of about 0.05 mA between closely spaced electrodes. In some embodiments, the stimulation includes an electrical current of about 0.1 mA between closely spaced electrodes. In some embodiments, the stimulation includes an electrical current of about 0.05 mA to about 0.1 mA between closely spaced electrodes. In some embodiments, the stimulation includes an electrical current of about 0.1 mA to about 0.2 mA between closely spaced electrodes. In some embodiments, the stimulation includes an electrical current of about 0.2 mA to about 0.5 mA between closely spaced electrodes. In some embodiments, the stimulation includes an electrical current of about 0.5 mA to about 1 mA between closely spaced electrodes. In some embodiments, the stimulation includes an electrical current of about 1 mA to about 2 mA between closely spaced electrodes. In some embodiments, the stimulation includes an electrical current of about 2 mA to about 5 mA between closely spaced electrodes. In some embodiments, the stimulation includes an electrical current of about 5 mA to about 10 mA between closely spaced electrodes.

In some embodiments, the pulse repetition rate of the optical signal is about 1 to 2 pulses per second. In some embodiments, the pulse repetition rate of the optical signal is about 2 to 5 pulses per second. In some embodiments, the pulse repetition rate of the optical signal is about 5 to 10 pulses per second. In some embodiments, the pulse repetition rate of the optical signal is about 10 to 20 pulses per second. In some embodiments, the pulse repetition rate of the optical signal is about 20 to 50 pulses per second. In some embodiments, the pulse repetition rate of the optical signal is about 50 to 100 pulses per second. In some embodiments, the pulse repetition rate of the optical signal is about 100 to 200 pulses per second. In some embodiments, the pulse repetition rate of the optical signal is about 200 to 500 pulses per second. In some embodiments, the pulse repetition rate of the optical signal is about 500 to 1000 pulses per second. In some embodiments, the pulse repetition rate of the optical signal is about 1000 to 2000 pulses per second. In some embodiments, the pulse repetition rate of the optical signal is more than about 2000 pulses per second.

In some embodiments of the apparatus, the one or more lasers output an infrared signal having a radiant exposure of no more than 4 J/cm$^2$ per nerve-action-potential (NAP) response generated. In some embodiments of the apparatus, the one or more lasers output an infrared signal having a radiant exposure of no more than 3 J/cm$^2$ per NAP response generated. In some embodiments of the apparatus, the one or more lasers output an infrared signal having a radiant exposure of no more than 2 J/cm$^2$ per NAP response generated.

In some embodiments of the apparatus, the one or more lasers output an infrared signal having a radiant exposure of between about 5 J/cm$^2$ and about 6 J/cm$^2$ per NAP response generated. In some embodiments of the apparatus, the one or more lasers output an infrared signal having a radiant exposure of between about 4 J/cm$^2$ and about 4 J/cm$^2$ per NAP response generated. In some embodiments of the apparatus, the one or more lasers output an infrared signal having a radiant exposure of between about 3 J/cm$^2$ and about 4 J/cm$^2$ per NAP response generated. In some embodiments of the apparatus, the one or more lasers output an infrared signal having a radiant exposure of between about 3 J/cm$^2$ and about 3.5 J/cm$^2$ per NAP response generated. In some embodiments of the apparatus, the one or more lasers output an infrared signal having a radiant exposure of between about 2.5 J/cm$^2$ and about 3 J/cm$^2$ per NAP response generated. In some embodiments of the apparatus, the one or more lasers output an infrared signal having a radiant exposure of between about 2 J/cm$^2$ and about 2.5 J/cm$^2$ per NAP response generated. In some embodiments of the apparatus, the one or more lasers output an infrared signal having a radiant exposure of between about 1.5 J/cm² and about 2 J/cm² per NAP response generated. In some embodiments of the apparatus, the one or more lasers output an infrared signal having a radiant exposure of between about 1 J/cm² and about 1.5 J/cm² per NAP response generated. In some embodiments of the apparatus, the one or more lasers output an infrared signal having a radiant exposure of between about 0.5 J/cm² and about 1 J/cm² per NAP response generated. In some embodiments of the apparatus, the one or more lasers output an infrared signal having a radiant exposure of between about 0.2 J/cm² and about 0.5 J/cm² per NAP response generated. In some embodiments of the apparatus, the one or more lasers output an infrared signal having a radiant exposure of between about 0.1 J/cm² and about 0.2 J/cm² per NAP response generated.

In some embodiments, the one or more lasers output an infrared signal having and energy of less than about 2 mJ per pulse.

In some embodiments, the one or more lasers output an infrared signal having a pulse width of between about ten microseconds (10 µs) and about five milliseconds (5 ms). In some embodiments, the one or more lasers output an infrared signal having a pulse width of between about 1 µs and about 10 µs. In some embodiments, the one or more lasers output an infrared signal having a pulse width of between about 10 µs and about 20 µs. In some embodiments, the one or more lasers output an infrared signal having a pulse width of between about 20 µs and about 50 µs. In some embodiments, the one or more lasers output an infrared signal having a pulse width of between about 20 µs and about 40 µs. In some embodiments, the one or more lasers output an infrared signal having a pulse width of between about 40 µs and about 80 µs. In some embodiments, the one or more lasers output an infrared signal having a pulse width of between about 80 µs and about 160 µs. In some embodiments, the one or more lasers output an infrared signal having a pulse width of between about 50 µs and about 100 µs. In some embodiments, the one or more lasers output an infrared signal having a pulse width of between about 100 µs and about 200 µs. In some embodiments, the one or more lasers output an infrared signal having a pulse width of between about 200 µs and about 500 µs. In some embodiments, the one or more lasers output an infrared signal having a pulse width of between about 200 µs and about 400 µs. In some embodiments, the one or more lasers output an infrared signal having a pulse width of between about 400 µs and about 800 µs. In some embodiments, the one or more lasers output an infrared signal having a pulse width of between about 800 µs and about 1600 µs. In some embodiments, the one or more lasers output an infrared signal having a pulse width of between about 500 µs and about 1000 µs. In some embodiments, the one or more lasers output an infrared signal having a pulse width of between about 1 millisecond (ms) and about 2 ms. In some embodiments, the one or more lasers output an infrared signal having a pulse width of between about 2 ms and about 5 ms. In some embodiments, the one or more lasers output an infrared signal having a pulse width of between about 2 ms and about 4 ms. In some embodiments, the one or more lasers output an infrared signal having a pulse width of between about 4 ms and about 8 ms. In some embodiments, the one or more lasers output an infrared signal having a pulse width of between about 8 ms and about 16 ms. In some embodiments, the one or more lasers output an infrared signal having a pulse width of between about 5 ms and about 10 ms.

In some embodiments, the present invention delivers a pulse of electrical current (as in existing devices called auditory brainstem implants) to the same site as light pulses. In some embodiments, the electrical pulses are below the threshold for neural excitation and the electric field spreads to a larger area than required for the region of interest (the area of specific nerve pathways to be stimulated). The light pulse from the apparatus of the present invention is delivered to match the exact volume of tissue that is to be stimulated: In some embodiments, the stimulation includes an electrical current of about 0.1 mA to about 10 mA, plus an optical energy of about 0.01 J/cm² to about 1 J/cm². Other parameters are determined by empirical experimentation, wherein the pulse repetition rate is generally about 10 to 1000 pulses per second.

In some such embodiments, the present invention provides a method that includes applying a combination of both an electrical stimulation signal and an optical stimulation signal to trigger a nerve action potential (NAP) in vivo in the brainstem or midbrain of an animal. In some embodiments of this method, the optical stimulation signal is of a nature such that if applied alone the optical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. In some embodiments of this method, the electrical stimulation signal is of a nature such that if applied alone the electrical signal has a low probability to trigger a NAP, the probability being no more than 25%. Some embodiments of this method further include also selectively applying a visible-indication light signal that indicates a location that the optical stimulation signal is to be applied.

Some embodiments of this method further include using a hybrid probe having an optical fiber inserted an electrically conductive cannula; applying the optical-stimulation signal through the optical fiber; and applying the electrical-stimulation signal through the cannula. Some embodiments further include delivering a fluid through the cannula to enhance the electrical interface for the electrical-stimulation signal and/or to enhance the optical interface for the optical-stimulation signal and/or to deliver one or more drugs to the stimulation site. Some embodiments further include withdrawing a fluid through the cannula to diagnose a condition. Some embodiments of this method further include using a second probe to obtain an electrical signal representative of the triggered NAP. Some embodiments of this method further include the hybrid probe further includes an electrode that is electrically separate from the cannula, and the method further includes using the electrode to obtain an electrical response signal representative of the triggered NAP. Some embodiments of this method further include using the cannula to obtain an electrical response signal representative of the triggered NAP.

In some embodiments of this method, a signal representative of the electrical stimulation signal is subtracted from a signal obtained using the cannula to obtain the electrical response signal representative of the triggered NAP.

Some embodiments of this method further include using a hybrid probe having an optical fiber that has a metallization layer applied to the optical fiber; applying the optical-stimulation signal through the optical fiber; and applying the electrical-stimulation signal through the metallization layer. Some embodiments of this method further include using a second probe to obtain an electrical response signal representative of the triggered NAP. In some embodiments of this method, the hybrid probe further includes an electrode that is electrically separate from the metallization layer, and the method further includes using the electrode to obtain an electrical response signal representative of the triggered NAP. Some embodiments of this method further include using the metallization layer to obtain an electrical response signal representative of the triggered NAP.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the brainstem or midbrain of an animal.

In some embodiments of this apparatus, the optical stimulation signal is of a nature such that if applied alone the optical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the electrical stimulation signal is of a nature such that if applied alone the electrical stimulation signal has a low probability to trigger a NAP, the probability being no more than 25%. In some embodiments of this apparatus, the optical stimulation signal is infrared, and the apparatus further includes a visible-indication-light-signal source configured to project visible light to indicate a location that the optical stimulation signal is to be applied. Some embodiments of this apparatus further include a hybrid probe having an optical fiber inserted an electrically conductive cannula, wherein the optical-stimulation signal is applied through the optical fiber and the electrical-stimulation signal is applied through the cannula. Some embodiments further include a second probe configured to obtain an electrical signal representative of the triggered NAP. In some embodiments, the hybrid probe further includes an electrode that is electrically separate from the cannula, wherein the electrode is configured to obtain an electrical signal representative of the triggered NAP. In some embodiments, the cannula is used to obtain an electrical signal representative of the triggered NAP. In some such embodiments, the apparatus is configured to subtract a signal representative of the electrical stimulation signal from a signal obtained using the cannula to obtain the electrical signal representative of the triggered NAP.

Some embodiments further include a hybrid probe having an optical fiber that has a metallization layer applied to the optical fiber, wherein the optical-stimulation signal is applied through the optical fiber and the electrical-stimulation signal is applied through the metallization layer. Some embodiments further include a second probe configured to obtain an electrical signal representative of the triggered NAP. In some embodiments, the hybrid probe further includes an electrode that is electrically separate from the metallization layer, and is configured to obtain an electrical signal representative of the triggered NAP. In some embodiments, the apparatus is configured to use the metallization layer to obtain an electrical signal representative of the triggered NAP.

In some embodiments, a plurality of optrodes are each located next to, or surrounded by, a respective sensitization and/or stimulation-signal electrode (thus forming an array of optrodes and first electrodes). In some such embodiments, one or more second electrodes is/are located on an opposite side of the neuronal tissue to be stimulated, such that the amount of electrical current needed for sensitization is significantly reduced (e.g., minimized), and the optical stimulation signal is emitted substantially in the middle of the electrical field and current. In some embodiments, the optical stimulation signals are each generated by a VCSEL located within a respective ring electrode. In some embodiments, a carrier or substrate has a plurality of such VCSEL-and-ring-electrode structures and is inserted into and along a length of the scala tympani of the person's cochlea, such that a plurality of rows of individually and independently activatable VCSEL-and-ring-electrode structures extend across the width of the substrate and are spread along the length of the substrate, which is curled to fit in the scala tympani along a substantial portion of its length, while a corresponding substrate having one or more individually and independently activatable second-electrode structures is curled to fit in the scala vestibuli along a substantial portion of its length, such that the ring electrodes and the second electrodes are across from one another with the organ of Corti between these electrodes, and such that selective ones of the electrode pairs and corresponding optical emitters can be activated to stimulate and trigger NAPS in the desired nerve pathways (either at the Organ of Corti or the nerves leading from it to the cochlear nerve bundle or both).

In some embodiments, the present invention provides a method that includes obtaining a signal (such as an audio signal, a video signal, a gravitational orientation, an acceleration signal, a rotation signal, a temperature signal, a pressure signal or the like), and based on the sensed signal applying a combination of both an electrical stimulation signal and an optical stimulation signal to trigger a nerve action potential (NAP) in vivo in the cerebral cortex of an animal.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the cerebral cortex of an animal.

In some embodiments, the present invention provides a method that includes receiving a signal, and based on the received signal applying a combination of both an electrical stimulation signal and an optical stimulation signal to trigger a nerve action potential (NAP) in vivo in the spinal cord of an animal.

In some embodiments, the present invention provides an apparatus that includes an electrical-stimulation-signal source configured to selectively output an electrical stimulation signal; an optical-stimulation-signal source configured to selectively output an optical stimulation signal; and a controller and delivery medium operatively coupled to the electrical-stimulation-signal source and to the optical-stimulation-signal source and configured to control them and deliver the optical and electrical signals to trigger a nerve action potential (NAP) in vivo in the spinal cord of an animal.

In some embodiments, the present invention delivers light pulses from vertical surface-emitting lasers (VCSELs). In some embodiments, electrical pulses are also delivered at below threshold for neural excitation and spread to larger area than required for the region of interest (the area to be stimulated). The light pulse is delivered to match the exact volume that is to be stimulated: In some embodiments, the electrical energy is about 0.1 mA to about 10 mA plus optical energy=0.01-1 $J/cm^2$; Other parameters are determined by empirical experimentation, wherein frequency is generally about 10 to 1000 pulses per second.

In some such embodiments, the present invention provides, in combination with others of the other embodiments described herein, one or more of the following: a method that includes emitting pulsed light having a wavelength in a range of 1.8 microns to 2 microns and having a pulse duration from each of a plurality of vertical cavity surface-emitting lasers (VCSELs) including a first VCSEL and a second VCSEL, directing the light from the first VCSEL onto a first tissue to stimulate the first tissue but substantially not onto a second tissue, and directing the light from the second VCSEL onto the second tissue to stimulate the second tissue but substantially not onto the first tissue; such a method but further including emitting pulsed light having a wavelength in a range of 650 nm to 850 nm and having a pulse duration from each of a plurality of vertical cavity surface-emitting lasers (VCSELs) including a third VCSEL and a fourth VCSEL, directing the light from the third VCSEL onto the first tissue and illuminating the first tissue but substantially not illuminating the second tissue, detecting a reflected light from the first tissue and determining a first physiological activity of the first tissue, directing the light from the fourth VCSEL onto the second tissue and illuminating the second tissue but substantially not illuminating the first tissue, and detecting a reflected light from the second tissue and determining a second physiological activity of the second tissue. In some such embodiments, the first VCSEL and the second VCSEL are located on a single semiconductor substrate. In some such embodiments, the third VCSEL and the fourth VCSEL are located on a single semiconductor substrate. In some such embodiments, the first VCSEL, the second VCSEL, the third VCSEL and the fourth VCSEL are located on a single semiconductor substrate. Some embodiments further include integrating a first microlens with the first VCSEL and focusing the pulsed light from the first VCSEL onto the first tissue, integrating a second microlens with the second VCSEL and focusing the pulsed light from the second VCSEL onto the second tissue, integrating a third microlens with the third VCSEL and focusing the pulsed light from the third VCSEL onto the first tissue, and integrating a fourth microlens with the fourth VCSEL and focusing the pulsed light from the fourth VCSEL onto the second tissue. Some embodiments further include providing a fiber optic bundle including a plurality of optical fibers, integrating a first optical fiber with the first VCSEL and directing the pulsed light from the first VCSEL onto the first tissue, integrating a second optical fiber with the second VCSEL and directing the pulsed light from the second VCSEL onto the second tissue, integrating a third optical fiber with the third VCSEL and directing the pulsed light from the third VCSEL onto the first tissue, and integrating a fourth optical fiber with the fourth VCSEL and directing the pulsed light from the fourth VCSEL onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

In some such embodiments, the present invention provides an apparatus that includes a plurality of vertical cavity surface-emitting lasers (VCSELs) including a first VCSEL and a second VCSEL; a control circuit configured to control generation of pulsed light from the first and second VCSELs; and a light-delivery system configured to direct the light from the first VCSEL onto a first tissue but substantially not onto a second tissue in order to stimulate the first tissue; wherein the light-delivery system is further configured to direct the light from the second VCSEL onto the second tissue but substantially not onto the first tissue in order to stimulate the second tissue. In some embodiments, the apparatus further includes a plurality of vertical cavity surface-emitting lasers (VCSELs) including a third VCSEL and a fourth VCSEL. The control circuit is further configured to control generation of pulsed light from the third and fourth VCSELs; the light delivery system is further configured to direct the light from the third VCSEL onto a first tissue but substantially not onto a second tissue in order to illuminate the first tissue; the light delivery system is further configured to direct the light from the fourth VCSEL onto the second tissue but substantially not onto the first tissue in order to illuminate the second tissue; a plurality of detectors including a first detector and a second detector; the first detector is configured to detect reflected light from the first tissue to determine a first physiological activity in the first tissue; and the second detector is configured to detect reflected light from the second tissue to determine a second physiological activity in the second tissue. In some embodiments, the first VCSEL and the second VCSEL are provided on a single semiconductor substrate. In some embodiments, the third VCSEL and the fourth VCSEL are provided on a single semiconductor substrate. In some embodiments, the first VCSEL, the second VCSEL, the third VCSEL and the fourth VCSEL are provided on a single semiconductor substrate. Some embodiments further include a first microlens integrated with the first VCSEL to focus the pulsed light from the first VCSEL onto the first tissue; a second microlens integrated with the second VCSEL to focus the pulsed light from the second VCSEL onto the second tissue; a third microlens integrated with the third VCSEL to focus the pulsed light from the third VCSEL onto the first tissue; and a fourth microlens integrated with the fourth VCSEL to focus the pulsed light from the fourth VCSEL onto the second tissue. Some embodiments further include a fiber optic bundle including a plurality of optical fibers, each optical fiber having a first end and a second end; a first optical fiber operatively coupled at the first end of the first optical fiber to the first VCSEL to direct the pulsed light from the first VCSEL through the first optical fiber and the second end of the first optical fiber onto the first tissue; a second optical fiber operatively coupled at the first end of the second optical fiber to the second VCSEL to direct the pulsed light from the second VCSEL through the second optical fiber and the second end of the second optical fiber onto the second tissue; a third optical fiber operatively coupled at the first end of the third optical fiber to the third VCSEL to direct the pulsed light from the third VCSEL through the third optical fiber and the second end of the third optical fiber onto the first tissue; and a fourth optical fiber operatively coupled at the first end of the fourth optical fiber to the fourth VCSEL to direct the pulsed light from the fourth VCSEL through the fourth optical fiber and the second end of the fourth optical fiber onto the second tissue. In some embodiments, each optical fiber in the plurality of optical fibers includes a lens. In some embodiments, the first VCSEL and the third VCSEL are integrated into a first flex-cuff ring and the second VCSEL and the third VCSEL are integrated into a second flex-cuff ring. In some embodiments, the first VCSEL, the second VCSEL, the third VCSEL and the fourth VCSEL are mounted in a biocompatible housing having an optical feed through.

The present invention also contemplates various combinations and subcombinations of the embodiments set forth in the above description.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A method for stimulating neurons of a plurality of auditory nerve pathways of a person to provide sensations for the person, the plurality of auditory nerve pathways including a first auditory nerve pathway and a second auditory nerve pathway, the method comprising:
generating a plurality of stimulation light signals, including a first stimulation light signal and a second stimulation light signal, that, when applied to a neuron of the person while the neuron is sensitized, each will stimulate a nerve action potential (NAP) in the neuron;
generating a first electrical sensitizing signal, that, when applied to the neuron of the person, will sensitize the neuron to trigger a NAP in the neuron upon application of one or more of the plurality stimulation light signals to the neuron;
delivering, during a first time period, the first electrical sensitizing signal to a plurality of neurons of the plurality of auditory nerve pathways of the person;
delivering, during a second time period that starts after a start time of the first time period, the first stimulation light signal to one or more neurons of the first auditory nerve pathway of the person;
delivering, during the second time period, the second stimulation light signal to one or more neurons of the second auditory nerve pathway of the person;
selectively controlling the plurality of stimulation light signals to provide controlled optical stimulation in order to trigger NAPs in the one or more neurons in the first auditory nerve pathway independently from triggering NAPs in the one or more neurons in the second auditory nerve pathway;
receiving an audio signal;
determining whether a first temporal period of the received audio signal includes wideband audio-spectral content; and
based on the determination of the wideband audio-spectral content, delivering an electrical-stimulation signal corresponding to the first temporal period to the plurality of auditory nerve pathways simultaneously, with sufficient current to trigger NAPs in the plurality of auditory nerve pathways without use of the light signals.

2. The method of claim 1, the method further comprising:
processing the received audio signal to obtain frequency and intensity information, wherein the delivering of the first and second stimulation light signals includes delivering the first and second stimulation light signals to an auditory portion of a cochlea of the person, and wherein the selectively controlling of the plurality of stimulation light signals includes selectively controlling the generating and delivering of the first and second stimulation light signals such that the first and second stimulation light signals are delivered to selected locations of the cochlea of the person based on the frequency information and at selected pulse-repetition rates based on the intensity information.

3. The method of claim 1, wherein the delivering of the first light signal occurs inside a cochlea of the person and the delivering the second light signal to one or more neurons occurs inside the cochlea of the person.

4. The method of claim 1, wherein the delivering of light signals further includes delivering infrared light from a laser.

5. The method of claim 1, wherein the delivering of light signals further includes delivering infrared light from a vertical-cavity surface-emitting laser (VCSEL).

6. The method of claim 1, wherein the delivering of light signals further includes delivering the light signals to central portions of the neurons.

7. The method of claim 1, wherein the delivering of the light signals further includes obtaining a plurality of light signals from one or more laser light sources and delivering the obtained light signals to discrete portions of excitable tissues, said signals being interpretable by the person's brain as sensory responses.

8. The method of claim 1, wherein the delivering of the electrical-stimulation signal to the plurality of auditory nerve pathways includes delivering the electrical-stimulation signal to auditory nerve pathways for perceived frequencies of 50 Hertz (Hz), 75 Hz, 100 Hz, 400 Hz, and 500 Hz.

9. An apparatus comprising:
a plurality of independently controllable light sources that are configured to generate a plurality of stimulation light signals, including a first stimulation light signal and a second stimulation light signal, that, when applied to a neuron of the person while the neuron is sensitized, each will stimulate a nerve action potential (NAP) in the neuron;
electrical driver electronics that generate a first electrical sensitizing signal, that, when applied to the neuron of the person, will sensitize the neuron to trigger a NAP in the neuron upon application of one or more of the plurality of stimulation light signals to the neuron;
a first transmission medium configured to transmit, during a first time period, the first electrical sensitizing signal to a plurality of neurons of a plurality of auditory nerve pathways of the person including a first auditory nerve pathway and a second auditory nerve pathway;
a second transmission medium configured to transmit, during a second time period that starts after a start time of the first time period, the first stimulation light signal from the plurality of light sources to one or more neurons of the first auditory nerve pathway of the person, and to transmit, during the second time period, the second stimulation light signal from the plurality of light sources to one or more neurons of the second auditory nerve pathway of the person;
a controller operatively coupled to the plurality of light sources to selectively control the plurality of stimulation light signals, and operatively coupled to the electrical driver electronics to selectively control the first electrical sensitizing signal, such that in combination with the first electrical sensitizing signal the first stimulation light signal provides controlled optical stimulation to trigger nerve action potentials (NAPs) produced by the one or more neurons in the first auditory nerve pathway but not the second auditory pathway, and the second stimulation light signal provides controlled optical stimulation to trigger NAPs by the one or more neurons in the second auditory nerve pathway but not the first auditory pathway, in order to provide auditory sensations for the person;

a microphone configured to receive an audio signal;

an audio-signal processor that determines whether a first temporal period of the received audio signal includes a wideband audio-spectral content, wherein the controller is further configured to, based on the determination of the wideband audio-spectral content, cause the electrical driver electronics to deliver an electrical-stimulation signal corresponding to the first temporal period to the plurality of auditory nerve pathways simultaneously, with sufficient current to trigger NAPs in the plurality of auditory nerve pathways without use of the light signals.

10. The apparatus of claim 9, wherein the audio-signal processor processes the received audio signal to obtain frequency and intensity information, wherein the second transmission medium is further configured to transmit the first and second light signals to an auditory portion of a brainstem or midbrain of the person, and wherein the controller is further configured to selectively control the plurality of independently controllable light sources and the second transmission medium such that the first and second stimulation light signals are transmitted to selected locations of the brainstem or midbrain of the person based on the frequency information and at selected pulse-repetition rates based on the intensity information.

11. The apparatus of claim 9, wherein the control of the light signals provided by the controller includes selective control of a wavelength of the plurality of light signals.

12. The apparatus of claim 9, wherein the second transmission medium includes a plurality of parallel optical-signal-transmission channels.

13. The apparatus of claim 12, wherein the second transmission medium includes a plurality of optical fibers each of which transmits a different signal.

14. The apparatus of claim 9, wherein the microphone has a signal output operatively coupled to a wireless transmitter that is configured to transmit information based on the signal output to the controller.

15. The apparatus of claim 14, wherein the audio-signal processor generates the information transmitted by the wireless transmitter to the controller, wherein the information includes frequency information and intensity information, and wherein the controller is further configured to selectively control the optical stimulation to be interpretable by a living animal's brain as having one or more frequency components and an intensity, in order to encode hearing.

16. The apparatus of claim 9, wherein the plurality of light sources includes a plurality of vertical-cavity surface-emitting lasers (VCSELs).

17. The apparatus of claim 9, wherein the delivered electrical-stimulation signal due to the detected wideband audio-spectral content triggers auditory nerve pathways for perceived frequencies of 50 Hertz (Hz), 75 Hz, 100 Hz, 400 Hz, and 500 Hz.

18. An apparatus for stimulating neurons of a plurality of auditory nerve pathways, of a person to provide sensations for the person, the plurality of auditory nerve pathways including a first auditory nerve pathway and a second auditory nerve pathway, the apparatus comprising:

means for generating a plurality of stimulation light signals, including a first stimulation light signal and a second stimulation light signal, that, when applied to a neuron of the person while the neuron is sensitized, each will stimulate a nerve action potential (NAP) in the neuron;

means for generating a first electrical sensitizing signal, that, when applied to the neuron of the person, will sensitize the neuron to trigger a NAP in the neuron upon application of one or more of the plurality of stimulation light signals to the neuron;

means for delivering, during a first time period, the first electrical sensitizing signal to a plurality of neurons of the plurality of auditory nerve pathway of the person;

means for delivering, during a second time period that starts after a start time of the first time period, the first stimulation light signal to one or more neurons of the first auditory nerve pathway of the person;

means for delivering, during the second time period, the second stimulation light signal to one or more neurons of the second auditory nerve pathway of the person;

means for selectively controlling the plurality of stimulation light signals to provide controlled optical stimulation in order to trigger NAPs in the one or more neurons in the first auditory nerve pathway independently from triggering NAPs in the one or more neurons in the second auditory nerve pathway;

means for receiving an audio signal;

means for determining whether a first temporal period of the received audio signal includes a wideband audio-spectral content; and means for, based on the determination of the wideband audio-spectral content, delivering an electrical-stimulation signal corresponding to the first temporal period to the plurality of auditory nerve pathways simultaneously, with sufficient current to trigger NAPs in the plurality of auditory nerve pathways without use of the light signals.

19. The apparatus of claim 18, the apparatus further comprising:

means for processing the received audio signal to obtain frequency and intensity information, wherein the means for delivering the first stimulation light signal delivers the first light signal to an auditory portion of a cochlea of the person, and wherein the means for selectively controlling the plurality of stimulation light signals controls the means for generating the plurality of stimulation light signals and the means for delivering the first stimulation light signal such that the first stimulation light signal is delivered to selected locations of the cochlea of the person based on the frequency information and at selected pulse-repetition rates based on the intensity information.

20. The apparatus for of claim 18, wherein the means for selectively controlling provides the controlled optical stimulation based on detected narrow-band content in an analyzed audio signal, but provides threshold-level electrical stimulation based on detected broadband audio content in the analyzed audio signal.

21. The apparatus of claim 18, wherein the means for generating the plurality of stimulation light signals includes a hexagonal-shaped vertical-cavity surface-emitting laser (VCSEL) array.

22. The apparatus of claim 18, wherein the delivered electrical-stimulation signal due to the detected wideband audio-spectral content triggers auditory nerve pathways for perceived frequencies of 50 Hertz (Hz), 75 Hz, 100 Hz, 400 Hz, and 500 Hz.

* * * * *